US008624002B2

(12) United States Patent
Gu et al.

(10) Patent No.: US 8,624,002 B2
(45) Date of Patent: Jan. 7, 2014

(54) PROSTAGLANDIN E2 BINDING PROTEINS AND USES THEREOF

(75) Inventors: Jjijie Gu, Shrewsubry, MA (US); Charles W. Hutchins, Green Oaks, IL (US); Rong-rong Zhu, Southborough, MA (US); Jianwei Shen, Lake Bluff, IL (US); Maria C. Harris, Shrewsbury, MA (US); Eileen Belanger, Northbridge, MA (US); Anwar Murtaza, Westborough, MA (US); Edit Tarcsa, Westborough, MA (US); William B. Stine, Shrewsbury, MA (US); Chung-ming Hsieh, Newton, MA (US)

(73) Assignee: AbbVie, Inc., North Chicago, IL (US)

( * ) Notice: Subject to any disclaimer, the term of this patent is extended or adjusted under 35 U.S.C. 154(b) by 835 days.

(21) Appl. No.: 12/499,646

(22) Filed: Jul. 8, 2009

(65) Prior Publication Data

US 2010/0040537 A1    Feb. 18, 2010

Related U.S. Application Data

(60) Provisional application No. 61/134,264, filed on Jul. 8, 2008, provisional application No. 61/197,258, filed on Oct. 23, 2008.

(51) Int. Cl.
*C07K 16/18* (2006.01)

(52) U.S. Cl.
USPC ............... 530/387.3; 530/387.1; 530/388.23; 530/388.24

(58) Field of Classification Search
USPC .................. 530/387.1, 387.3, 388.23, 388.24
See application file for complete search history.

(56) References Cited

U.S. PATENT DOCUMENTS

| 6,004,549 A * | 12/1999 | Reichert et al. ............. 424/85.7 |
| 2006/0177447 A1 | 8/2006 | Xu et al. |
| 2008/0050357 A1 | 2/2008 | Gustafsson et al. |

OTHER PUBLICATIONS

Mariuzza et al. (Annu. Rev. Biophys. Biophys. Chem. 1987; 16: 139-159).*
Rudikoff et al (Proc. Natl. Acad. Sci. USA. 1982; 79: 1979-1983).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Mnich et al. (J. Immunol. Nov. 1, 1995; 155 (9): 4437-44).*
Pechenov et al. (J. Control Release. Apr. 16, 2004; 96 (1): 149-58).*
Kobayashi et al. (J. Nucl. Med. Apr. 2000; 41 (4): 755-62).*
Frost (Expert Opin. Drug Deliv. Jul. 2007 ;4 (4): 427-40).*
Written Opinion for PCT Application No. PCT/US2009/049953, dated Oct. 29, 2009 (10 pages).
Portanova et al., Selective Neutralization of Prostaglandin E 2 Blocks Inflammation, Hyperalgesia, and Interleukin 6 Production In Vivo, J. Exp. Med., Sep. 1996, p. 883-91.
Mnich et al., Characterization of a Monoclonal Antibody that Neutralizes the Activity of Prostaglandin E2, J. of Immunology, 1995:155, p. 4437-44.

\* cited by examiner

*Primary Examiner* — Stephen Rawlings
(74) *Attorney, Agent, or Firm* — Finnegan, Henderson, Farabow, Garrett & Dunner, LLP

(57) ABSTRACT

The present invention encompasses prostaglandin $E_2$ ($PGE_2$) binding proteins. The invention relates to antibodies that are wild-type, chimeric, CDR grafted and humanized. Preferred antibodies have high affinity for prostaglandin $E_2$ and neutralize prostaglandin $E_2$ activity in vitro and in vivo. An antibody of the invention can be a full-length antibody, or an antigen-binding portion thereof. Methods of making and methods of using the antibodies of the invention are also provided. The antibodies, or antigen-binding portions, of the invention are useful for detecting prostaglandin $E_2$ and for inhibiting prostaglandin $E_2$ activity, e.g., in a human subject suffering from a disorder in which prostaglandin $E_2$ activity is detrimental.

23 Claims, 9 Drawing Sheets

|  |  | (1) | 1 | 10 | 20 | 30 | 40 | 50 | 60 |
|---|---|---|---|---|---|---|---|---|---|

(Seq ID No. 40)  2B5-7.0 VH  (1)  QVQLQQSGPELVRPGSSVKISCKASGYTFTKYWLGWVKQRPGHGLEWIGDIYP*YTHY
(Seq ID No. 42)  2B5-8.0 VH  (1)  QVQLQQSGPELVRPGSSVKISCKASGYTFTKYWLGWVKQRPGHGLEWIGDIYP*YTHY
(Seq ID No. 44)  2B5-9.0 VH  (1)  QVQLQQSGPELVRPGSSVKISCKASGYTFTKYWLGWVKQRPGHGLEWIGDIYPYGDYTHY
(Seq ID No. 82)  Consensus   (1)  QVQLQQSGPELVRPGSSVKISCKASGYTFTKYWLGWVKQRPGHGLEWIGDIYPGYDYTHY

(61) 61     70     80     90     100     116

(Seq ID No. 40)  2B5-7.0 VH  (61)  NEKFKDKATLTVDTSSSTAYMQLSSLTSEDSA**CARSDGSSTYWGQGTLVTVSA
(Seq ID No. 42)  2B5-8.0 VH  (61)  NEKFKDKATLTVDTSSSTAYMQLSSLTSEDSA**CARSDGSSTYWGQGTLVTVSA
(Seq ID No. 44)  2B5-9.0 VH  (61)  NEKFKDKATLTVDTSSSTAYMQLSSLTSEDSA**CARSDGSSTYWGQGTLVTVSA
(Seq ID No. 82)  Consensus   (61) NEKFKDKATLTVDTSSSTAYMQLSSLTSEDSAVYFCARSDGSSTYWGQGTLVTVSA (1) 1     10     20     30     40     50     60

(Seq ID No. 41)  2B5-7.0 VL  (1)  DVLMTQTPLSLPVSLGDQASISCTSSQNIVHSNGNTYLEWYLQRPGQSPKLLIYKVSNRF
(Seq ID No. 43)  2B5-8.0 VL  (1)  DVLMTQTPLSLPVSLGDQASISCTSSQNIVHSNGNTYLEWYLQRPGQSPKLLIYKVSNRF
(Seq ID No. 45)  2B5-9.0 VL  (1)  DVLMTQTPLSLPVSLGDQASISCTSSQNIVHSNGNTYLEWYLQRPGQSPKLLIYKVSNRF
(Seq ID No. 83)  Consensus   (1)  DVLMTQTPLSLPVSLGDQASISCTSSQNIVHSNGNTYLEWYLQRPGQSPKLLIYKVSNRF

(61) 61     70     80     90     100     113

(Seq ID No. 41)  2B5-7.0 VL  (61)  SGVPDRFSGSGSGTVFTLKISRVEAEDLGVYYCFQVSHVPYTFGGGTKLEIKR
(Seq ID No. 43)  2B5-8.0 VL  (61)  SGVPDRFSGSGSGTVFTLKISRVEAEDLGVYYCFQVSHVPYTFGGGTKLEIKR
(Seq ID No. 45)  2B5-9.0 VL  (61)  SGVPDRFSGSGSGTVFTLKISRVEAEDLGVYYCFQVSHVPYTFGGGTKLEIKR
(Seq ID No. 83)  Consensus   (61) SGVPDRFSGSGSGTVFTLKISRVEAEDLGVYYCFQVSHVPYTFGGGIKLEIKR

FIGURE 8

PROSTAGLANDIN E2 BINDING PROTEINS AND USES THEREOF

REFERENCE TO RELATED APPLICATIONS

This application is a non-provisional application claiming priority to U.S. Provisional Application Ser. No. 61/134,264, filed Jul. 8, 2008, and U.S. Provisional Application Ser. No. 61/197,258, filed Oct. 23, 2008, the contents of which are hereby incorporated by reference.

FIELD OF THE INVENTION

The present invention relates to binding proteins and compositions thereof, for example antibodies and antigen binding portions specific to lipid metabolites such as prostaglandin E2 ($PGE_2$), and methods of making, characterizing, and using them in the prevention, diagnosis, and treatment of diseases.

BACKGROUND OF THE INVENTION

Bioactive lipids such as prostaglandin (PG), thromboxane (TX), leukotriene (LT), and sphingosine-1-phosphate play a critical physiological role in the etiology of various disorders. (Wymann, M P and Schneiter R, Nat. Rev. Mol. Cell. Biol. 9(2):162-76 (2008)). During inflammation, cellular phospholipases, especially phospholipases A2 and C, are activated and degrade cell membrane phospholipids to arachidonic acid (AA). AA is metabolized by two major routes, the cyclooxygenase (COX) and lipooxygenase (LO) pathways. The COX pathway produces prostaglandins ($PGD_2$, $PGE_2$, $PGF_{2\alpha}$, prostacyclin or $PGI_2$, and thromboxane A2 or $TXA_2$). The LO pathway has two branches; the 5-LO pathway produces leukotrienes (e.g., LTA4, LTB4, LTC4, LTD4, LTE4, and LTF4) and the 15-LO pathway produces lipoxins (e.g., LXA4, LXB4). Prostanoids such as prostaglandin (PG), thromboxane (TX) and leukotriene (LT) have various physiological activities for maintaining local homeostasis in the body (The Pharmacological Basis of Therapeutics, Gilman, et al., eds., 7th Ed., p. 660, Macmillan Publishing Co., New York (1985)). The products of COX, PG G2/PG H2, are converted to specific PGs by the actions of tissue specific isomerases to yield $PGI_2$, $TXA_2$, $PGD_2$, $PGE_2$, and $PGF_{2\alpha}$. The biological functions of PGs are mediated by tissue-specific cell surface rhodopsin-like seven transmembrane spanning G protein-coupled receptors (GPCRs). The precise physiological/pathological role of each PG is determined by the cellular context, receptor expression profile, ligand affinity, and differential coupling to signal transduction pathways (Haluska et al., Annu. Rev. Pharm. Tox. 10:213 (1989); Prostanoids and their Receptors. In Comprehensive Medicinal Chemistry, p. 643, Pergamon Press, Oxford (1990)). PGs play a wide variety of physiological roles in the regulation of modulation of vasomotricity, the sleep/wake cycle, intestinal secretion, lipolysis, glomerular filtration, mast cell degranulation, neurotransmission, platelet aggregation, leuteolysis, myometrial contraction and labor, inflammation and arthritis, patent ductus arteriosus, cell growth and differentiation, and immune responses generally. Patho-physiologically, PGs have been implicated in a variety of diseases including pain and inflammation, cancer, neurological diseases, cardiovascular diseases, and hypertension.

Prostaglandin $E_2$ ($PGE_2$) is a member of the prostanoid family. $PGE_2$ participates widely in the contraction and relaxation of the gastrointestinal tract, secretion of gastric acid, relaxation of smooth muscle, and release of neurotransmitters. Four subtype receptors for $PGE_2$ have been identified, including EP1, EP2, EP3, and EP4 (Negishi, M. et al., J. Lipid Mediators Cell Signalling, 12:379-391 (1995)), each of which is involved in a different signal transduction pathway.

$PGE_2$ is the main product of the COX pathway of AA metabolism. It is the major PG synthesized in the joints and plays an important role in inflammation and the pathogenesis of arthritis. Five $PGE_2$ synthases have been identified. (Smith W L, Am. J. Physiol. 263(2 Pt 2):F181-91 (1992)). Of these five, membrane PGE synthase (mPGES)-1 appears to be the key $PGE_2$ convertase enzyme responsible for $PGE_2$ production. MPGES-1 displays the highest catalytic activity relative to other PGE synthases and functions in conjunction with COX-1 and/or COX-2, to convert $PGH_2$ to $PGE_2$. Studies using mPGES-1 KO mice (Kamei, D., et al., J. Biol. Chem., 279(32):33684-95 (2004); Trebino, C. E., et al., Proc. Natl. Acad. Sci. USA 100(15):9044-9 (2003), specific $PGE_2$ receptor isoform KO mice (McCoy, J. M., et al. J. Clin. Invest., 110(5):651-8 (2002); Majima, M., et al. Trends Pharmacol. Sci., 24(10):524-9 (2003); and Amano, H., et al., J. Exp. Med., 197(2):221-32 (2003); and anti-$PGE_2$ specific antibodies (Portanova, J. P., et al., J. Exp. Med., 184(3):883-91 (1996); Zhang, Y., et al., J. Pharmacol. Exp. Ther., 283(3): 1069-75 (1997) suggest that $PGE_2$ plays a major role in animal models of rheumatoid arthritis (RA), pain and inflammation and cancer development. In the absence of mPGES-1, levels of COX-1, COX-2, and other $PGE_2$ synthases remain relatively unaltered. The mPGES-1 KO mice are viable, fertile, and develop normally compared to wild type mice. However, they display a drastic reduction in both basal levels of $PGE_2$ production as well as in $PGE_2$ production from macrophages following challenge with various inflammatory stimuli. In addition, production of TXA2 is increased. The mPGES-1 KO mice show reduced incidence and severity of arthritis development and show resistance to pain and inflammation in various models. Several laboratories have independently generated various EP receptor isoform KO mice. These mice are viable, fertile and develop normally. Studies using specific EP isoform KO mice demonstrate that the various functions of $PGE_2$ are mediated via specific EP isoforms. For example, the lack of EP4 isoform clearly affects the severity of arthritis development in mice, whereas the lack of EP3 influences tumor development and progression by modulating VEGF production by stromal cells and angiogenesis.

Defects in the biosynthesis and metabolism of prostaglandins are now believed to play an important part in the etiology of autoimmune and inflammatory disorders. For example, the synovial tissues from patients suffering from rheumatoid arthritis produce larger amounts of $PGE_2$ and prostaglandin F2α, ($PGF_{2\alpha}$) compared to the synovial tissues from unaffected subjects (Blotman, F., et al., Rev. Rhum. Mal. Osteoartic, 46(4):243-7 (1979)). Similarly, an increased synthesis of $PGE_2$ and $PGF_{2\alpha}$ occurs in patients exhibiting systemic and gastrointestinal symptoms secondary to food intolerance. Thus, migraine headaches secondary to the ingestion of certain foods could be the result of an increased synthesis of 2-series prostaglandins. Multiple sclerosis is also associated with an imbalance in the normal levels of the prostaglandins, $PGE_1$ and $PGE_2$. Many aspects of reproduction, for example, fertility, pregnancy and labor, may be regulated by prostaglandins. Prostaglandins also play a major role in reproductive physiology. Excessive prostaglandin synthesis causes dysmenorrhea and parturition, which may be induced by administering prostaglandins intravenously or by insertion of a prostaglandin pessary. (Wang L. et al., Occup. Environ. Med. 61(12):1021-1026 (2004)). Excessive synthesis of $PGE_2$ also plays a major role in disorders of reproduction, such as infertility, repeated miscarriage, preeclampsia, and eclampsia. A need therefore exists for antibodies specific to $PGE_2$ that block or modulate its biological functions, which may be used to prevent and treat the diseases associated with excess production of $PGE_2$ as well as diagnostic purposes.

The generation of a highly specific, high affinity ($K_D$ is about 300 pM) anti-$PGE_2$ mAb, 2B5, has been reported. (Mnich S J, et al. J. Immunol. 155(9):4437-44 (1995)). The efficacy of 2B5 relative to indomethacin, a COX-1,2 inhibitor, was determined in animal models of pain and inflammation in mice and adjuvant-induced arthritis in rats. (Portanova J P et al., J. Exp. Med. 184(3):883-91 (1996)). These studies clearly showed that 2B5 was as effective as indomethacin in reducing pain and inflammation as well as the severity of arthritis, suggesting that $PGE_2$ is a key participant in the COX-1,2 pathway of AA metabolism in these animal models.

Inhibition of pan-PG production by COX-inhibitors has been a well-established therapeutic strategy for decades. Two isoforms of COX, COX-1 and COX-2, are known, each of which are encoded by a distinct gene. The two isoforms carry out essentially the same catalytic reaction and have similar tertiary structures (Garavito R M, et al., Annu. Rev. Biophys. Biomol. Struct. 32:183-206 (2003)). COX-1 is constitutively expressed in nearly all tissues and is believed to be largely responsible for the normal "house keeping" functions, such as gastric cytoprotection and homeostasis. COX-2, by contrast, is constitutively expressed in particular tissues, and is highly inducible at sites of inflammation and cancer. Thus, COX-2-mediated PG production is thought to play an important role at the site of inflammation and cancer. The traditional non-steroidal anti-inflammatory drugs (NSAIDs), e.g., aspirin, indomethacin, ibuprofen) inhibit both COX isoforms. These compounds are the most widely used drugs for pain, rheumatoid arthritis (RA), osteoarthritis (OA), and cardiovascular diseases and now are under consideration for the prevention of colon cancer and AD. The main liabilities of traditional NSAIDs are gastric and renal adverse events, in high-risk populations, which are believed to be due to inhibition of COX-1. Therefore, the second generation of NSAIDs, the COX-2 selective inhibitors (e.g., celecoxib, Celebrex™; rofecoxib, Vioxx™; valdecoxib, Bextra™), are believed to have a better therapeutic profile. This assumption has resulted in their widespread use for pain, RA, and OA. Since the approval of the first COX-2 inhibitor in 1999 the combined sales of COX-2 inhibitors in 2004 was approximately US $ 5 billion. However, recently some COX-2 selective inhibitors were taken off the market, and are under FDA review, due to cardiovascular side-effects in high risk patients for certain COX-2 inhibitors. The liabilities associated with COX inhibitors probably arose due to their ability to inhibit all PGs, and in particular due to their ability to differentially interfere with $PGI_2$ and $TXA_2$ production, both of which play an important role in maintaining cardiovascular homeostasis (Martinez-González J. et al., Curr. Pharm. Des. 13(22):2215-2227 (2007)). The inhibition of COX may make more AA available to the LO pathways, thus increasing the production of leukotrienes and lipoxins, which may contribute to COX inhibition-associated adverse effects. Recent studies using COX-1 and/or COX-2 knockout mice and COX-1 and COX-2 specific inhibitors also suggest that assumptions concerning the physiological roles of the two COX-isoforms may not be correct. (Loftin, C. D., et al. Prostaglandins Other Lipid Mediat. 68-69:177-85 (2002)). These studies suggest that both COX-1 and COX-2 play an important role in supplying PGs to maintain tissue homeostasis and both isoforms may contribute to disease development, such as pain, inflammation and cancer. Therefore, blocking detrimental $PGE_2$ downstream of COX-1 and COX-2 pathway with a specific antibody appears to be an attractive approach for the treatment of certain human diseases.

Another example of an important bioactive prostaglandin is $PGD_2$. $PGD_2$ is the major cyclooxygenase product of arachidonic acid produced from mast cells on immunological challenge (Lewis, et al., J. Immunol. 129:1627-1631 (1982)). Activated mast cells, a major source of $PGD_2$, are one of the key players in driving the allergic response in conditions such as asthma, allergic rhinitis, allergic conjunctivitis, allergic dermatitis and other diseases (Brightling, et al., Clin. Exp. Allergy 33:550-556 (2003)). Recent studies have shown that $PGD_2$ exerts its effects through two different G-protein-coupled receptors (GPCRs), the D-prostanoid receptor (DP) and the chemoattractant receptor-homologous molecule expressed on T helper type-2 cells (CRTH2), expressed in various human tissues. The $PGD_2$/CRTH2 system mediates the chemotaxis of eosinophils, basophils, and Th2 cells, which are involved in the induction of allergic inflammation (Ulven T et al., Curr. Top. Med. Chem. 6(13):1427-1444 (2006)). Many of the actions of $PGD_2$ are mediated through its action on the D-type prostaglandin ("DP") receptor, a G protein-coupled receptor expressed on epithelium and smooth muscle. In asthma, the respiratory epithelium has long been recognized as a key source of inflammatory cytokines and chemokines that drive the progression of the disease (Holgate, et al., Am. J. Respir. Crit. Care Med. 162:113-117 (2000)). In an experimental murine model of asthma, the DP receptor is dramatically up-regulated on airway epithelium on antigen challenge (Matsuoka, et al., Science 287:2013-2017 (2000)). The DP receptor is involved in human allergic rhinitis, a frequent allergic disease that is characterized by the symptoms of sneezing, itching, rhinorea and nasal congestion. DP antagonists have been shown to be effective at alleviating the symptoms of allergic rhinitis in multiple species, and more specifically have been shown to inhibit the antigen-induced nasal congestion, the most manifest symptom of allergic rhinitis (Jones, et al., Am. J. Resp. Crit. Care Med. 167:A218 (2003); Arimura, et al., S-5751. J. Pharmacol. Exp. Ther. 298(2):411-9 (2001)). DP antagonists are also effective in experimental models of allergic conjunctivitis and allergic dermatitis (Arimura et al., S-5751. J. Pharmacol. Exp. Ther. 298(2):411-9 (2001); Torisu, et al., Bioorg. & Med. Chem. 12:5361-5378 (2004)). A need therefore also exists for antibodies specific to $PGD_2$ and blocking or modulating its biological functions therefore may be used to prevent and treat the diseases associated with excess production of $PGD_2$.

Sphingosine-1-phosphate (S1P) is another example of a bioactive lipid that induces many cellular effects, including those that result in platelet aggregation, cell proliferation, cell morphology, tumor cell invasion, endothelial cell chemotaxis, and endothelial cell in vitro angiogenesis. S1P receptors are therefore good targets for therapeutic applications such as wound healing and tumor growth inhibition. S1P signals cells in part via a set of G protein-coupled receptors named S1P1, S1P2, S1P3, S1P4, and S1P5 (formerly called EDG-1, EDG-5, EDG-3, EDG-6, and EDG-8, respectively). These receptors share 50-55% amino acid and cluster identity with three other receptors (LPA1, LPA2, and LPA3 (formerly EDG-2, EDG-4 and EDG-7)) for the structurally-related lysophosphatidic acid (LPA). (Ishii, I. et al., Mol. Pharmacol. 58(5): 895-902 (2000)). A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit, and each subunit can then associate with effector proteins, which activate second messengers leading to a cellular response. Eventually the GTP on the G-proteins is hydrolyzed to GDP, and the subunits of the G-proteins re-associate with each other and then with the receptor. Amplification plays a major role in the general GPCR pathway. The binding of one ligand to one receptor leads to the activation of many G-proteins, each capable of associating with many effector proteins, leading to an amplified cellular response. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other responses. For example, the response specificity of the S1P receptors could allow for an S1P mimetic that initiates platelet aggregation without affecting cell morphology.

S1P is formed as a metabolite of sphingosine in its reaction with sphingosine kinase, and is abundantly stored in platelet aggregates where high levels of sphingosine kinase exist and sphingosine lyase is absent. S1P is released during platelet aggregation, accumulates in serum and is also found in malignant ascites. S1P biodegradation most likely proceeds via hydrolysis by ectophosphohydrolases, specifically the sphingosine 1-phosphate phosphohydrolases. A need therefore exists for antibodies specific to S1P for modulating its biological functions either by blocking its interaction with receptors or stabilizing S1P and enhancing its biological effects, for use in preventing or treating autoimmune diseases, inflammatory diseases, and cancers.

Due to the role of PGE2 in a variety of human disorders, therapeutic strategies have been designed to inhibit or counteract PGE2 activity. In particular, therapeutic antibodies suitable for delivery to humans that bind to, and neutralize, PGE2 have not been reported. There exists a need in the art for improved antibodies capable of binding and neutralizing PGE2.

SUMMARY OF THE INVENTION

The present invention relates to binding proteins specific to lipid metabolites, such as prostaglandin E2 ($PGE_2$). The $PGE_2$ binding proteins of the invention include, but are not limited to, antibodies, antigen binding fragments, and antigen binding fragments with various scaffolds, that are capable of binding $PGE_2$.

One aspect of the invention pertains to binding proteins capable of binding $PGE_2$. In an embodiment, the binding proteins of the invention have neutralizing, stabilizing, antagonist, and/or agonist activities. In another embodiment, the binding proteins are capable of modulating a biological function of $PGE_2$. For example, the binding proteins are capable of at least partially neutralizing $PGE_2$.

In one aspect of the invention, the binding proteins are capable of binding $PGE_2$ and preventing the binding of $PGE_2$ to one or more $PGE_2$ receptors (e.g., EP1, EP2, EP3, and EP4). In an embodiment of the invention, the binding proteins are capable of binding $PGE_2$ and preventing the binding of $PGE_2$ to the EP 1, EP2, EP3, and EP4 receptors.

The invention provides methods of making, characterizing and using the PGE2 binding proteins as a monotherapy or as a combination therapy with other therapeutic agents; and methods in the prevention and/or treatment of diseases mediated by $PGE_2$, for example, autoimmune and inflammatory diseases such as, for example, rheumatoid arthritis, Crohn's disease, osteoarthritis, AMD, lymphadenopathies, hemolytic anemias, purpura, ankylosing spondylitis, multiple sclerosis, diabetes mellitus, cancer, pain, bone loss/restoration, atherosclelotic diseases, disorders of reproduction, and other diseases. The binding proteins of the invention can also be used in the diagnosis of such diseases.

In an embodiment of the invention, a binding protein is an isolated antibody, or antigen binding fragment thereof, that binds $PGE_2$. Such binding may be demonstrated in a biotinylated $PGE_2$ ELISA based assay with an $EC_{50}$ selected from the group consisting of about $1 \times 10^{-6}$ to about $1 \times 10^{-7}$ M, about $1 \times 10^{-7}$ to about $1 \times 10^{-8}$ M, about $1 \times 10^{-8}$ to about $1 \times 10^{-9}$ M, about $10^{-9}$ to about $10^{-10}$ M, about $1 \times 10^{-10}$ to about $1 \times 10^{-11}$ M and about $10^{-11}$ to about $10^{-12}$ M. In another embodiment, binding of the binding proteins to $PGE_2$ is demonstrated in a $^3$H-labelled $PGE_2$ based radioimmunoassay with a $K_D$ selected from the group consisting of about $1 \times 10^{-6}$ to about $1 \times 10^{-7}$ M, about $1 \times 10^{-7}$ to about $1 \times 10^{-8}$ M, about $1 \times 10^8$ to about $1 \times 10^{-9}$ M, about $10^{-9}$ to about $10^{-10}$M, about $1 \times 10^{-10}$ to about $1 \times 10^{-11}$ M, and about $10^{-11}$ to about $10^{-12}$. In another embodiment, binding of the binding proteins to $PGE_2$ is demonstrated in a FLIPR wherein $PGE_2$-induced calcium influx mediated through its receptor EP4 is inhibited by binding of the binding proteins to $PGE_2$, with an $IC_{50}$ selected from the group consisting of about $1 \times 10^{-6}$ to about $1 \times 10^{-7}$ M, about $1 \times 10^{-7}$ to about $1 \times 10^{-8}$ M, about $1 \times 10^{-8}$ to about $1 \times 10^{-9}$ M, about $10^{-9}$ to about $10^{-10}$ M, about $1 \times 10^{-10}$ to about $1 \times 10^{-11}$ M, and about $10^{-11}$ to about $10^{-12}$.

In an embodiment, the antibodyinhibits the binding of biotinylated $PGE_2$ to the EP 1, EP2, EP3, and/or EP4 receptor on the cell surface in FACS-based receptor binding assay, or the antibody inhibits the binding of biotinylated $PGE_2$ to the EP1, EP2, EP3, and/or EP4 receptor on the membrane preparation made using receptor expressing cells in ELISA-based receptor binding assay with an $IC_{50}$ of about $1 \times 10^{-6}$ to about $1 \times 10^{-7}$ M, about $1 \times 10^{-7}$ to about $1 \times 10^{-8}$ M, about $1 \times 10^{-8}$ to about $1 \times 10^{-9}$ M, about $10^{-9}$ to about $10^{-10}$ M, about $1 \times 10^{-10}$ to about $1 \times 10^{-11}$ M, and about $10^{-11}$ to about $10^{-12}$ or the antibody inhibits the binding of $^3$H-$PGE_2$ to the EP 1, EP2, EP3, and/or EP4 receptor on the cell surface or on the membrane preparation in an $^3$H $PGE_2$ based radioimmunoassay with a $IC_{50}$ of about $1 \times 10^{-6}$ to about $1 \times 10^{-7}$ M, about $1 \times 10^{-7}$ to about $1 \times 10^{-8}$ M, about $1 \times 10^{-8}$ to about $1 \times 10^{-9}$ M, about $10^{-9}$ to about $10^{-10}$M, about $1 \times 10^{-10}$ to about $1 \times 10^{-11}$ M, and about $10^{-11}$ to about $10^{-12}$ and/or the antibody inhibits $PGE_2$ induced calcium flux in a EP4 mediated FLIPR assay with an $IC_{50}$ of about $1 \times 10^{-6}$ to about $1 \times 10^{-7}$ M, about $1 \times 10^{-7}$ to about $1 \times 10^{-8}$ M, about $1 \times 10^{-8}$ to about $1 \times 10^{-9}$ M, about $10^{-9}$ to about $10^{-10}$ M, about $1 \times 10^{-10}$ to about $1 \times 10^{-11}$ M, and about $10^{-11}$ to about $10^{-12}$. In an embodiment, the antibody, or antigen binding fragment thereof binds $PGE_2$ and inhibits the binding of $PGE_2$ to at least one of its receptors in a cell surface-based receptor binding assay or in a radioimmunoassay-based receptor binding assay by about 70-100% at a concentration of 100 nM.

In an embodiment, the antibody is 19C9, 4F10, 15F10, K1B, K7H, K3A, L11, L21, 2B5-7.0, 2B5-8.0 or 2B5-9.0, or a variant thereof. In an embodiment, the variant is a humanized variant, such as Hu2B5.P1 or Hu2B5.P2.

In another aspect, the invention provides an isolated antibody, or antigen binding fragment thereof, that binds $PGE_2$ and inhibits paw edema by about 10%, 20%, 30%, 40%, 50%, 60%, 70%, 80%, 90% or 100% in a carrageenan-induced rodent paw edema model. In a particular embodiment, the antibody inhibits paw edema by greater than about 10% in a carrageenan induced rodent paw edema model In another aspect, the invention provides an isolated antibody, or antigen binding fragment thereof, that binds $PGE_2$ and inhibits paw swelling or mean arthritis score by about 10%, 20%, 30%, 40%, 50%, 60%, 70%, 80%, 90% or 100% in a rodent collagen induced arthritis model. In a particular embodiment, the antibody inhibits paw swelling or mean arthritis score by greater than 10% in a rodent collagen induced arthritis model.

In another aspect, the invention provides an isolated antibody, or antigen binding fragment thereof, that binds $PGE_2$ and inhibits paw edema by about 10%, 20%, 30%, 40%, 50%, 60%, 70%, 80%, 90% or 100% in a carrageenan-induced rodent paw edema model. In a particular embodiment, the antibody inhibits paw edema by greater than about 10% in a carrageenan induced rodent paw edema model In another aspect, the invention provides an isolated antibody, or antigen binding fragment thereof, that binds $PGE_2$ and inhibits paw swelling or mean arthritis score by about 10%, 20%, 30%, 40%, 50%, 60%, 70%, 80%, 90% or 100% in a rodent collagen induced arthritis model. In a particular embodiment, the antibody inhibits paw swelling or mean arthritis score by greater than 10% in a rodent collagen induced arthritis model.

In another embodiment, the binding protein of the invention has an off rate constant ($k_{off}$) to $PGE_2$ of at most about $10^{-3}$ s$^{-1}$; at most about $10^{-4}$ s$^{-1}$; at most about $10^{-5}$ s$^{-1}$; or at most about $10^{-6}$ s$^{-1}$, as measured by radioimmunoassay. Preferably, the binding protein of the invention has an off rate constant ($k_{off}$) to $PGE_2$ of about $10^{-3}$ s$^{-1}$ to about $10^{-4}$ s$^{-1}$; of about $10^{-4}$ s$^{-1}$ to about $10^{-5}$ s$^{-1}$; or of about $10^{-5}$ s$^{-1}$ to about $10^{-6}$ s$^{-1}$, as measured by radioimmunoassay.

In another embodiment, the binding protein of the invention has a dissociation constant ($K_D$) to $PGE_2$ determined by a radioimmunoassay of at most about $10^{-6}$ M; at most about $10^{-7}$ M; at most about $10^{-8}$ M; at most about $10^{-9}$ M; at most about $10^{-10}$ M; at most about $10^{-11}$ M; at most about $10^{-12}$ M; or at most $10^{-13}$ M. Preferably, the binding protein of the invention has a dissociation constant ($K_D$) to $PGE_2$ of about $10^{-7}$ M to about $10^{-8}$ M; of about $10^{-8}$ M to about $10^{-9}$ M; of about $10^{-9}$ M to about $10^{-10}$ M; of about $10^{-10}$ to about $10^{-11}$ M; of about $10^{-11}$ M to about $10^{-12}$ M; or of about $10^{-12}$ to M about $10^{-13}$ M. One aspect of the invention provides at least one PGE2 anti-idiotype antibody to at least one PGE2 binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

In another aspect, the invention provides an isolated antibody, or antigen binding fragment thereof, that binds prostaglandin $E_2$ and inhibits the binding of prostaglandin $E_2$ to at least one of E1, E2, E3, and E4 receptor in a cell surface-based receptor binding assay with an $IC_{50}$ selected from the group consisting of about $1\times10^{-6}$ to $1\times10^{-7}$ M, $1\times10^{-7}$ to $1\times10^{-8}$ M, $1\times10^{-8}$ to $1\times10^{-9}$ M, $10^{-9}$ to $10^{-10}$ M, $1\times10^{-10}$ to $1\times10^{-11}$ M and $10^{-11}$ to $10^{-12}$ M, or in an ELISA-based receptor binding assay with an $IC_{50}$ selected from the group consisting of about $1\times10^{-6}$ to $1\times10^{-7}$ M, $1\times10^{-7}$ to $1\times10^{-8}$ M, $1\times10^{-8}$ to $1\times10^{-9}$ M, $10^{-9}$ to $10^{-10}$ M, $1\times10^{-10}$ to $1\times10^{-11}$ M and $10^{-11}$ to $10^{-12}$ M.

In another embodiment, the antibody, or antigen binding fragment thereof binds prostaglandin $E_2$ and inhibits the binding of prostaglandin $E_2$ to at least one of the E1, E2, E3, and E4 receptors in a cell surface-based receptor binding assay or in a $^3H$-$PGE_2$ based radioimmunoassay using cells expressing or cell membrane preparation the expressing at least one of the E1, E2, E3, and E4 receptors by about 70-100% at a concentration of about 100 nM. In an embodiment, the antibody is selected from the group consisting of 19C9, 4F10, 15F10, K1B, K7H, K3A, L11, L21, 2B5-7.0, 2B5-8.0 and 2B5-9.0. In another embodiment, the antibody, or antigen binding fragment thereof, is capable of modulating a biological function of prostaglandin $E_2$, such as neutralizing prostaglandin $E_2$. The antibody, or antigen binding fragment thereof, is selected from the group consisting of an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, and a bispecific antibody. In an embodiment, the antibody, or antigen binding fragment thereof, is a humanized antibody. In another embodiment, the antibody is selected from the group consisting of Hu2B5.P1 and Hu2B5.P2. The invention also provides a pharmaceutical composition comprising the antibody, or antigen binding fragment thereof, and a pharmaceutically acceptable carrier. In an embodiment, the pharmaceutical composition further comprising at least one additional therapeutic agent for treating a disorder in which prostaglandin $E_2$ activity is detrimental.

In another aspect, the invention provides a method of generating an antibody, or fragment thereof, that binds to prostaglandin $E_2$ comprising the steps of immunizing a non-human animal with prostaglandin $E_2$-thyroglobulin, collecting a body fluid or organ comprising an anti-prostaglandin $E_2$ antibody, and isolating the anti-prostaglandin $E_2$ antibody.

In another aspect, the invention provides a humanized antibody comprising an antigen binding domain, capable of binding prostaglandin $E_2$, comprising at least one CDR region comprising an amino acid sequence selected from the group consisting of SEQ ID NOs: 54-59. In another embodiment, the invention provides a humanized antibody comprising an antigen binding domain comprising at least one CDR region comprising an amino acid sequence at least about 60%, at least about 65%, at least about 70%, at least about 75%, at least about 80%, at least about 85%, at least about 90%, at least about 95%, or at least about 98% homologous to an amino acid sequence selected from the group consisting of SEQ ID NOs: 54-59. In an embodiment, the humanized antibody comprises an amino acid sequence selected from the group consisting of SEQ ID NOs: 78, 79, 80, and 81.

In one aspect the invention binding protein capable of binding PGE2, said antigen binding domain comprising at least one CDR comprising an amino acid sequence selected from the group consisting of: CDR-H1: GYTFTKYWLG (SEQ ID NO: 54), CDR-H2: DIYPGYDYTHYNEKFKD (SEQ ID NO: 55), CDR-H3: SDGSSTY (SEQ ID NO: 56), CDR-L1: TSSQNIVHSNGNTYLE (SEQ ID NO: 57), CDR-L2: KVSNRFSG (SEQ ID NO: 58), CDR-L3: FQVSHVPYT (SEQ ID NO: 59).

In another embodiment, the invention provides a binding protein, or fragment thereof, comprising an antigen binding domain comprising at least one CDR comprising an amino acid sequence selected from the group consisting of SEQ ID NOs: 6, 7, 8, 10, 11, 12, 14, 15, 16, 18, 19, 20, 22, 23, 26, 27, 28, 30, 31, 32, 34, 35, 37, 38, and 39. In another embodiment, the binding protein, or fragment thereof, comprises an antigen binding domain comprising at least one VH region comprising an amino acid sequence selected from the group consisting of SEQ ID NOs: 5, 13, 21, 25, 33, 40, 42, and 44. In yet another embodiment, the binding protein, or fragment thereof, comprises an antigen binding domain comprising at least one VL region comprising an amino acid sequence selected from the group consisting of SEQ ID NOs: 9, 17, 24, 29, 36, 41, 43, and 45. In still another embodiment, the binding protein, or fragment thereof, comprises an antigen binding domain comprising at least one CDR region comprising an amino acid sequence selected from the group consisting of SEQ ID NOs: 54-59.

In an embodiment, the binding protein comprises at least 3 CDRs, for example, selected from a VH CDR set selected from the group consisting of SEQ ID NOs: 6, 7, and 8; SEQ ID NOs: 14, 15, and 16; SEQ ID NOs: 14, 22, and 23, SEQ ID NOs: 26, 27, and 28, and 32; SEQ ID NOs: 26, 34, and 35; and SEQ ID NOs: 54, 55, and 56. In another embodiment, the at least 3 CDRs are selected from a VL CDR set selected from the group consisting of SEQ ID NOs: 10, 11, and 12; SEQ ID NOs: 17, 18, and 19; SEQ ID NOs: 30, 31, and 32; SEQ ID NOs: 37, 38, and 39; SEQ ID NOs: 42, 43, and 44; and SEQ ID NOs: 57, 58, and 59. In still another embodiment, the at least 3 CDRs comprise a VH CDR set of amino acid sequences of SEQ ID NOs: 54, 55, and 56 and/or a VL CDR set of amino acid sequences of SEQ ID NOs: 57, 58, and 59.

In another embodiment, the binding protein comprises at least two variable domain CDR sets, for example, selected from a group consisting of SEQ ID NOs: 6, 7, 8 and SEQ ID NOs: 10, 11, 12; SEQ ID NOs: 14, 15, 16 and SEQ ID NOs: 18, 19, 20; SEQ ID NOs: 14, 22, 23 and SEQ ID NOs: 10, 11, 12; SEQ ID NOs: 26, 27, 28 and SEQ ID NOs: 30, 31, 32; and SEQ ID NOs: 26, 34, 35 and SEQ ID NOs: 37, 38, 39.

In another embodiment, the binding protein of the invention comprises two variable domains that have amino acid sequences selected from the group consisting of SEQ ID NO:5 and SEQ ID NO:9; SEQ ID NO:13 and SEQ ID NO:17; SEQ ID NO:21 and SEQ ID NO:24; SEQ ID NO:25 and SEQ ID NO:29; SEQ ID NO:33 and SEQ ID NO:36; SEQ ID NO:40 and SEQ ID NO:41; SEQ ID NO:42 and SEQ ID NO:43; and SEQ ID NO:44 and SEQ ID NO:45. In another embodiment, the two variable domains have amino acid sequences selected from the group consisting of SEQ ID NO:60 and SEQ ID NO:61; SEQ ID NO:62 and SEQ ID NO:63; SEQ ID NO:64 and SEQ ID NO:65; SEQ ID NO:66 and SEQ ID NO:67; SEQ ID NO:68 and SEQ ID NO:69; SEQ ID NO:70 and SEQ ID NO:71; SEQ ID NO:72 and SEQ ID NO:73; SEQ ID NO:74 and SEQ ID NO:75; and SEQ ID NO:76 and SEQ ID NO:77. In another embodiment, the two variable domains have amino acid sequences selected from the group consisting of SEQ ID NO:78 and SEQ ID NO:79; and SEQ ID NO:80 and SEQ ID NO:81.

In another aspect, the invention provides a humanized antibody, or fragment thereof, that binds to prostaglandin $E_2$, the humanized antibody comprising at least one VH region comprising an amino acid sequence selected from the group consisting of SEQ ID NOs: 60, 62, 64, 66, 68, 70, 72, 74, 76, 78, and 80. In another embodiment, the humanized antibody, or fragment thereof, comprises at least one VL region comprising an amino acid sequence selected from the group consisting of SEQ ID NOs: 61 63, 65, 67, 69, 71, 73, 75, 77, 79, and 81. In yet another embodiment, the at least one VH region or at least one VL region comprises human acceptor framework sequences that comprise at least one amino acid substitution, wherein the amino acid sequence of the framework sequence is at least 65% identical to the sequence of the human acceptor framework sequence. For example, the human acceptor framework may comprise at least one framework amino acid substitution at a key residue, the key residue selected from the group consisting of a residue adjacent to a CDR, a glycosylation site residue, a rare residue, a residue capable of interacting with prostaglandin $E_2$, a residue capable of interacting with a CDR, a canonical residue, a contact residue between heavy chain variable region and light chain variable region, a residue within a Vernier zone, and a residue in a region that overlaps between a Chothia-defined variable heavy chain CDR1 and a Kabat-defined first heavy chain framework.

In another embodiment the binding protein further comprises a human acceptor framework.

In one embodiment of the invention the human heavy chain and light chain acceptor sequences are selected from the sequences described in Table 7 and Table 8 (Example 4.2.1). Other human heavy chain and light chain acceptor sequences are well known in the art and are suitable for use with the invention. In an embodiment the binding protein is a CDR grafted antibody or antigen binding portion thereof capable of binding PGE2. In another embodiment, the binding protein is a humanized antibody or antigen binding portion thereof capable of binding PGE2. In an embodiment, the CDR grafted antibody or humanized antibody, or antigen binding portion thereof, comprise one or more CDRs disclosed herein, for example, three or more, four or more, five or more, or six or more CDRs. In another embodiment, the CDR grafted antibody or humanized antibody, or antigen binding portion thereof, comprises a human acceptor framework. The said human acceptor framework can be any acceptor framework of a human immunoglobulin. In a particular embodiment, the human acceptor framework is any one of the human acceptor frameworks disclosed herein. In an embodiment, the CDRs are incorporated into a human antibody variable domain of a human acceptor framework. In an embodiment, the human antibody variable domain is a consensus human variable domain. In another embodiment, the human acceptor framework comprises at least one Framework Region amino acid substitution at a key residue, wherein the key residue is selected from the group consisting of a residue adjacent to a CDR; a glycosylation site residue; a rare residue; a residue capable of interacting with PGE2; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. In an embodiment, the human acceptor framework human acceptor framework comprises at least one Framework Region amino acid substitution, wherein the amino acid sequence of the framework is at least 65% identical to the sequence of said human acceptor framework and comprises at least 70 amino acid residues identical to said human acceptor framework. In an embodiment, the framework region amino acid substitution at a key residue is selected from the group consisting of M (human) at position 48 to I (mouse), V (human) at position 68 to A (mouse), M (human) at position 70 to L (mouse), and T (human) at position 72 to V (mouse) in the heavy chain variable region; and I (human) at position 2 to V (mouse) and V (human) at position 3 to L (mouse) in the light chain variable region.

In another aspect, the invention provides an antibody construct comprising any one of the binding protein and a linker polypeptide and/or an immunoglobulin constant domain. In an embodiment, the antibody construct is selected from the group consisting of an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, and a bispecific antibody. In an embodiment, the antibody construct comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain. In an embodiment, the antibody construct comprises an immunoglobulin constant domain having an amino acid sequence selected from the group consisting of SEQ ID NO.:1; SEQ ID NO.:2; SEQ ID NO.:3; SEQ ID NO.:4; and SEQ ID NO.:5.

In another embodiment, the invention provides an anti-PGE2 antibody conjugate comprising an anti-PGE2 antibody construct and an agent selected from the group consisting of an immunoadhesion molecule, an imaging agent, a therapeutic agent, and a cytotoxic agent. In an embodiment, the agent is an imaging agent selected from the group consisting of a radiolabel, an enzyme, a fluorescent label, a luminescent label, a bioluminescent label, a magnetic label, and biotin. In another embodiment, the imaging agent is a radiolabel selected from the group consisting of $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm, for example. In another embodiment, the agent is a therapeutic or cytotoxic agent selected from the group consisting of an anti-metabolite, an alkylating agent, an antibiotic, a growth factor, a cytokine, an anti-angiogenic agent, an anti-mitotic agent, an anthracycline, a toxin, and an apoptotic agent.

In another embodiment, the binding protein is glycosylated. In a particular embodiment, the PGE2 binding protein has a human glycosylation pattern.

In another embodiment, the PGE2 binding protein, antibody construct or antibody conjugate is crystallized (e.g., exists as a crystal). In an embodiment, the crystal is a carrier-free pharmaceutical controlled release crystal. In another embodiment the crystallized binding protein, crystallized antibody construct or crystallized antibody conjugate has a greater half life in vivo than its soluble counterpart. In another embodiment the crystallized binding protein, crystallized antibody construct or crystallized antibody conjugate retains biological activity after crystallization.

One aspect of the invention pertains to a DVD binding protein comprising binding proteins capable of PGE2. Preferably, the DVD binding protein is capable of binding two PGE2 binding sites or binding PGE2 and a second target. The second target is selected from the group consisting of CSF1 (MCSF), CSF2 (GM-CSF), CSF3 (GCSF), FGF2, IFNα1, IFNβ1, IFNγ, histamine and histamine receptors, IL-1α, IL-1β, IL-2, IL-3, IL-4, IL-5, IL-6, IL-7, IL-8, IL-9, IL-10, IL-11, IL-12α, IL-12β, IL-14, IL-15, IL-16, IL-17, IL-18, IL-19, KITLG, PDGFB, IL-2Rβ, IL-4R, IL-5Rα, IL-8Rα, IL-8Rβ, IL-12Rβ1, IL-12Rβ2, IL-13Rα1, IL-13Rα2, IL-18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, LTBR, and Chitinase. In an embodiment, the DVD binding protein is capable of recognizing PGE2 and IL-1β, PGE2 and IL-9; PGE2 and IL-4; PGE2 and IL-5; PGE2 and IL-25; PGE2 and TARC; PGE2 and MDC; PGE2 and MIF; PGE2 and TGF-β; PGE2 and LHR agonist; PGE2 and CL25; PGE2 and SPRR2a; PGE2 and SPRR2b; or PGE2 and ADAM8. In an embodiment, the DVD binding protein is capable of binding PGE2 and TNFα.

In another aspect, the invention provides isolated nucleic acid, encoding a PGE2 binding protein, antibody construct or antibody conjugate. A further embodiment provides vectors comprising the isolated nucleic acids of the invention, wherein the vector is selected from the group consisting of pcDNA; pTT (Durocher et al., *Nucleic Acids Research* 2002, Vol 30, No. 2); pTT3 (pTT with additional multiple cloning site); pEFBOS (Mizushima, S. and Nagata, S., (1990) *Nucleic Acids Research* Vol 18, No. 17); pBV; pJV; pA2; and pBJ.

In another aspect, the invention provides host cells transformed with the vectors of the invention. In an embodiment, the host cell is a prokaryotic cell (e.g., *E. coli*). In another embodiment, the host cell is a eukaryotic cell, e.g., a protist cell, an animal cell, an avian cell, a plant cell, a fungal cell (e.g., a yeast cell such as, for example, *Saccharomyces cerevisiae*), a mammalian cell (e.g., a CHO, COS and HEK293), an insect cell (e.g., Sf9).

In another aspect, the invention provides a method of producing a protein that binds PGE2, comprising culturing any one of the host cells of the invention in a culture medium under conditions sufficient to produce a binding protein that binds PGE2. Another embodiment provides a binding protein produced according to the methods of the invention.

In another aspect, the invention provides a formulation that comprises a crystallized PGE2 binding protein, crystallized antibody construct or crystallized antibody conjugate, an ingredient, and/or at least one polymeric carrier. In an embodiment, the polymeric carrier is a polymer selected from the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, and a blend and/or copolymer thereof. In another embodiment, the ingredient is selected from the group consisting of albumin, sucrose, trehalose, lactitol, gelatin, hydroxypropyl-β-cyclodextrin, methoxypolyethylene glycol and polyethylene glycol.

In another aspect, the invention provides a method for treating a subject comprising the step of administering to the subject an effective amount of a PGE2 binding protein, antibody construct, conjugate, or composition. In an embodiment, the subject is a mammal, such as a human suffering from an inflammatory disease or other disorder described herein. In an embodiment, the invention provides a method of reducing, ameliorating, or preventing one or more symptoms of such a disease or disorder, such as a symptom of (a) rheumatoid arthritis, allergic arthritis, juvenile arthritis, ankylosing spondylitis and osteoarthritis; (b) certain illnesses induced by viruses, such as Guillain Barre syndrome, infectious mononucleosis, other viral lymphadenopathies and infections with herpes virus; (c) multiple sclerosis and other demyelinating diseases; (d) hematological disorders, such as hemolytic anemias and thrombocytopenias; (e) endocrinologic disorders, such as diabetes mellitus, Addison's disease, idiopathic hypoparathyroidism and chronic lymphocytic thyroiditis; (f) collagen disorders, such as systemic lupus erythematosus; and (g) disorders of reproduction such as amenorrhoea, infertility, recurrent abortions and eclampsia; and (h) tumors such as headneck tumor, lung cancer, gastric cancer, prostate cancer, pancreatic cancer etc; and (i) inflammatory bowel diseases than include Crohn's disease and ulcerative colitis; and (j) pain associated with osteoarthritis and other disorders; and (k) ocular disorders such as age-related macular degeneration (AMD).

In another aspect, the invention provides a pharmaceutical composition comprising a PGE2 binding protein, antibody, construct, conjugate, or composition and a pharmaceutically acceptable carrier. In an embodiment, the pharmaceutically acceptable carrier functions as an adjuvant useful to increase the absorption or dispersion of the binding protein. In an embodiment, the adjuvant is hyaluronidase. The pharmaceutical composition may further comprises at least one additional agent for diagnosing or treating a disorder in which PGE2 activity is detrimental, for example, an agent selected from the group consisting of a therapeutic agent, an imaging agent; a cytotoxic agent; an angiogenesis inhibitor (e.g., an anti-VEGF antibody or VEGF-trap); a kinase inhibitor (e.g., a KDR or TIE-2 inhibitor); a co-stimulation molecule blocker (e.g., an anti-B7.1, anti-B7.2, CTLA4-Ig, or anti-CD20); an adhesion molecule blocker (e.g., an anti-LFA-1, anti-E/L selectin, or small molecule inhibitor); an anti-cytokine antibody or functional fragment thereof (e.g., an anti-IL-18, anti-TNF, or anti-IL-6/cytokine receptor antibody); methotrexate; cyclosporine; rapamycin; FK506; a detectable label or reporter; a TNF antagonist; an anti-rheumatic; a muscle relaxant; a narcotic; a non-steroid anti-inflammatory drug (NSAID); an analgesic; an anesthetic; a sedative; a local anesthetic; a neuromuscular blocker; an antimicrobial; an antipsoriatic; a corticosteroid; an anabolic steroid; an erythropoietin; an immunization; an immunoglobulin; an immunosuppressive; a growth hormone; a hormone replacement drug; a radiopharmaceutical; an antidepressant; an antipsychotic; a stimulant; an asthma medication; a beta agonist; an inhaled steroid; an oral steroid; an epinephrine or analog thereof; a cytokine; and a cytokine antagonist.

In another aspect, the invention provides a method for inhibiting and/or reducing PGE2 activity comprising contacting PGE2 with a PGE2 binding protein such that PGE2 activity is inhibited and/or reduced. In an embodiment, the invention provides a method for inhibiting and/or reducing PGE2 activity in a subject suffering from a disorder in which PGE2 activity is detrimental, comprising administering to the subject a binding protein such that PGE2 activity in the subject is inhibited and/or reduced. In another embodiment, the method comprises administering to a subject a PGE2 binding protein of the invention such that treatment is achieved.

In another aspect, the invention provides a method of treating (e.g., curing, suppressing, ameliorating, delaying or preventing the onset of, or preventing recurrence or relapse of) or preventing a PGE2-associated disorder in a subject. The method includes: administering to the subject a PGE2 binding protein (particularly an antagonist), e.g., an anti-PGE2 antibody or fragment thereof, in an amount sufficient to treat or prevent the PGE2-associated disorder. The PGE2 antagonist, e.g., the anti-PGE2 antibody or fragment thereof, can be administered to the subject, alone or in combination with other therapeutic modalities.

In one embodiment, the subject is a mammal, e.g., a human suffering from one or more PGE2-associated disorders (e.g., characterized by excessive PGE2 levels or biosynthesis). In an embodiment. The invention provides methods for the treatment of inflammatory disorders and disorders of immunity in a subject, which disorders may be characterized by excessive $PGE_2$ biosynthesis, which methods comprise administering to the subject an effective amount of an antibody specific to $PGE_2$. Disorders that may be treated by the method according to the invention include autoimmune and inflammatory diseases and tumors in which excessive $PGE_2$ synthesis has been implicated. Such disorders include: (a) rheumatoid arthritis, allergic arthritis, juvenile arthritis, ankylosing spondylitis and osteoarthritis; (b) certain illnesses induced by viruses, such as Guillain Barre syndrome, infectious mononucleosis, other viral lymphadenopathies and infections with herpes virus; (c) multiple sclerosis and other demyelinating diseases; (d) hematological disorders, such as hemolytic anemias and thrombocytopenias; (e) endocrinologic disorders, such as diabetes mellitus, Addison's disease, idiopathic hypoparathyroidism and chronic lymphocytic thyroiditis; (f) collagen disorders, such as systemic lupus erythematosus; and (g) disorders of reproduction such as amenorrhoea, infertility, recurrent abortions and eclampsia; and (h) tumors such as headneck tumor, lung cancer, gastric cancer, prostate cancer, pancreatic cancer etc; and (i) inflammatory bowel diseases than include Crohn's disease and ulcerative colitis; and (j) pain associated with osteoarthritis and other disorders; and (k) ocular disorders such as age-related macular degeneration (AMD). In another aspect, this application provides a method for detecting the presence of PGE2 in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-PGE2 antibody or fragment thereof as described herein; and (ii) detecting formation of a complex between the anti-PGE2 antibody or fragment thereof, and the sample or the control sample, wherein a statistically significant change in the formation of the complex in the sample relative to the control sample is indicative of the presence of the PGE2 in the sample.

In yet another aspect, this application provides a method for detecting the presence of PGE2 in vivo (e.g., in vivo imaging in a subject). The subject method can be used to diagnose a disorder, e.g., a PGE2-associated disorder. The method includes: (i) administering the anti-PGE2 antibody or fragment thereof as described herein to a subject or a control subject under conditions that allow binding of the antibody or fragment to PGE2; and (ii) detecting formation of a complex between the antibody or fragment and PGE2, wherein a statistically significant change in the formation of the complex in the subject relative to the control subject is indicative of the presence of PGE2.

In another aspect, the binding proteins of the invention are useful for treating a disorder selected from the group consisting of arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, *yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, Acute coronary syndromes, Acute Idiopathic Polyneuritis, Acute Inflammatory Demyelinating Polyradiculoneuropathy, Acute ischemia, Adult Still's Disease, Alopecia greata, Anaphylaxis, Anti-Phospholipid Antibody Syndrome, Aplastic anemia, Arteriosclerosis, Atopic eczema, Atopic dermatitis, Autoimmune dermatitis, Autoimmune disorder associated with *Streptococcus* infection, Autoimmune Enteropathy, Autoimmune hearingloss, Autoimmune Lymphoproliferative Syndrome (ALPS), Autoimmune myocarditis, Autoimmune premature ovarian failure, Blepharitis, Bronchiectasis, Bullous pemphigoid, Cardiovascular Disease, Catastrophic Antiphospholipid Syndrome, Celiac Disease, Cervical Spondylosis, Chronic ischemia, Cicatricial pemphigoid, Clinically isolated Syndrome (CIS) with Risk for Multiple Sclerosis, Conjunctivitis, Childhood Onset Psychiatric Disorder, Chronic obstructive pulmonary disease (COPD), Dacryocystitis, dermatomyositis, Diabetic retinopathy, Diabetes mellitus, Disk herniation, Disk prolaps, Drug induced immune hemolytic anemia, Endocarditis, Endometriosis, endophthalmitis, Episcleritis, Erythema multiforme, erythema multiforme major, Gestational pemphigoid, Guillain-Barré Syndrome (GBS), hay fever, Hughes Syndrome, Idiopathic Parkinson's Disease, idiopathic interstitial pneumonia, IgE-mediated Allergy, Immune hemolytic anemia, Inclusion Body Myositis, Infectious ocular inflammatory disease, Inflammatory demyelinating disease, Inflammatory heart disease, Inflammatory kidney disease, IPF/UIP, Iritis, Keratitis, Keratojuntivitis sicca, Kussmaul disease or Kussmaul-Meier Disease, Landry's Paralysis, Langerhan's Cell Histiocytosis, Livedo reticularis, Macular Degeneration, Microscopic Polyangiitis, Morbus Bechterev, Motor Neuron Disorders, Mucous membrane pemphigoid, Multiple Organ failure, Myasthenia Gravis, Myelodysplastic Syndrome, Myocarditis, Nerve Root Disorders, Neuropathy, Non-A Non-B Hepatitis, Optic Neuritis, Osteolysis, Pauciarticular JRA, peripheral artery occlusive disease (PAOD), peripheral vascular disease (PVD), peripheral artery disease (PAD), Phlebitis, Polyarteritis nodosa (or periarteritis nodosa), Polychondritis, Polymyalgia Rheumatica, Poliosis, Polyarticular JRA, Polyendocrine Deficiency Syndrome, Polymyositis, polymyalgia rheumatica (PMR), Post-Pump Syndrome, primary parkinsonism, Prostatitis, Pure red cell aplasia, Primary Adrenal Insufficiency, Recurrent Neuromyelitis Optica, Restenosis, Rheumatic heart disease, SAPHO (synovitis, acne, pustulosis, hyperostosis, and osteitis), Scleroderma, Secondary Amyloidosis, Shock lung, Scleritis, Sciatica, Secondary Adrenal Insufficiency, Silicone associated connective tissue disease, Sneddon-Wilkinson Dermatosis, spondilitis ankylosans, Stevens-Johnson Syndrome (SJS), Systemic inflammatory response syndrome, Temporal arteritis, toxoplasmic retinitis, toxic epidermal necrolysis, Transverse myelitis, TRAPS (Tumor Necrosis Factor Receptor, Type 1 allergic reaction, Type II Diabetes, Urticaria, Usual interstitial pneumonia (UIP), Vasculitis, Vernal conjunctivitis, viral retinitis, Vogt-Koyanagi-Harada syndrome (VKH syndrome), Wet macular degeneration, and Wound healing.

In an embodiment, diseases that can be treated or diagnosed with the compositions and methods of the invention include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

The method comprises administering to the subject a PGE2 antagonist, e.g., a PGE2 antibody or a fragment thereof, in an amount sufficient to treat (e.g., reduce, ameliorate) or prevent one or more symptoms. The PGE2 antibody can be administered therapeutically or prophylactically, or both. The PGE2 antagonist, e.g., the anti-PGE2 antibody, or fragment thereof, can be administered to the subject, alone or in combination with other therapeutic modalities as described herein. Preferably, the subject is a mammal, e.g., a human suffering from a PGE2-associated disorder as described herein.

In another aspect, the binding proteins of the invention are useful for treating a disorder selected from the group consisting of Acute Lymphoblastic Leukemia, Acute Myeloid Leukemia, Adrenocortical Carcinoma, Anal Cancer, Appendix Cancer, Cerebellar Astrocytoma, Cerebral Astrocytoma, Basal Cell Carcinoma, Bile Duct Cancer, Extrahepatic, Bladder Cancer, Bone Cancer, Osteosarcoma/Malignant Fibrous Histiocytoma Brain Stem Glioma, Brain Tumor, Brain Stem Glioma, Cerebral strocytoma/Malignant Glioma, Ependymoma, Medulloblastoma, Supratentorial Primitive Neuroectodermal Tumors, Visual Pathway and Hypothalamic Glioma, Breast Cancer, Bronchial Adenomas/Carcinoids, Carcinoid Tumor, Carcinoid Tumor, Gastrointestinal Carcinoma of Unknown Primary, Central Nervous System Lymphoma, Primary Cerebellar Astrocytoma, Cervical Cancer, Chronic Lymphocytic Leukemia, Chronic Myelogenous Leukemia Chronic Myeloproliferative Disorders, Colon Cancer, Colorectal Cancer, Cutaneous T-Cell Lymphoma, Endometrial Cancer, Ependymoma, Esophageal Cancer, Ewing Family of Tumors, Extracranial Germ Cell Tumor, Extragonadal Germ Cell Tumor, Extrahepatic Bile Duct Cancer, Eye Cancer, Intraocular Melanoma Retinoblastoma, Gallbladder Cancer, Gastric (Stomach) Cancer, Gastrointestinal Carcinoid Tumor, Gastrointestinal Stromal Tumor (GIST), Extracranial Germ Cell Tumor, Extragonadal Germ Cell Tumor, Ovarian Germ Cell Tumor, Gestational Trophoblastic Tumor, Glioma, Brain Stem Glioma, Cerebral Astrocytoma Glioma, Childhood Visual Pathway and Hypothalamic Glioma, Hairy Cell Leukemia, Head and Neck Cancer, Hepatocellular (Liver) Cancer, Hodgkin Lymphoma, Hypopharyngeal Cancer, Intraocular Melanoma, Islet Cell Carcinoma (Endocrine Pancreas), Kaposi Sarcoma, Kidney (Renal Cell) Cancer, Laryngeal Cancer, Acute Lymphoblastic Leukemia, Acute Myeloid Leukemia, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Burkitt Lymphoma, Cutaneous T-Cell Lymphoma, Hodgkin Lymphoma, Non-Hodgkin Lymphoma, Primary Central Nervous System Lymphoma, Waldenström Macroglobulinemia, Malignant Fibrous Histiocytoma of Bone/Osteosarcoma, Medulloblastoma, Melanoma, Intraocular (Eye) Melanoma, Merkel Cell Carcinoma, Malignant Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Chronic Myeloid Leukemia, Multiple Myeloma, Myeloproliferative Disorders, Nasal Cavity and Paranasal Sinus Cancer, Nasopharyngeal Cancer, Neuroblastoma, Oral Cancer, Oral Cavity Cancer, Lip and Oropharyngeal Cancer, Osteosarcoma/Malignant Fibrous Histiocytoma of Bone, Ovarian Cancer, Ovarian Epithelial Cancer, Ovarian Germ Cell Tumor, Ovarian Low Malignant Potential Tumor, Pancreatic Cancer, Islet Cell Pancreatic Cancer, Paranasal Sinus and Nasal Cavity Cancer, Parathyroid Cancer, Penile Cancer, Pharyngeal Cancer, Pheochromocytoma, Pineoblastoma and Supratentorial Primitive Neuroectodermal Tumors, Pituitary Tumor, Plasma Cell Neoplasm/Multiple Myeloma, Pleuropulmonary Blastoma, Prostate Cancer, Rectal Cancer, Renal Cell (Kidney) Cancer, Renal Pelvis and Ureter, Transitional Cell Cancer, Retinoblastoma, Salivary Gland Cancer, Sarcoma, Ewing Family of Tumors, Kaposi Sarcoma, Soft Tissue Sarcoma, Uterine Sarcoma, Sézary Syndrome, Skin Cancer (Nonmelanoma), Skin Cancer (Melanoma), Merkel Cell Skin Carcinoma, Small Intestine Cancer, Squamous Cell Carcinoma, Metastatic Squamous Neck Cancer with Occult Primary, Stomach (Gastric) Cancer, Supratentorial Primitive Neuroectodermal Tumors, Cutaneous T-Cell Lymphoma, Testicular Cancer, Throat Cancer, Thymoma, Thymoma and Thymic Carcinoma, Thyroid Cancer, Transitional Cell Cancer of the Renal Pelvis and Ureter, Gestational Trophoblastic Tumor, Ureter and Renal Pelvis, Transitional Cell Cancer, Urethral Cancer, Uterine Cancer, Endometrial Uterine Sarcoma, Vaginal Cancer, Visual Pathway and Hypothalamic Glioma, Vulvar Cancer, Waldenström Macroglobulinemia, Wilms Tumor.

In another aspect the invention provides a method of treating a patient suffering from a disorder in which PGE2 is detrimental comprising the step of administering any one of the binding proteins disclosed above before, concurrently, or after the administration of a second agent, as discussed above. In an embodiment the second therapeutic agent that can be coadministered and/or coformulated with one or more $PGE_2$ antagonists, (e.g., anti-PGE2 antibodies or fragments thereof) include, but are not limited to, one or more of: inhaled steroids; oral steroids; beta-agonists, e.g., short-acting or long-acting beta-agonists; antagonists of leukotrienes or leukotriene receptors; combination drugs such as ADVAIR™; IgE inhibitors, e.g., anti-IgE antibodies (e.g., XOLAIR™); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be coadministered and/or coformulated with one or more anti-PGE2 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL™)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others. Additional second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β, monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, and TGFβ.

In a particular embodiment, the invention provides a method of treating a patient suffering from a disorder in which prostaglandin $E_2$ is detrimental, the method comprising the step of administering a binding protein of the invention before, concurrently, or after the administration of a second agent, wherein the second agent is selected from the group consisting of the drugs that currently are used for the treatment of various human diseases and disorders. A list of such drugs is available from the internet. This list is updated frequently to reflect the state-of-art for the treatment of various human diseases. A list of such drugs is also available from the most updated drug guide (Complete Guide to Prescription & Nonprescription Drugs 2008. by H. Winter Griffith, Stephen Moore, ISBN-13: 978-0399533723). The anti-PGE$_2$ binding protein can be combined with any of the therapies in the above list for a particular disease conditions. For example, the anti-PGE$_2$ binding protein can be combined with one or more agents for the treatment of rheumatoid arthritis and juvenile rheumatoid arthritis. Examples of these agents include, but are not limited to, methotrexate, leflunomide, low doses of corticosteroids such as prednisone or cortisone, antimalarial medications such as hydroxychloroquine, gold, sulfasalazine, penicillamine, cyclophosphamide, cyclosporine, minocycline, Acetaminophen, aspirin, ibuprofen, naproxen, celecoxib, Infliximab, etanercept, adalimumab, abatacept, rituximab, anakinra and other new biologic agents and oral delivery agents targeting IL-6, IL-6R, IL-17, IL-18, IL-23, B7.1/B7.2. The anti-PGE$_2$ binding protein can be combined with one or more agents for the treatment of osteoarthritis. Example of these agents include but are not limited to acetaminophen, aspirin, ibuprofen, naproxen, celecoxib, steroids, artificial joint fluid such as synvisc™, and hyalgan™. The anti-PGE$_2$ binding protein can be combined with one or more agents for the treatment of Crohn's disease. Examples of these agents include but are not limited to adalimumab, azasan™, asacol™, azathioprine, azulfidine™, budesonide, entocort™, flagyl™, imuran™, infliximab, mercaptopurine, metronidazole, protostat, purinethol™, remicade™, and sulfasalazine. The anti-PGE$_2$ binding protein can be combined with one or more agents for the treatment of ankylosing spondylitis. Examples of these agents include but are not limited to acetocot, acetylsalicylic acid, acuprin 81, adalimumab, Aleve™, amcort, Anaprox™, Aristocort™, aspirin, aspirtab, Azmacort™, Bufferin™, buffex, Cataflam™, Celebrex™, Clinoril™, cortisone, diclofenac, Dipentum™, Easprin™, etanercept, Indocin™, indomethacin, infliximab, naproxen, Remicade™, triamcinolone, and voltaren™. The anti-PGE$_2$ binding protein can be combined with one or more agents for the treatment of multiple sclerosis. Examples of these agents include but are not limited to Avonex™, Azasan™, Azathioprine, Betaseron™, Bubbli-Pred™, Copaxone™, Cotolone, Glatiramer, Imuran™, Interferon Beta-1a, Interferon Beta-1b Solution, Key-Pred, Key-Pred SP, Mitoxantrone, Natalizumab, Novantrone™, Orapred™, Orapred ODT™, Pediapred™, Pred-Ject-50, Predacort 50, Predalone 50, Predate-50, Prednisolone, Prelone™, Rebif™, and Tysabri™. The anti-PGE$_2$ binding protein can be combined with one or more agents or treatment procedures for the treatment of various human cancers and malignancies. Besides a list available from the internet and from the most updated drug guide (Complete Guide to Prescription & Nonpresciption Drugs 2008. by H. Winter Griffith, Stephen Moore, ISBN-13: 978-0399533723), NCI also maintains drug information about certain drugs that are approved by the U.S. Food and Drug Administration (FDA) for the treatment of cancer or conditions related to cancer. Examples of these agents include but are not limited to Abraxane™, Adriamycin, Adrucil™, Aldara™, Alemtuzumab, Alimta™, Aminolevulinic Acid, Anastrozole, Aprepitant, Arimidex™, Aromasin™, Arranon™, Arsenic Trioxide, Avastin™(Bevacizumab), Azacitidine, Bevacizumab, Bexarotene, Bortezomib, Campath™ (Alemtuzumab), Camptosar™(Irinotecan Hydrochloride), Capecitabine, Carboplatin, Cetuximab, Cisplatin, Clafen (Cyclophosphamide), Clofarabine, Clofarex (Clofarabine), Clolar™(Clofarabine), Cyclophosphamide, Cytarabine, Cytosar-U (Cytarabine), Cytoxan (Cyclophosphamide), Dacogen™(Decitabine), Dasatinib, Decitabine, DepoCyt™ (Liposomal Cytarabine), DepoFoam™(Liposomal Cytarabine), Dexrazoxane Hydrochloride, Docetaxel, Doxil™ (Doxorubicin Hydrochloride Liposome), Doxorubicin Hydrochloride, Doxorubicin Hydrochloride Liposome, Dox-SL (Doxorubicin Hydrochloride Liposome), Efudex™ (Fluorouracil), Ellence™(Epirubicin Hydrochloride), Eloxatin ™(Oxaliplatin), Emend™(Aprepitant), Epirubicin Hydrochloride, Erbitux™(Cetuximab), Erlotinib Hydrochloride, Evacet (Doxorubicin Hydrochloride Liposome), Evista™(Raloxifene Hydrochloride), Exemestane, Faslodex (Fulvestrant), Femara™(Letrozole), Fluoroplex™(Fluorouracil), Fluorouracil, Fulvestrant, Gefitinib, Gemcitabine Hydrochloride, Gemtuzumab Ozogamicin, Gemzar™(Gemcitabine Hydrochloride), Gleevec™(Imatinib Mesylate), Herceptin™(Trastuzumab), Hycamtin™(Topotecan Hydrochloride), Imatinib Mesylate, Imiquimod, Iressa™(Gefitinib), Irinotecan Hydrochloride, Ixabepilone, Ixempra™ (Ixabepilone), Keoxifene (Raloxifene Hydrochloride), Kepivance™(Palifermin), Lapatinib Ditosylate, Lenalidomide, Letrozole, Levulan™(Aminolevulinic Acid), Lipo-Dox™(Doxorubicin Hydrochloride Liposome), Liposomal Cytarabine, Methazolastone (Temozolomide), Mylosar (Azacitidine), Mylotarg™(Gemtuzumab Ozogamicin), Nanoparticle Paclitaxel (Paclitaxel Albumin-stabilized Nanoparticle Formulation), Nelarabine, Neosar™(Cyclophosphamide), Nexavar™(Sorafenib Tosylate), Nilotinib, Nolvadex (Tamoxifen Citrate), Oncaspar™(Pegaspargase), Oxaliplatin, Paclitaxel, Paclitaxel Albumin-stabilized Nanoparticle Formulation, Palifermin, Panitumumab, Paraplat (Carboplatin), Paraplatin™(Carboplatin), Pegaspargase, Pemetrexed Disodium, Platinol-AQ (Cisplatin), Platinol™ (Cisplatin), Raloxifene Hydrochloride, Revlimid (Lenalidomide), Rituxan™(Rituximab), Rituximab, Sclerosol Intrapleural Aerosol (Talc), Sorafenib Tosylate, Sprycel™ (Dasatinib), Sterile Talc Powder (Talc), Steritalc™(Talc), Sunitinib Malate, Sutent™(Sunitinib Malate), Synovir (Thalidomide), Talc, Tamoxifen Citrate, Tarabine PFS (Cytarabine), Tarceva™(Erlotinib Hydrochloride), Targretin™(Bexarotene), Tasigna™(Nilotinib), Taxol™(Paclitaxel), Taxotere™(Docetaxel), Temodar™(Temozolomide), Temozolomide, Temsirolimus, Thalomid™(Thalidomide), Thalidomide, Totect™(Dexrazoxane Hydrochloride), Topotecan Hydrochloride, Torisel™(Temsirolimus), Trastuzumab, Trisenox™(Arsenic Trioxide), Tykerb™(Lapatinib Ditosylate), Vectibix™(Panitumumab), Velcade™(Bortezomib), Vidaza™(Azacitidine), Vorinostat, Xeloda™(Capecitabine), Zinecard™(Dexrazoxane Hydrochloride), Zoledronic Acid, Zolinza™(Vorinostat), and Zometa™(Zoledronic Acid).

In a preferred embodiment the PGE2 binding protein pharmaceutical compositions disclosed above are administered to the subject by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which:

FIG. 8 provides alignment of VH regions (SEQ ID NOs 40, 42, 44 and 82, respectively, in order of appearance) and VL regions (SEQ ID NOs 41, 43, 45 and 83, respectively, in order of appearance) of anti-PGE$_2$ antibodies 2B5.7, 2B5.8 and 2B5.9 as described in Example 3.

DETAILED DESCRIPTION OF THE INVENTION

Figure 1:
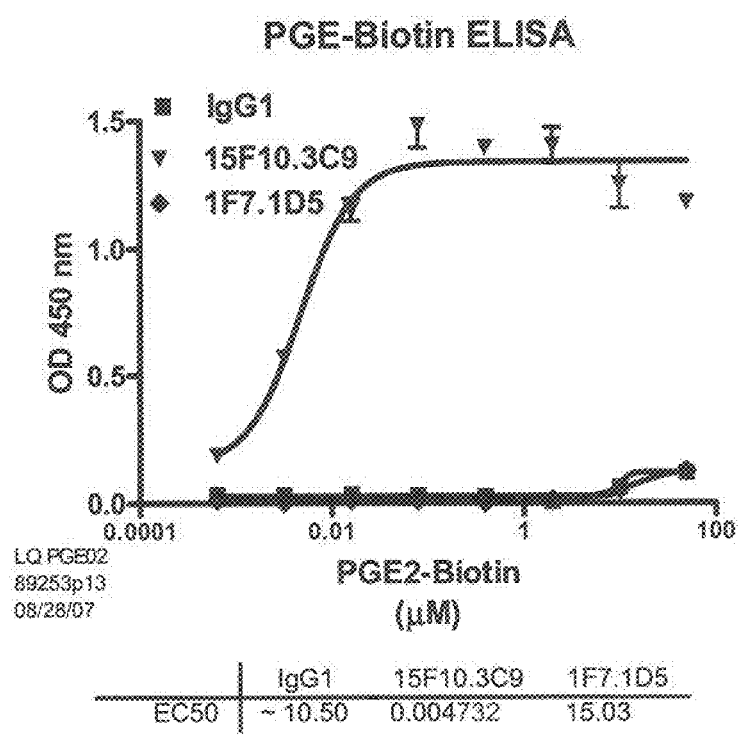
FIG. 1 provides measurement of the binding of two hybridoma derived mAbs 15F10.3C9 and 1F7.1D5 to Biotin-PGE$_2$ in an ELISA described in Example 1.1.A.

This invention pertains to Prostaglandin E2 (PGE$_2$) binding proteins, particularly anti-PGE$_2$ antibodies, or antigen-binding fragments thereof, that bind PGE$_2$. Various aspects of the invention relate to antibodies and antibody fragments, and pharmaceutical compositions thereof, as well as nucleic acids, recombinant expression vectors and host cells for making such antibodies and fragments. Methods of using the antibodies of the invention to detect PGE$_2$, to inhibit one or more PGE$_2$ activities, either in vitro or in vivo; and to regulate gene expression are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The terms "Prostaglandin E2" (abbreviated herein as PGE$_2$), as used herein, refers to the prostaglandin having the following structure or a variant thereof that retains some or all PGE$_2$ activities:

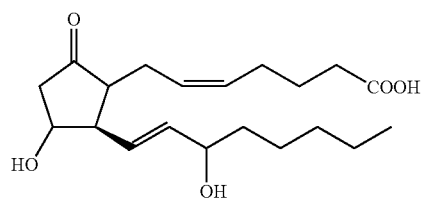 [SMILES: CCCCCC(O)/C=C/[C@H]1C(O)CC(=O)C1C/C=C\CCCC(=O)O]

"Biological activity" as used herein, refers to inherent biological properties of the cytokine. Biological properties of PGE$_2$ include but are not limited to binding to a PGE$_2$ receptor.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" or "antigen binding fragment" of an antibody (or simply "antibody portion"), as used herein, refers to one or more fragments of an antibody that retain the ability to specifically bind to an antigen (e.g., $PGE_2$). The antigen-binding function of an antibody can be performed by fragments of a full-length antibody. Such antibody embodiments may also have bispecific, dual specific, or multispecific formats, specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144A1), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag, New York, pp. 790 (ISBN 3-540-41354-5).

The term "antibody construct" as used herein refers to a polypeptide comprising one or more antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art and are represented in Table 1.

TABLE 1

Sequence Of Human IgG Heavy Chain Constant Domain And Light Chain Constant Domain

| Protein | Sequence Identifier | Sequence 12345678901234567890123456789012 |
|---|---|---|
| Ig gamma-1 constant region | SEQ ID NO.: 1 | ASTKGPSVFFLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |

TABLE 1-continued

Sequence Of Human IgG Heavy Chain Constant
Domain And Light Chain Constant Domain

| Protein | Sequence Identifier | Sequence 123456789012345678901234567890123 |
|---|---|---|
| Ig gamma-1 constant region mutant | SEQ ID NO.: 2 | ASTKGPSVFPLAPSSKSTSGGTAALGCLVKDY FPEPVTVSWNSGALTSGVHTFPAVLQSSGLYS LSSVVTVPSSSLGTQTYTCNVNHKPSNTKVDK KVEPKSCDKTHTCPPCPAPEAAGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig Kappa constant region | SEQ ID NO.: 3 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| Ig Lambda constant region | SEQ ID NO.: 4 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds $PGE_2$ is substantially free of antibodies that specifically bind antigens other than $PGE_2$). An isolated antibody that specifically binds $PGE_2$ may, however, have cross-reactivity to other antigens, such as Prostaglandin E1 ($PGE_1$) molecules. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) *Nucl. Acids Res.* 20:6287-6295; Kellermann S-A., and Green L. L. (2002) *Current Opinion in Biotechnology* 13:593-597; Little M. et al. (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding $PGE_2$ which can be generated using techniques well known in the art, such as, but not limited to, using human Ig phage libraries such as those disclosed in Jermutus et al., PCT publication No. WO 2005/007699 A2.

The term "chimeric antibody" refers to antibodies which comprise heavy and/or light chain variable region sequences from one species and constant region sequences from another species, such as antibodies having murine heavy and light chain variable regions linked to human constant regions.

The term "CDR-grafted antibody" refers to antibodies which comprise heavy and/or light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-$PGE_2$ antibodies and antigen binding portions are provided. Such antibodies were generated by obtaining murine anti-$PGE_2$ monoclonal antibodies using traditional hybridoma technology followed by humanization using in vitro genetic engineering, such as those disclosed in Kasaian et al PCT publication No. WO 2005/123126 A2.

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, at least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al., J. Mol. Biol. 196:901-907 (1987); Chothia et al., J. Mol. Biol. 227: 799 (1992). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represent two or more of the four sub-regions constituting a framework region. See Tables 5 and 6 for exemplary FR sequences.

As used herein, the term "germline antibody gene" or "germline antibody gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with an antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (e.g., Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See, e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992) J. Mol. Biol. 224:487-499). Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVD binding proteins may be monospecific, i.e., capable of binding one antigen or multispecific, i.e., capable of binding two or more antigens. DVD binding proteins comprising two heavy chain DVD polypeptides and two light chain DVD polypeptides are referred to a DVD-Ig™. Each half of a DVD-Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

As used herein, the term "neutralizing" refers to neutralization of biological activity of a cytokine or a lipid metabolite when a binding protein specifically binds the cytokine or a lipid metabolite. Preferably a neutralizing binding protein is a neutralizing antibody whose binding to $PGE_2$ results in inhibition of a biological activity of $PGE_2$. Preferably the neutralizing binding protein binds $PGE_2$ and reduces a biological activity of $PGE_2$ by at least about 10%, 20%, 40%, 60%, 80%, 85% or more. Inhibition of a biological activity of $PGE_2$ by a neutralizing binding protein can be assessed by measuring one or more indicators of $PGE_2$ biological activity well known in the art. For example inhibition of $PGE_2$ induced calcium influx by EP4 assay using HEK293 cells over-expressing EP4 receptor (see Example 1.1.C 1).

The term "activity" includes activities such as the binding specificity/affinity of an antibody for an antigen, for example, an anti-PGE$_2$ antibody that binds to an PGE$_2$ antigen and/or the neutralizing potency of an antibody, for example, an anti-PGE$_2$ antibody whose binding to PGE$_2$ inhibits the biological activity of PGE$_2$, e.g., for example inhibition of PGE$_2$ induced calcium influx by EP4 assay using HEK293 cells over-expressing EP4 receptor (see Example 1.1.C 1).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. An epitope is a region of an antigen that is bound by an antibody. In certain embodiments, an antibody specifically binds an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example, using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnsson, B., et al. (1991) *Anal. Biochem.* 198:268-277.

The term "k$_{on}$", as used herein, is intended to refer to the on rate constant for association of an antibody to an antigen to form an antibody/antigen complex as is known in the art.

The term "k$_{off}$", as used herein, is intended to refer to the off rate constant for dissociation of an antibody from an antibody/antigen complex as is known in the art.

The term "K$_D$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors); enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ed., pp. 20 1-16, Oxford University Press, New York, N.Y., (1999).

One embodiment provides a composition for the release of a binding protein wherein the composition comprises a formulation which in turn comprises a crystallized binding protein, crystallized antibody construct or crystallized antibody conjugate as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature, or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated.

Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present invention may be expressed, and purified using expression vectors and host cells known in the art, including expression cassettes, vectors, recombinant host cells, and methods for the recombinant expression and proteolytic processing of recombinant polyproteins and pre-proteins from a single open reading frame (e.g., WO 2007/014162).

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic cells, eukaryotic cells, insect cells, or cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *S. cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)).

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of $PGE_2$). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity $PGE_2$). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, $PGE_2$ or polypeptides, nucleic acids, carbohydrates, or any other molecules that bind to $PGE_2$.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of $PGE_2$. Antagonists and inhibitors of $PGE_2$ may include, but are not limited to, proteins, nucleic acids, carbohydrates, or any other molecules, which bind to $PGE_2$.

The term "inhibit binding to the receptor" refers to the ability of the binding protein to prevent the binding of $PGE_2$ to one or more of its receptors. Such inhibition of binding to the receptor would result in diminishing or abolishing the biological activity mediated by binding of $PGE_2$ to its receptor or receptors.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes, and spleen.

In a preferred embodiment the binding protein is a CDR grafted antibody or antigen binding portion thereof capable of binding $PGE_2$. Preferably the CDR grafted antibody or antigen binding portion thereof comprise one or more CDRs from 2B5-7.0, or 2B5-8.0 or 2B5-9.0 disclosed above. Preferably the CDR grafted antibody or antigen binding portion thereof comprises a human acceptor framework. More preferably the human acceptor framework is any one of the human acceptor frameworks having >60% homology to mouse antibody frameworks of 2B5-7.0, or 2B5-8.0 or 2B5-9.0.

In a preferred embodiment the binding protein is a humanized antibody or antigen binding portion thereof capable of binding $PGE_2$. Preferably the humanized antibody or antigen binding portion thereof comprises one or more CDRs disclosed above incorporated into a human antibody variable domain of a human acceptor framework. Preferably the human antibody variable domain is a consensus human variable domain. More preferably the human acceptor framework comprises at least one Framework Region amino acid substitution at a key residue, wherein the key residue is selected from the group consisting of a residue adjacent to a CDR; a glycosylation site residue; a rare residue; a residue capable of interacting with $PGE_2$; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. Preferably the human acceptor framework human acceptor framework comprises at least one Framework Region amino acid substitution, wherein the amino acid sequence of the framework is at least 65% identical to the sequence of the human acceptor framework and comprises at least 70 amino acid residues identical to the human acceptor framework.

In an embodiment, the humanized antibody, or antigen binding portion thereof, comprises three or more CDRs disclosed above. In a certain embodiment, the humanized antibody, or antigen binding portion, thereof comprises six CDRs disclosed above.

One embodiment of the invention provides an antibody construct comprising any one of the binding proteins disclosed above and a linker polypeptide or an immunoglobulin. In a preferred embodiment the antibody construct is selected from the group consisting of an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, a DVD-Ig™ and a bispecific antibody. In a preferred embodiment the antibody construct comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain. In another embodiment the invention provides an antibody conjugate comprising an the antibody construct disclosed above and an agent an agent selected from the group consisting of; an immunoadhension molecule, an imaging agent, a therapeutic agent, and a cytotoxic agent. In a preferred embodiment the imaging agent selected from the group consisting of a radiolabel, an enzyme, a fluorescent label, a luminescent label, a bioluminescent label, a magnetic label, and biotin. More preferably the imaging agent is a radiolabel selected from the group consisting of: $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$. In a preferred embodiment the therapeutic or cytotoxic agent is selected from the group consisting of an anti-metabolite, an alkylating agent, an antibiotic, a growth factor, a cytokine, an anti-angiogenic agent, an anti-mitotic agent, an anthracycline, toxin, and an apoptotic agent.

In another embodiment the antibody construct is glycosylated. Preferably the glycosylation is a human glycosylation pattern.

In another embodiment, the binding protein, antibody construct or antibody conjugate disclosed above is a crystal. Preferably, the crystal is a carrier-free pharmaceutical controlled release crystal. In a preferred embodiment the crystallized binding protein, crystallized antibody construct or crystallized antibody conjugate has a greater half life in vivo than its soluble counterpart. In another preferred embodiment the crystallized binding protein, crystallized antibody construct or crystallized antibody conjugate retains biological activity after crystallization.

One aspect of the invention pertains to an isolated nucleic acid encoding any one of the binding proteins, antibody constructs or antibody conjugates disclosed above. A further embodiment provides a vector comprising the isolated nucleic acid disclosed above wherein the vector is selected from the group consisting of pcDNA; pTT (Durocher et al., *Nucleic Acids Research* 2002, Vol 30, No. 2); pTT3 (pTT with additional multiple cloning site; pEFBOS (Mizushima, S, and Nagata, S. (1990) *Nucleic acids Research* Vol 18, No. 17); pBV; pJV; pA2; and pBJ.

In another aspect a host cell is transformed with the vector disclosed above. Preferably the host cell is a prokaryotic cell.

More preferably the host cell is *E. coli*. In another embodiment the host cell is a eukaryotic cell. Preferably the eukaryotic cell is selected from the group consisting of protist cell, animal cell, plant cell and fungal cell. More preferably the host cell is a mammalian cell including, but not limited to, CHO, HEK293, and COS; or a fungal cell such as *Saccharomyces cerevisiae*; or an insect cell such as Sf9.

Another aspect of the invention provides a method of producing a binding protein that binds $PGE_2$, comprising culturing any one of the host cells disclosed above in a culture medium under conditions sufficient to produce a binding protein that binds $PGE_2$. Another embodiment provides a binding protein produced according to the method disclosed above.

The invention also provides a pharmaceutical composition comprising a binding protein, antibody construct or antibody conjugate as disclosed above and a pharmaceutically acceptable carrier. In a further embodiment the pharmaceutical composition comprises at least one additional therapeutic agent for treating a disorder in which $PGE_2$ activity is detrimental. Preferably the additional agent is selected from the group consisting of a therapeutic agent, an imaging agent, a cytotoxic agent, an angiogenesis inhibitor (including but not limited to anti-VEGF antibodies or VEGF-trap); a kinase inhibitor (including but not limited to KDR and TIE-2 inhibitors); a co-stimulation molecule blocker (including but not limited to anti-B7.1, anti-B7.2, CTLA4-Ig, anti-CD20); an adhesion molecule blocker (including but not limited to anti-LFA-1 Abs, anti-E/L selectin Abs, small molecule inhibitors); an anti-cytokine antibody or functional fragment thereof (including but not limited to anti-IL-18, anti-TNF, anti-IL-6/cytokine receptor antibody); methotrexate; cyclosporin; rapamycin; FK506; a detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect, the invention provides a method for inhibiting $PGE_2$ activity comprising contacting $PGE_2$ with a binding protein disclosed above such that $PGE_2$ activity is inhibited. In a related aspect the invention provides a method for inhibiting $PGE_2$ activity in a human subject suffering from a disorder in which $PGE_2$ activity is detrimental, comprising administering to the human subject a binding protein disclosed above such that $PGE_2$ activity in the human subject is inhibited and treatment is achieved.

In another aspect, the invention provides a method of treating (e.g., curing, suppressing, ameliorating, delaying or preventing the onset of, or preventing recurrence or relapse of) or preventing a $PGE_2$-associated disorder, in a subject. The method includes: administering to the subject a $PGE_2$ binding agent (particularly an antagonist), e.g., an anti-$PGE_2$ antibody or fragment thereof as described herein, in an amount sufficient to treat or prevent the $PGE_2$-associated disorder. The $PGE_2$ antagonist, e.g., the anti-$PGE_2$ antibody or fragment thereof, can be administered to the subject, alone or in combination with other therapeutic modalities as described herein.

In one embodiment, the invention providing methods and compositions for treating (e.g., reducing, ameliorating) or preventing one or more symptoms in a mammalian subject, e.g., a human suffering from one or more $PGE_2$-associated disorders, including, e.g., autoimmune and inflammatory diseases and tumors in which excessive $PGE_2$ synthesis has been implicated. Such disorders include: (a) rheumatoid and allergic arthritis; (b) certain illnesses induced by viruses, such as Guillain Barre syndrome, infectious mononucleosis, other viral lymphadenopathies and infections with herpes virus; (c) multiple sclerosis and other demyelinating diseases; (d) hematological disorders, such as hemolytic anemias and thrombocytopenias; (e) endocrinologic disorders, such as diabetes mellitus, Addison's disease, idiopathic hypoparathyroidism and chronic lymphocytic thyroiditis; (f) collagen disorders, such as systemic lupus erythematosus; and (g) disorders of reproduction such as amenorrhoea, infertility, recurrent abortions and eclampsia; and (h) tumors such as headneck tumor, lung cancer, gastric cancer, prostate cancer, pancreatic cancer etc., and (i) gastrointestinal organ disorders (e.g., inflammatory bowel diseases (IBD), such as ulcerative colitis and/or Crohn's disease); and (j) pain disorders such as pain related with osteoarthritis and other disorders; and (k) ocular disorders such as age-related mascular degeneration (AMD). Accordingly, the disclosure includes the use of a $PGE_2$ binding agent (such as an anti-$PGE_2$ antibody or fragment thereof) for a treatment and the use of a $PGE_2$ binding agent (such as an anti-$PGE_2$ antibody or fragment thereof) for preparing a medicament for a treatment.

The method comprises administering to the subject a $PGE_2$ antagonist, e.g., a $PGE_2$ antibody or a fragment thereof, in an amount sufficient to treat (e.g., reduce, ameliorate) or prevent one or more symptoms. The $PGE_2$ antibody can be administered therapeutically or prophylactically, or both. The $PGE_2$ antagonist, e.g., the anti-$PGE_2$ antibody, or fragment thereof, can be administered to the subject, alone or in combination with other therapeutic modalities as described herein. Preferably, the subject is a mammal, e.g., a human suffering from a $PGE_2$-associated disorder as described herein.

In another aspect, this application provides a method for detecting the presence of $PGE_2$ in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-$PGE_2$ antibody or fragment thereof as described herein; and (ii) detecting formation of a complex between the anti-$PGE_2$ antibody or fragment thereof, and the sample or the control sample, wherein a statistically significant change in the formation of the complex in the sample relative to the control sample is indicative of the presence of the $PGE_2$ in the sample.

In another aspect the invention provides a method of treating a patient suffering from a disorder in which $PGE_2$ is detrimental comprising the step of administering any one of the binding proteins disclosed above before, concurrent, or after the administration of a second agent, as discussed above. In a preferred embodiment the additional therapeutic agent that can be coadministered and/or coformulated with one or more $PGE_2$ antagonists, (e.g., anti-$PGE_2$ antibodies or fragments thereof) include, but are not limited to, one or more of MTX; oral steroids; metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, and TGF β.

In a preferred embodiment the pharmaceutical compositions disclosed above are administered to the subject by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

One aspect of the invention provides at least one $PGE_2$ anti-idiotype antibody to at least one $PGE_2$ binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

I. Antibodies that Bind Prostaglandin E2

In invention provides murine monoclonal antibodies, or antigen-binding portions thereof, that bind to $PGE_2$ with high affinity, a slow off rate and high neutralizing capacity. The invention also provides chimeric antibodies that bind $PGE_2$. The invention also provides humanized antibodies, or antigen-binding portions thereof, that bind $PGE_2$. Preferably, the antibodies, or portions thereof, are isolated antibodies. Preferably, the antibodies of the invention are neutralizing human anti-$PGE_2$ and/or human anti-$PGE_2$ antibodies.

A. Method of Making Anti Prostaglandin $E_2$ Antibodies

The antibodies and antibody fragments of the invention may be generated by any art-known method, such as, for example, hybridoma, microbe (e.g., phage, bacteria, yeast), recombinant, ribosome, mRNA, and DNA displays, or a combination thereof. Many methods can be used to manipulate antibodies to modify antibody properties including humanization, affinity maturation, antibody isotype switching, physiochemical property and pharmacokinetic profile improvement, etc., which are well known in the art.

1. Anti-Prostaglandin $E_2$ Monoclonal Antibodies Using Hybridoma Technology

Monoclonal antibodies can be prepared using a wide variety of techniques known in the art including the use of hybridoma, recombinant, phage, and yeast display technologies, or a combination thereof. Monoclonal antibodies can be produced, for example, using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention (See Example 1.2). Briefly, mice can be immunized with a carrier protein conjugated $PGE_2$ known as hapten-carrier protein conjugates. Here, the hapten is $PGE_2$ and carrier protein can be any of bovine thyroglobulins, keyhole limpet hemocyanin, bovine serum albumin, ovalbumin etc. In a preferred embodiment, the $PGE_2$-thyroglobulin conjugate is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a $PGE_2$-thyroglobulin conjugate, antibodies and/or antibody-producing cells may be obtained from the animal. An anti-$PGE_2$ antibody-containing serum is obtained from the animal by bleeding or sacrificing the animal. The serum may be used as it is obtained from the animal, an immunoglobulin fraction may be obtained from the serum, or the anti-$PGE_2$ antibodies may be purified from the serum. Serum or immunoglobulins obtained in this manner are polyclonal, thus having a heterogeneous array of properties.

Once an immune response is detected, e.g., antibodies specific for the antigen $PGE_2$ are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding $PGE_2$. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using $PGE_2$, or a portion thereof, or a cell expressing $PGE_2$. In a preferred embodiment, the initial screening is performed using an enzyme-linked immunoassay (ELISA) or a radioimmunoassay (RIA), preferably an ELISA. An example of ELISA screening is provided in WO 00/37504.

Anti-$PGE_2$ antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-$PGE_2$ antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

2. Anti-Prostaglandin $E_2$ Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) *Proc. Natl. Acad. Sci. USA* 93:7843-7848. In this method, single cells secreting antibodies of interest, e.g. lymphocytes derived from any one of the immunized animals described in Section 1, are screened using an antigen-specific hemolytic plaque assay, wherein the antigen $PGE_2$, a subunit of $PGE_2$, or a fragment thereof, is coupled to sheep red blood cells using a linker, such as biotin, and used to identify single cells that secrete antibodies with specificity for $PGE_2$. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS, HEK293, or CHO cells. The host cells transfected with the amplified immunoglobulin sequences, derived from in vivo selected lymphocytes, can then undergo further analysis and selection in vitro, for example by panning the transfected cells to isolate cells expressing antibodies to $PGE_2$. The amplified immunoglobulin sequences further can be manipulated in vitro, such as by in vitro affinity maturation methods such as those described in PCT Publication WO 97/29131 and PCT Publication WO 00/56772.

3. Anti-Prostaglandin $E_2$ Monoclonal Antibodies Using Transgenic Animals

In another embodiment of the instant invention, antibodies are produced by immunizing a non-human animal comprising some, or all, of the human immunoglobulin locus with a $PGE_2$-carrier protein conjugate. In a preferred embodiment, the non-human animal is a XENOMOUSE™ transgenic mouse, an engineered mouse strain that comprises large fragments of the human immunoglobulin loci and is deficient in mouse antibody production. See, e.g. Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE™ transgenic mouse produces an adult-like human repertoire of fully human antibodies, and generates antigen-specific human Mabs. The XENOMOUSE™ transgenic mouse contains approximately 80% of the human antibody repertoire through introduction of megabase sized, germline configuration YAC fragments of the human heavy chain loci and x light chain loci. See Mendez et al., *Nature Genetics* 15:146-156 (1997), Green and Jakobovits *J. Exp. Med.* 188: 483-495 (1998).

4. Anti-Prostaglandin $E_2$ Monoclonal Antibodies Using Recombinant Antibody Libraries In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131.

The recombinant antibody library may be from a subject immunized with $PGE_2$-carrier protein conjugate. Alternatively, the recombinant antibody library may be from a naïve subject, i.e., one who has not been immunized with $PGE_2$-carrier protein conjugate, such as a human antibody library from a human subject who has not been immunized with $PGE_2$-carrier protein conjugate. Antibodies of the invention are selected by screening the recombinant antibody library with an agent comprising $PGE_2$ to thereby select those antibodies that recognize $PGE_2$. Methods for conducting such screening and selection are well known in the art, such as described in the references in the preceding paragraph. To select antibodies of the invention having particular binding affinities for $PGE_2$, such as those that dissociate from $PGE_2$ with a particular $k_{off}$ rate constant, the art-known method of surface plasmon resonance can be used to select antibodies having the desired $k_{off}$ rate constant. To select antibodies of the invention having a particular neutralizing activity for $PGE_2$, such as those with a particular an $IC_{50}$, standard methods known in the art for assessing the inhibition of $PGE_2$ activity may be used.

For example, the antibodies of the present invention can also be generated using various phage display methods known in the art. In phage display methods, functional antibody domains are displayed on the surface of phage particles that carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988). Examples of techniques that can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94: 12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in Wittrup, et al. U.S. Pat. No. 6,699,658.

5. Anti-Prostaglandin E$_2$ Monoclonal Antibodies Using Profusion mRNA Display

PROfusion™ technology is one of the mRNA display technologies described above. PROfusion™ technology can be used to display human antibody fragments (VH or VL or scFv) coupled to their encoding DNA sequences for selecting against various antigens. Examples of mRNA display methods that can be used to make the antibodies of the present invention include those disclosed in Szostak, et al. U.S. Pat. Nos. 6,207,446; 6,214,553; and Gold, et al. U.S. Pat. No. 6,194,550 and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g. antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

6. Affinity Maturation of Anti-prostaglandin E$_2$ Monoclonal Antibodies

In vitro methods also can be used for the affinity maturation of the antibodies of the invention, wherein a mutagenesis antibody library is generated by introducing point mutation(s) in CDRs and/or frameworks of one initial antibody using error-prone PCR, or synthetic combinatorial oligo nucleotides, or oligo nucleotides directed mutagenesis. The mutagenesis library then can be screened to identify an antibody having the improved binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131.

Methods for conducting such screening and selection are well known in the art, such as described in the references in the preceding paragraph. To select antibodies of the invention having particular binding affinities for PGE$_2$, such as those that dissociate from PGE$_2$ with a particular k$_{off}$ rate constant, the art-known method of surface plasmon resonance can be used to select antibodies having the desired k$_{off}$ rate constant. To select antibodies of the invention having a particular neutralizing activity for PGE$_2$, such as those with a particular IC$_{50}$, standard, methods known in the art for assessing the inhibition of PGE$_2$ activity may be used.

For example, the antibodies of the present invention can also be affinity matured using various display methods known in the art. In phage display methods, functional antibody domains are displayed on the surface of phage particles that carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988). Examples of techniques that can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g. a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach, the antibodies of the present invention can be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in Wittrup, et al. U.S. Pat. No. 6,699,658.

B. Production Of Recombinant Prostaglandin $E_2$ Antibodies

Antibodies of the present invention may be produced by any of a number of techniques known in the art. For example, expression from host cells, wherein expression vector(s) encoding the heavy and light chains are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g. as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Production of Anti-Prostaglandin $E_2$ Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and discussed in detail in Example 2.1. See e.g., Morrison, Science 229:1202 (1985); Oi et al., Bio-Techniques 4:214 (1986); Gillies et al., (1989) J. Immunol. Methods 125:191-202; U.S. Pat. Nos. 5,807,715; 4,816,567; and 4,816,397. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the murine monoclonal anti $PGE_2$ antibodies described in section 1 with a human IgG1 constant region. In a specific embodiment the chimeric antibody of the invention comprises a heavy chain variable region ($V_H$) comprising the amino acid sequence of SEQ ID 60, 62, 64, 66, 68, 70, 72, 74, 76, 78, and 80 and light chain variable region (VL) SEQ ID 61, 63, 65, 67, 69, 71, 73, 75, 77, 79, and 81.

Anti-Prostaglandin $E_2$ Humanized Antibodies

Humanized antibodies are antibody molecules derived from a non-human species antibody that binds the desired antigen having one or more complementarity determining regions (CDRs) from the non-human species and framework regions from a human immunoglobulin molecule. Known human Ig sequences are disclosed, e.g., Kabat et al., Sequences of Proteins of Immunological Interest, U.S. Dept. Health (1983). Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988)). Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as, but not limited to, those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

C. Production of Antibodies and Antibody-Producing Cell Lines

Preferably, anti-$PGE_2$ antibodies of the present invention exhibit a high capacity to reduce or to neutralize $PGE_2$ activity, e.g., as assessed by any one of several in vitro and in vivo assays known in the art (e.g., see Example 1.1.C). For example, these antibodies neutralize $PGE_2$-induced calcium influx in EP4 assay with $IC_{50}$ values in the range of at least about $10^{-6}$ M, about $10^{-7}$ M, about $10^{-3}$ M, about $10^{-9}$ M, about $10^{-10}$ M, about $10^{-11}$ M or about $10^{-12}$ M.

In preferred embodiments, the isolated antibody, or antigen-binding portion thereof, binds $PGE_2$, wherein the antibody, or antigen-binding portion thereof, dissociates from $PGE_2$ with a $k_{off}$ rate constant of about 0.1 s$^{-1}$ or less, as determined by radioimmunoassay or which inhibits $PGE_2$ activity with an $IC_{50}$ of about $1\times10^{-6}$M or less. Alternatively, the antibody, or an antigen-binding portion thereof, may dissociate from $PGE_2$ with a $k_{off}$ rate constant of about $1\times10^{-2}$ s$^{-1}$ or less, as determined by radioimmunoassay, or may inhibit $PGE_2$ activity with an $IC_{50}$ of about $1\times10^{-7}$M or less. Alternatively, the antibody, or an antigen-binding portion thereof, may dissociate from $PGE_2$ with a $k_{off}$ rate constant of about $1\times10^{-3}$ s$^{-1}$ or less, as determined by radioimmunoassay, or may inhibit $PGE_2$ with an $IC_{50}$ of about $1\times10^{-8}$M or less. Alternatively, the antibody, or an antigen-binding portion thereof, may dissociate from $PGE_2$ with a $k_{off}$ rate constant of about $1\times10^{-3}$ s$^{-1}$ or less, as determined by radioimmunoassay, or may inhibit $PGE_2$ activity with an $IC_{50}$ of about $1\times10^{-9}$M or less. Alternatively, the antibody, or an antigen-binding portion thereof, may dissociate from $PGE_2$ with a $k_{off}$ rate constant of about $1\times10^{-5}$ s$^{-1}$ or less, as determined by radioimmunoassay, or may inhibit $PGE_2$ activity with an $IC_{50}$ of about $1\times10^{-10}$M or less. Alternatively, the antibody, or an antigen-binding portion thereof, may dissociate from $PGE_2$ with a $k_{off}$ rate constant of about $1 \times 10^{-6}$ s$^{-1}$ or less, as determined by radioimmunoassay, or may inhibit PGE$_2$ activity with an IC$_{50}$ of about $1 \times 10^{-11}$ M or less.

The monoclonal antibodies of the invention block PGE$_2$ binding to at least one of EP1, EP2, EP3, and EP4 receptors. Both FACS-based receptor binding assay and $^3$H-labeled PGE$_2$ binding assay on cell surface demonstrate that both murine version and humanized version anti-PGE2, are able to effectively block PGE$_2$ binding to its receptors. The crystal structure of PGE$_2$ complexed with the Fab portion of humanized anti-PGE$_2$ antibody Hu2B5.7 is envisioned by the invention In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260; 5,624,821). The Fc portion of an antibody mediates several important effector functions, e.g., cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example, the Fc region of the antibody, such that effector functions of the antibody are altered. In another embodiment, the activity of the Fc fragment can be greatly enhanced by sialylation of the N-linked glycan of the Fc portion (e.g., with 2,6-linkage to the penultimate galactose on the complex, biantennary glycan found at Asn 297 in immunoglobulin G (IgG)) (Anthony, R M (2008) Science 320:373-376).

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (e.g., by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (e.g., such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. Preferably the invention relates to crystals of whole anti-PGE$_2$ antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02072636.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are other objects of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such a glycosylation may increase the affinity of the antibody for antigen. Such an approach is described in further detail in PCT Publication WO2003016466A2, and U.S. Pat. Nos. 5,714,350 and 6,350,861.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342 80.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example, glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (i.e., glycoproteins) produced in these yeast strains exhibit protein glycosylation identical to that of animal cells, especially human cells (U.S. patent applications 20040018590 and 20020137134 and PCT publication WO2005100584 A2).

In addition to the binding proteins, the present invention is also directed to an anti-idiotypic (anti-Id) antibody specific for such binding proteins of the invention. An anti-Id antibody is an antibody that recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

D. Uses of Anti-Prostaglandin $E_2$ Antibodies

Given their ability to bind to $PGE_2$, the anti-$PGE_2$ antibodies, or portions thereof, of the invention can be used to detect $PGE_2$ (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting $PGE_2$ in a biological sample comprising contacting a biological sample with an antibody, or antibody portion, of the invention and detecting either the antibody (or antibody portion) bound to $PGE_2$ or unbound antibody (or antibody portion), to thereby detect $PGE_2$ in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, $PGE_2$ can be assayed in biological fluids by a competition immunoassay utilizing $PGE_2$ standards labeled with a detectable substance and an unlabeled anti-$PGE_2$ antibody. In this assay, the biological sample, the labeled $PGE_2$ standards and the anti-$PGE_2$ antibody are combined and the amount of labeled $PGE_2$ standard bound to the unlabeled antibody is determined. The amount of $PGE_2$ in the biological sample is inversely proportional to the amount of labeled $PGE_2$ standard bound to the anti-$PGE_2$ antibody. Similarly, $PGE_2$ can also be assayed in biological fluids by a competition immunoassay utilizing $PGE_2$ standards labeled with a detectable substance and an unlabeled anti-$PGE_2$ antibody.

The antibodies and antibody portions of the invention preferably are capable of neutralizing $PGE_2$ activity both in vitro and in vivo. Accordingly, such antibodies and antibody portions of the invention can be used to inhibit $PGE_2$ activity, e.g., in a cell culture containing $PGE_2$, in human subjects or in other mammalian subjects having $PGE_2$ with which an antibody of the invention cross-reacts. In one embodiment, the invention provides a method for inhibiting $PGE_2$ activity comprising contacting $PGE_2$ with an antibody or antibody portion of the invention such that $PGE_2$ activity is inhibited. For example, in a cell culture containing, or suspected of containing PGE$_2$, an antibody or antibody portion of the invention can be added to the culture medium to inhibit PGE$_2$ activity in the culture.

In another embodiment, the invention provides a method for reducing PGE$_2$ activity in a subject, advantageously from a subject suffering from a disease or disorder in which PGE$_2$ activity is detrimental. The invention provides methods for reducing PGE$_2$ activity in a subject suffering from such a disease or disorder, which method comprises administering to the subject an antibody or antibody portion of the invention such that PGE$_2$ activity in the subject is reduced. Preferably, the subject is a human subject. Alternatively, the subject can be a mammal expressing PGE$_2$ to which an antibody of the invention is capable of binding. Still further the subject can be a mammal into which PGE$_2$ has been introduced (e.g. by administration of PGE$_2$ or by expression of a PGE$_2$ synthetase transgene). An antibody of the invention can be administered to a human subject for therapeutic purposes. Moreover, an antibody of the invention can be administered to a non-human mammal expressing PGE$_2$ with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which PGE$_2$ activity is detrimental" is intended to include diseases and other disorders in which the presence of PGE$_2$ in a subject suffering from the disorder has been shown to be or is suspected of being either responsible for the pathophysiology of the disorder or a factor that contributes to a worsening of the disorder. Accordingly, a disorder in which PGE$_2$ activity is detrimental is a disorder in which reduction of PGE$_2$ activity is expected to alleviate the symptoms and/or progression of the disorder. Such disorders may be evidenced, for example, by an increase in the concentration of PGE$_2$ in a biological fluid of a subject suffering from the disorder (e.g., an increase in the concentration of PGE$_2$ in serum, plasma, synovial fluid, etc. of the subject), which can be detected, for example, using an anti-PGE$_2$ antibody as described above. Non-limiting examples of disorders that can be treated with the antibodies of the invention include those disorders discussed in the section below pertaining to pharmaceutical compositions of the antibodies of the invention.

PGE$_2$ has been implicated as having a pivotal role in causing pathological responses associated with rheumatoid arthritis. However other mediators of differential immunological pathways are also involved in arthritis, and blocking these mediators, in addition to PGE$_2$, may offer additional therapeutic benefit. Thus, binding proteins of the invention may be incorporated into DVD-Ig™ proteins where in the DVD-Ig™ is capable of binding target pairs including, but not limited to, PGE$_2$ and a pro-inflammatory cytokine, such as tumor necrosis factor-α (TNF-α). Blocking both PGE$_2$ and TNF-α may have beneficial effects that combining DMARD effect of TNF-α and pain relief from blocking PGE$_2$. In a preferred embodiment, the DVD-Ig™ of the invention binds the targets PGE$_2$ and TNFα and is used for treating rheumatoid arthritis.

One aspect of the invention pertains to a DVD-Ig™ binding protein comprising binding proteins capable of binding PGE$_2$. Preferably the DVD-Ig™ binding protein is capable of binding PGE$_2$ and a second target. The second target is selected from the group consisting of TNF, EGF, EGFR, IGF1, IGF2, IGF1/2, IGFR Erb2, Erb3, VEGF, VEGFR, Muc-1, CSF1 (MCSF), CSF2 (GM-CSF), CSF3 (GCSF), FGF2, IFNγ1, IFNγ1, IFNγ, histamine and histamine receptors, IL-1α, IL-1β, IL-2, IL-3, IL-4, IL-5, IL-6, IL-7, IL-8, IL-9, IL-10, IL-11, IL-12 α, IL-12 β, IL-14, IL-15, IL-16, IL-17, IL-18, IL-19, KITLG, PDGFB, IL-2R α, IL-4R, IL-5R α, IL-8R α, IL-8R β, IL-12R β,1, IL-12R β,2, IL-18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, LTBR, and Chitinase. More preferably, the DVD binding protein is capable of recognizing PGE$_2$ and TNF α, PGE$_2$ and IL-6, PGE$_2$ and IL-1β, PGE$_2$ and IL-6R, PGE$_2$ and CTLA-4, PGE$_2$ and EGF; PGE2 and IGF-1/2, PGE$_2$ and Erb2, PGE$_2$ and Erb3, PGE$_2$ and VEGF. Most preferably, the DVD binding protein is capable of binding PGE$_2$ and TNF α. Preferred DVD-Igs for treating autoimmune diseases include but are not limited to a DVD-Ig containing an anti PGE$_2$ antibody and a target selected from the group consisting of TNF α, IL-1α, IL-1β, IL-6 or IL-6R, CTLA-4Ig, BAFF, TACI, RANKL, or DKK1 or SOCT, MMP13, or MMP1 or MMP4. Target pairs preferably for cancer therapy include PGE$_2$+EGF or EGFR, PGE$_2$+IGF1 or IGF1R, PGE$_2$+IGF2 or IGF2R, PGE$_2$+IGF1/2, PGE$_2$+VEGF or VEGFR, PGE$_2$+Erb2, PGE$_2$+Erb3, and PGE$_2$+S1P.

PGE$_2$ has been implicated as having a pivotal role in causing pathological responses associated with rheumatoid arthritis or cancer. However other mediators of differential immunological pathways are also involved in arthritis or cancer, and blocking these mediators, in addition to PGE$_2$, may offer additional therapeutic benefit. A list of the drugs that currently are used for the treatment of various human diseases and disorders is available on the internet. This list is updated frequently to reflect state-of-art for the treatment of various human diseases. Anti-PGE$_2$ can be combined with any of the therapies in that list for a particular disease conditions. A few examples are provided below. Anti-PGE$_2$ can be combined with one or more agents for the treatment of rheumatoid arthritis and juvenile rheumatoid arthritis. Examples of these agents include but are not limited to the agents listed below, for example, drugs that decrease pain and inflammation while decreasing the growth of abnormal synovial tissue (the tissue that lines the inside of the joint). These drugs include methotrexate and low doses of corticosteroids (such as prednisone or cortisone). In some people, these drugs also decrease joint destruction. Other medications used to treat rheumatoid arthritis include: anti-malarial medications (such as hydroxychloroquine), gold, sulfasalazine, penicillamine, cyclophosphamide, cyclosporin and minocycline. In addition, more than one drug may be prescribed. Newer biologic agents that block the effects of specific inflammatory factors (cytokines) are now available. Infliximab, etanercept and adalimumab block the cytokine TNFα, abatacept blocks T cell costimulation, rituximab depletes B cells, anakinra blocks the cytokine interleukin-1, and other new biologic agents target IL-6, IL-6R, IL-17, IL-18, IL-23, B7.1/B7.2. Anti-PGE$_2$ can combine with one or more agents for the treatment of ankylosing spondylitis. Examples of these agents include but are not limited to corticosteroids, cytotoxic drugs and most recently anti-TNFα agents. Anti-PGE$_2$ can be combined with one or more agents for the treatment of multiple sclerosis. Examples of these agents include but are not limited to Avonex™, Azasan™, Azathioprine, Betaseron™, Bubbli-Pred™, Copaxone™, Cotolone, Glatiramer, Imuran™, Interferon Beta-1a, Interferon Beta-1b Solution, Key-Pred, Key-Pred SP, Mitoxantrone, Natalizumab, Novantrone™, Orapred™, Orapred ODT™, Pediapred™, Pred-Ject-50, Predacort 50, Predalone 50, Predate-50, Prednisolone, Prelone™, Rebif™, and Tysabri™. Anti-PGE$_2$ can be combined with one or more agents or treatment procedures for the treatment of pain. Anti-PGE$_2$ can be combined with one or more agents or treatment procedures for the treatment of Crohn's disease. Anti-PGE$_2$ can combine with one or more agents or treatment procedures for the treatment of various human cancers and malignancies.

E. Pharmaceutical Composition

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating a disorder or one or more symptoms thereof, and/or in research. In a specific embodiment, the pharmaceutical composition comprises one or more antibodies of the invention. In another embodiment, the pharmaceutical composition comprises one or more antibodies of the invention and one or more prophylactic or therapeutic agents other than antibodies of the invention for treating a disorder in which PGE$_2$ activity is detrimental. Preferably, the prophylactic or therapeutic agents known to be useful for or that have been or are currently being used in the prevention, treatment, management, or amelioration of a disorder or one or more symptoms thereof. In accordance with these embodiments, the composition may further comprise of a carrier, diluent or excipient.

The antibodies and antibody portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment. This may be achieved by, for example, local infusion, by injection, or by means of an implant, such an implant being of a porous or non-porous material, including membranes and matrices, such as sialastic membranes, polymers, fibrous matrices (e.g., Tissuel®), or collagen matrices. In one embodiment, an effective amount of one or more antibodies of the invention is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent of the invention can be delivered in a controlled release or sustained release system. In one embodiment, a pump may be used to achieve controlled or sustained release (see Langer, supra; Sefton, 1987, CRC Crit. Ref Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy &Oncology 39:179-189, Song et al., 1995, "Antibody Mediated Lung Targeting of Long-Circulating Emulsions," PDA Journal of Pharmaceutical Science &Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e., greater than 1 ml) with less pain and discomfort, and minimum incidence of injection site reactions (see WO2004078140 and US2006104968).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which $PGE_2$ activity is detrimental. For example, an anti-$PGE_2$ antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to $PGE_2$ or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley &Sons, NY (1993); and Kriegler, Gene Transfer and Expression, A Laboratory Manual, Stockton Press, NY (1990). Detailed descriptions of various methods of gene therapy are disclosed in US20050042664 A1.

In another aspect, this application features a method of treating (e.g., curing, suppressing, ameliorating, delaying or preventing the onset of, or preventing recurrence or relapse of) or preventing a $PGE_2$-associated disorder, in a subject. The method includes: administering to the subject a $PGE_2$ binding agent (particularly an antagonist), e.g., an anti-$PGE_2$ antibody or fragment thereof as described herein, in an amount sufficient to treat or prevent the $PGE_2$-associated disorder. The $PGE_2$ antagonist, e.g., the anti-$PGE_2$ antibody or fragment thereof, can be administered to the subject, alone or in combination with other therapeutic modalities as described herein.

The invention provides methods for the treatment of inflammatory disorders and disorders of immunity in a subject, which disorders are characterised by excessive $PGE_2$ biosynthesis, which methods comprise administering to the subject an effective amount of a antibody specific to $PGE_2$. Disorders that may be treated by the method according to the invention include autoimmune and inflammatory diseases and tumors in which excessive $PGE_2$ synthesis has been implicated. Such disorders include: (a) rheumatoid and allergic arthritis; (b) certain illnesses induced by viruses, such as Guillain Barre syndrome, infectious mononucleosis, other viral lymphadenopathies and infections with herpes virus; (c) multiple sclerosis and other demyelinating diseases; (d) hematological disorders, such as hemolytic anemias and thrombocytopenias; (e) endocrinologic disorders, such as diabetes mellitus, Addison's disease, idiopathic hypoparathyroidism and chronic lymphocytic thyroiditis; (f) collagen disorders, such as systemic lupus erythematosus; and (g) disorders of reproduction such as amenorrhoea, infertility, recurrent abortions and eclampsia; and (h) tumors such as headneck tumor, lung cancer, gastric cancer, prostate cancer, pancreatic cancer, etc., and (i) inflammatory and/or autoimmune conditions of the skin, gastrointestinal organs (e.g., inflammatory bowel diseases (IBD), such as ulcerative colitis and/or Crohn's disease); and (j) pain related with osteoarthritis and other disorders; and (k) ocular disorders such as age-related mascular degeneration (AMD). Accordingly, the disclosure includes the use of a $PGE_2$ binding agent (such as an anti-$PGE_2$ antibody or fragment thereof described herein) for a treatment described herein and the use of a $PGE_2$ binding agent (such as an anti-$PGE_2$ antibody or fragment thereof described herein) for preparing a medicament for a treatment described herein.

Examples of $PGE_2$-associated disorders include, but are not limited to, a disorder selected from the group consisting of arthritis, rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/ Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/ HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, vital-associated hemaphagocytic syndrome, Wernicke-Korsakoff syndrome, Wilson's disease, xenograft rejection of any organ or tissue, Acute coronary syndromes, Acute Idiopathic Polyneuritis, Acute Inflammatory Demyelinating Polyradiculoneuropathy, Acute ischemia, Adult Still's Disease, Alopecia greata, Anaphylaxis, Anti-Phospholipid Antibody Syndrome, Aplastic anemia, Arteriosclerosis, Atopic eczema, Atopic dermatitis, Autoimmune dermatitis, Autoimmune disorder associated with *Streptococcus* infection, Autoimmune Enteropathy, Autoimmune hearingloss, Autoimmune Lymphoproliferative Syndrome (ALPS), Autoimmune myocarditis, Autoimmune premature ovarian failure, Blepharitis, Bronchiectasis, Bullous pemphigoid, Cardiovascular Disease, Catastrophic Antiphospholipid Syndrome, Celiac Disease, Cervical Spondylosis, Chronic ischemia, Cicatricial pemphigoid, Clinically isolated Syndrome (CIS) with Risk for Multiple Sclerosis, Conjunctivitis, Childhood Onset Psychiatric Disorder, Chronic obstructive pulmonary disease (COPD), Dacryocystitis, dermatomyositis, Diabetic retinopathy, Diabetes mellitus, Disk herniation, Disk prolaps, Drug induced immune hemolytic anemia, Endocarditis, Endometriosis, endophthalmitis, Episcleritis, Erythema multiforme, erythema multiforme major, Gestational pemphigoid, Guillain-Barré Syndrome (GBS), Hay Fever, Hughes Syndrome, Idiopathic Parkinson's Disease, idiopathic interstitial pneumonia, IgE-mediated Allergy, Immune hemolytic anemia, Inclusion Body Myositis, Infectious ocular inflammatory disease, Inflammatory demyelinating disease, Inflammatory heart disease, Inflammatory kidney disease, IPF/UIP, Iritis, Keratitis, Keratojuntivitis sicca, Kussmaul disease or Kussmaul-Meier Disease, Landry's Paralysis, Langerhan's Cell Histiocytosis, Livedo reticularis, Macular Degeneration, Microscopic Polyangiitis, Morbus Bechterev, Motor Neuron Disorders, Mucous membrane pemphigoid, Multiple Organ failure, Myasthenia Gravis, Myelodysplastic Syndrome, Myocarditis, Nerve Root Disorders, Neuropathy, Non-A Non-B Hepatitis, Optic Neuritis, Osteolysis, Pauciarticular JRA, peripheral artery occlusive disease (PAOD), peripheral vascular disease (PVD), peripheral artery disease (PAD), Phlebitis, Polyarteritis nodosa (or periarteritis nodosa), Polychondritis, Polymyalgia Rheumatica, Poliosis, Polyarticular JRA, Polyendocrine Deficiency Syndrome, Polymyositis, polymyalgia rheumatica (PMR), Post-Pump Syndrome, primary parkinsonism, Prostatitis, Pure red cell aplasia, Primary Adrenal Insufficiency, Recurrent Neuromyelitis Optica, Restenosis, Rheumatic heart disease, SAPHO (synovitis, acne, pustulosis, hyperostosis, and osteitis), Scleroderma, Secondary Amyloidosis, Shock lung, Scleritis, Sciatica, Secondary Adrenal Insufficiency, Silicone associated connective tissue disease, Sneddon-Wilkinson Dermatosis, spondilitis ankylosans, Stevens-Johnson Syndrome (SJS), Systemic inflammatory response syndrome, Temporal arteritis, toxoplasmic retinitis, toxic epidermal necrolysis, Transverse myelitis, TRAPS (Tumor Necrosis Factor Receptor, Type 1 allergic reaction, Type II Diabetes, Urticaria, Usual interstitial pneumonia (UIP), Vasculitis, Vernal conjunctivitis, viral retinitis, Vogt-Koyanagi-Harada syndrome (VKH syndrome), Wet macular degeneration, and Wound healing.

In another aspect, the binding proteins of the invention are useful for treating a disorder selected from the group consisting of Acute Lymphoblastic Leukemia, Acute Myeloid Leukemia, Adrenocortical Carcinoma, Anal Cancer, Appendix Cancer, Cerebellar Astrocytoma, Cerebral Astrocytoma, Basal Cell Carcinoma, Bile Duct Cancer, Extrahepatic, Bladder Cancer, Bone Cancer, Osteosarcoma/Malignant Fibrous Histiocytoma Brain Stem Glioma, Brain Tumor, Brain Stem Glioma, Cerebral strocytoma/Malignant Glioma, Ependymoma, Medulloblastoma, Supratentorial Primitive Neuroectodermal Tumors, Visual Pathway and Hypothalamic Glioma, Breast Cancer, Bronchial Adenomas/Carcinoids, Carcinoid Tumor, Carcinoid Tumor, Gastrointestinal Carcinoma of Unknown Primary, Central Nervous System Lymphoma, Primary Cerebellar Astrocytoma, Cervical Cancer, Chronic Lymphocytic Leukemia, Chronic Myelogenous Leukemia Chronic Myeloproliferative Disorders, Colon Cancer, Colorectal Cancer, Cutaneous T-Cell Lymphoma, Endometrial Cancer, Ependymoma, Esophageal Cancer, Ewing Family of Tumors, Extracranial Germ Cell Tumor, Extragonadal Germ Cell Tumor, Extrahepatic Bile Duct Cancer, Eye Cancer, Intraocular Melanoma Retinoblastoma, Gallbladder Cancer, Gastric (Stomach) Cancer, Gastrointestinal Carcinoid Tumor, Gastrointestinal Stromal Tumor (GIST), Extracranial Germ Cell Tumor, Extragonadal Germ Cell Tumor, Ovarian Germ Cell Tumor, Gestational Trophoblastic Tumor, Glioma, Brain Stem Glioma, Cerebral Astrocytoma Glioma, Childhood Visual Pathway and Hypothalamic Glioma, Hairy Cell Leukemia, Head and Neck Cancer, Hepatocellular (Liver) Cancer, Hodgkin Lymphoma, Hypopharyngeal Cancer, Intraocular Melanoma, Islet Cell Carcinoma (Endocrine Pancreas), Kaposi Sarcoma, Kidney (Renal Cell) Cancer, Laryngeal Cancer, Acute Lymphoblastic Leukemia, Acute Myeloid Leukemia, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Burkitt Lymphoma, Cutaneous T-Cell Lymphoma, Hodgkin Lymphoma, Non-Hodgkin Lymphoma, Primary Central Nervous System Lymphoma, Waldenström Macroglobulinemia, Malignant Fibrous Histiocytoma of Bone/Osteosarcoma, Medulloblastoma, Melanoma, Intraocular (Eye) Melanoma, Merkel Cell Carcinoma, Malignant Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Chronic Myeloid Leukemia, Multiple Myeloma, Myeloproliferative Disorders, Nasal Cavity and Paranasal Sinus Cancer, Nasopharyngeal Cancer, Neuroblastoma, Oral Cancer, Oral Cavity Cancer, Lip and Oropharyngeal Cancer, Osteosarcoma/Malignant Fibrous Histiocytoma of Bone, Ovarian Cancer, Ovarian Epithelial Cancer, Ovarian Germ Cell Tumor, Ovarian Low Malignant Potential Tumor, Pancreatic Cancer, Islet Cell Pancreatic Cancer, Paranasal Sinus and Nasal Cavity Cancer, Parathyroid Cancer, Penile Cancer, Pharyngeal Cancer, Pheochromocytoma, Pineoblastoma and Supratentorial Primitive Neuroectodermal Tumors, Pituitary Tumor, Plasma Cell Neoplasm/Multiple Myeloma, Pleuropulmonary Blastoma, Prostate Cancer, Rectal Cancer, Renal Cell (Kidney) Cancer, Renal Pelvis and Ureter, Transitional Cell Cancer, Retinoblastoma, Salivary Gland Cancer, Sarcoma, Ewing Family of Tumors, Kaposi Sarcoma, Soft Tissue Sarcoma, Uterine Sarcoma, Sézary Syndrome, Skin Cancer (Nonmelanoma), Skin Cancer (Melanoma), Merkel Cell Skin Carcinoma, Small Intestine Cancer, Squamous Cell Carcinoma, Metastatic Squamous Neck Cancer with Occult Primary, Stomach (Gastric) Cancer, Supratentorial Primitive Neuroectodermal Tumors, Cutaneous T-Cell Lymphoma, Testicular Cancer, Throat Cancer, Thymoma, Thymoma and Thymic Carcinoma, Thyroid Cancer, Transitional Cell Cancer of the Renal Pelvis and Ureter, Gestational Trophoblastic Tumor, Ureter and Renal Pelvis, Transitional Cell Cancer, Urethral Cancer, Uterine Cancer, Endometrial Uterine Sarcoma, Vaginal Cancer, Visual Pathway and Hypothalamic Glioma, Vulvar Cancer, Waldenström Macroglobulinemia, and Wilms Tumor.

In another aspect, the invention provides a method for detecting the presence of $PGE_2$ in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-$PGE_2$ antibody or fragment thereof as described herein; and (ii) detecting formation of a complex between the anti-$PGE_2$ antibody or fragment thereof, and the sample or the control sample, wherein a statistically significant change in the formation of the complex in the sample relative to the control sample is indicative of the presence of the $PGE_2$ in the sample.

In yet another aspect, this application provides a method for detecting the presence of $PGE_2$ in vivo (e.g., in vivo imaging in a subject). The subject method can be used to diagnose a disorder, e.g., a $PGE_2$-associated disorder. The method includes: (i) administering the anti-$PGE_2$ antibody or fragment thereof as described herein to a subject or a control subject under conditions that allow binding of the antibody or fragment to $PGE_2$; and (ii) detecting formation of a complex between the antibody or fragment and $PGE_2$, wherein a statistically significant change in the formation of the complex in the subject relative to the control subject is indicative of the presence of $PGE_2$.

Antibodies of the invention, or antigen binding portions thereof, can be used alone or in combination to treat such diseases. It should be understood that the antibodies of the invention or antigen binding portion thereof can be used alone or in combination with an additional agent, e.g., a therapeutic agent, the additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition, e.g., an agent that affects the viscosity of the composition.

It should further be understood that the combinations that are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

The combination therapy can include one or more PGE2 antagonists, e.g., anti-$PGE_2$ antibodies or fragments thereof, coformulated with, and/or coadministered with, one or more additional therapeutic agents, e.g., one or more cytokine and growth factor inhibitors, immunosuppressants, anti-inflammatory agents (e.g., systemic anti-inflammatory agents), antifibrotic agents, metabolic inhibitors, enzyme inhibitors, and/or cytotoxic or cytostatic agents, as described in more herein. Examples of preferred additional therapeutic agents that can be coadministered and/or coformulated with one or more $PGE_2$ antagonists, e.g., anti-$PGE_2$ antibodies or fragments thereof, include, but are not limited to, one or more of: inhaled steroids; beta-agonists, e.g., short-acting or long-acting beta-agonists; antagonists of leukotrienes or leukotriene receptors; combination drugs such as ADVAIR™; IgE inhibitors, e.g., anti-IgE antibodies (e.g., XOLAIR™); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be coadministered and/or coformulated with one or more anti-PGE2 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL™)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others. Other combinations are cytokine suppressive anti-inflammatory drug(s) (CSAIDs); antibodies to or antagonists of other human cytokines or growth factors, for example, ILA1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and edothelin-1, as well as the receptors of these cytokines and growth factors. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the inflammatory cascade. Preferred examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNF converting enzyme (TACE) inhibitors; similarly IL-1 inhibitors (Interleukin-1-converting enzyme inhibitors, IL-1RA etc.) may be effective for the same reason.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXEMPLIFICATION

Example 1

Generation and Isolation of Anti Prostaglandin $E_2$ Monoclonal Antibodies

Example 1.1

Assays to Identify Anti Human Prostaglandin $E_2$ Antibodies

The following assays were used to identify and characterize anti-prostaglandin $E_2$ antibodies unless otherwise stated.

Example 1.1.A

ELISA

Enzyme linked immunosorbent assays to screen for antibodies that bind prostaglandin $E_2$ were performed according to at least one of the two following methods.
Method 1
ELISA plates (Costar 3369, Corning, N.Y.) were coated with 50 µl of anti-host Fc IgG (Sigma, St. Louis, Mo.) at 2 µg/ml in PBS (Invitrogen Carlsbad, Calif.). Following an overnight incubation at 4° C., washed with PBS and the plate was blocked with 200 µl Superblock (Pierce #37535, Rockford, Ill.). The IgG containing samples were diluted to 1 µg/ml in Assay Buffer (10% Superblock in PBS containing 0.05% Surfactamps (Pierce #37535, Rockford, Ill.) and 50 µl/well added to each well and incubated for 1 hour at room temperature. Plates were washed four times with Tween-Tris Buffered Solution (TTBS). PGE2-biotinamide (Cayman Chemicals, Ann Arbor, Mich.) was diluted to 30 nM and serially diluted 1:3 in Assay Buffer. The titration curve samples were added to each IgG sample at 50 µl/well and incubated for 1 hour at room temperature. The plates were washed as previously described and 50 µl of 1:5000 dilution of streptavidin polyhrp40 (Fitzgerald Industries, Concord, Mass.) in Assay Buffer was added to each well and incubated for 45 minutes at room temperature. A final wash step was performed and the plates were developed using a single step TMB system (Sigma #T8665, St. Louis, Mo.) and 100 µl/well 2N $H_2SO_4$. Plates were read at 450 nm on a Molecular Devices Spectramax plate reader (Sunnyvale, Calif.). $EC_{50}$ was determined using GraphPad Prism 5 (GraphPad Software, La Jolla, Calif.).

Method 2

Alternatively, prostaglandin binding was determined using a $^3H$-$PGE_2$ ELISA. Plates were coated at 50 µL/well with 5 µg/ml of goat anti-human IgG (Fc) (Thermo Scientific # 31170, Hudson, N.H.) or goat anti-mouse IgG (Fc) (Thermo Scientific # 31125, Hudson, N.H.) in PBS and incubated overnight at 4° C. The following day, plates were flicked and blotted dry. Plates were blocked with 200 µL/well of Superblock (Thermo Scientific # 37515, Hudson, N.H.) for 1 hour at room temperature. Plates were flicked and blotted dry. Monoclonal antibodies were diluted to 0.04 µg/ml in phosphate buffer solution with Tween 20 (PBST) (Abbott Bioresearch Center, Worcester, Mass.) and 10% Superblock and 50 µL of each antibody was added to each well of the pre-blocked ELISA plate at 2 ng/well and incubated for 1 hour at room temperature. Wells were washed 3 times with PBS+ 0.1% Tween-20. A serial 3-fold titration of $^3H$-$PGE_2$ (Perkin Elmer # NET-428, Waltham, Mass.) was prepared in PBST/10% Superblock. Fifty microliters of the $^3H$-$PGE_2$ solution was added to each well of the plate and incubated for 1 hour at room temperature. Wells were washed manually 6 times with PBST/10% Superblock and 50 µL of scintillation fluid (Perkin Elmer # 6013621, Waltham, Mass.) was added to each well. Plates were read using a TopCount reader (Perkin Elmer, Waltham, Mass.) with a 5 minute count delay. An $EC_{50}$ number was determined using GraphPad Prism 5 (GraphPad Software, La Jolla, Calif.).

Example 1.1.B $PGE_2$ Competition ELISA

Competition enzyme linked immunosorbent assays were performed to determine prostaglandin binding specificity for antibodies that bind prostaglandin $E_2$, according to at least one of the two following methods.

Method 1

ELISA plates (Costar 3369, Corning, N.Y.) were coated with 50 µl/well of anti-host Fc IgG (Sigma, St. Louis, Mo.) at 2 µg/ml in PBS (Invitrogen, Carlsbad, Calif.). Following an overnight incubation at 4° C., the plate was blocked with 200 µl Superblock (Pierce #37535, Rockford, Ill.). The IgG samples were diluted to 6 µg/ml in Assay Buffer (10% Superblock in PBS containing 0.05% Surfactamps (Pierce #37535, Rockford, Ill.). The $PGE_2$-biotinamide was diluted to 3 nM in Assay Buffer. A titration curve in Assay Buffer was prepared for the prostaglandins $PGA_2$ (Cayman Chemicals, Ann Arbor, Mich.), $PGD_2$ (Cayman Chemicals, Ann Arbor, Mich.) and $PGE_2$ (Cayman Chemicals, Ann Arbor, Mich.) starting at 300 nM by a 1:10 serial dilution. The reagents were added to tubes at a volume of 50 µl each/tube and preincubated for 1 hour at room temperature. Following the preincubation, the mix was transferred to the blocked plates and allowed to incubate for 1 hour at room temperature. Next, the plates were washed four times with Tween 20-Tris buffered solution (TTBS). Streptavidin polyhrp40 in Assay Buffer (Fitzgerald Industries, Concord, Mass.) at a 1:5000 dilution was then added to the wells and incubated for 45 minutes at room temperature. A final wash step was performed and the plates were developed using a single step TMB system (Sigma #T8665, Sigma, St. Louis, Mo.) and 100 µl/well 2N $H_2SO_4$. Plates were read at 450 nm on a Molecular Devices Spectramax plate reader (Sunnyvale, Calif.). Wells in which unlabeled prostaglandins competed with the $PGE_2$-biotinamide for binding resulted in a decrease of signal. $IC_{50}$ number was determined using GraphPad Prism 5 (GraphPad Software, La Jolla, Calif.). The cross reactivity index was then calculated by $IC_{50}$ of $PGE_2$/$IC_{50}$ of other prostaglandin(s).

Method 2

Alternatively, prostaglandin selectivity was determined using a $^3H$-$PGE_2$ competition ELISA. Plates were coated with 50 µL/well of 5 µg/ml of goat anti-human IgG (Fc) (Thermo Scientific # 31170, Hudson, N.H.) or goat anti-mouse IgG (Fc) (Thermo Scientific # 31125, Hudson, N.H.) in PBS and incubated overnight at 4° C. The following day plates were flicked and blotted dry. Plates were blocked with 200 µL/well of Superblock (Thermo Scientific # 37515, Hudson, N.H.), 1 hour at room temperature. Plates were flicked and blotted dry. Monoclonal antibodies were diluted to 0.04 µg/ml in PBST (Abbott Bioresearch Center, Worcester, Mass.)/10% Superblock and 50 µL of each was added to each well (2 ng/well) of the pre-blocked ELISA plate and incubated for 1 hour at room temperature. Wells were washed 3 times with PBS/0.1% Tween-20. $^3H$-$PGE_2$ (Perkin Elmer # NET-428, Waltham, Mass.) was diluted in PBST/10% Superblock to 6 nM (2× stock). Each prostaglandin (Cayman Chemicals, Ann Arbor, Mich.) was prepared in PBST+10% Superblock at various concentrations ranging from 2000 µM (2× stock) to 0.00004 µM (2×). Equal volumes of the $^3H$-$PGE_2$ solution and of each prostaglandin dilution were mixed. Fifty microliters of this mixture was then added to each well of the plate and incubated for 1 hour at room temperature. Wells were washed manually 6 times with PBST/10% Superblock and 50 µL of scintillation fluid (Perkin Elmer # 6013621, Waltham, Mass.) added to each well. Plates were read using a TopCount reader (Perkin Elmer, Waltham, Mass.) with a 5 minute count delay. $IC_{50}$ number was determined using GraphPad Prism 5 (GraphPad Software, La Jolla, Calif.). The cross reactivity index was then calculated by $IC_{50}$ of $PGE_2$/$IC_{50}$ of other prostaglandin(s)

Example 1.1.C

Measurement of Functional Activity of Anti Prostaglandin $E_2$ Antibodies

To examine the functional activity of the anti-$PGE_2$ antibodies of the invention, the antibodies were used in the following in vitro and in vivo assays that measure the ability of an antibody to inhibit $PGE_2$ activity.

Example 1.1.C.1

EP4 Bioassay

The ability of anti-$PGE_2$ antibody to inhibit cellular response of $PGE_2$ in vitro was determined in a $Ca^{++}$ flux assay in HEK293 Gα16 cells (Abbott Bioresearch Center, Worcester, Mass.) stably transfected with human EP4 receptor. In brief, an expression plasmid encoding one of the four human PGE$_2$ receptors, EP4, and an expression plasmid encoding Gα16, were co-transfected into human embryonic kidney cell line 293 cells (ATCC# CRL1573, Manassas, Va.). The stable clones co-expressing both human EP4 and Gα16 protein were selected using standard methods (Joseph Sambrook and David W. Russell. Molecular Cloning: A Laboratory Manual Publisher. Published by Cold Spring Harbor Laboratory Press, 2001) and used for the EP4 bioassay.

The HEK293 Gα16 cells were plated in black/clear poly-D-lysine plates (Corning #3667, Corning, N.Y.) and incubated with a Ca$^{++}$-sensitive dye (Molecular Devices, Sunnyvale, Calif.) for 90 minutes. Stock PGE$_2$ (in 200 proof ethanol) was diluted with FLIPR buffer [containing 1×HBSS (Invitrogen Carlsbad, Calif.), 20 mM HEPES (Invitrogen Carlsbad, Calif.), 0.1% BSA (Sigma, St. Louis, Mo.) and 2.5 mM Probenecid (Sigma, St. Louis, Mo.)]. Anti-PGE$_2$ antibodies or isotype matched control antibodies were also pre-diluted in FLIPR buffer. 25 μl of PGE$_2$ or pre-incubated PGE$_2$/antibody mixture was added to the wells pre-plated with cells. The dose response of PGE$_2$ was determined on a serial titration of PGE$_2$ and using FLIPR1 or Tetra (Molecular Devices, Sunnyvale, Calif.) and EC$_{50}$ was determined using GraphPad Prism 5 (GraphPad Software, La Jolla, Calif.). For testing antibodies, PGE$_2$ at EC$_{50}$ concentration was incubated with varying concentrations of test antibodies or isotype matched antibody (negative control) (ABC) for 20 minutes, and added to dye-loaded human EP4 in HEK293 Gα16 cells. Ca$^{++}$ flux was monitored using FLIPR1 and data was analyzed using GraphPad Prism 5 (GraphPad Software, La Jolla, Calif.).

Example 1.1.C.2

Competitive Inhibition of PGE$_2$ Binding to PGE$_2$ Receptors by Anti Prostaglandin E$_2$ Antibodies Using $^3$H-PGE$_2$ Competitive inhibition of PGE$_2$ binding to PGE$_2$ receptors, for example EP4 or EP3, by an anti-PGE$_2$ antibody are determined using a cell-based or membrane based receptor binding assay using $^3$H-PGE$_2$ (ProstaglandinE2, [5,6,8,11,12,14,15-3H(N)], Perkin Elmer, Waltham, Mass. Cat# NET428250UC).

Cells endogenously expressing or stably overexpressing EP4 receptor (i.e., HEK293-EP4 cells or HEK293-EP4-Gα16 cells used for EP4 bioassay) (10$^5$ cells/mL) are grown overnight in a 24-well plate in DMEM medium (Invitrogen, Carlsbad, Calif.)/10% FCS (Sigma #T8665, Sigma, St. Louis, Mo.). The medium is removed and 100 μl binding buffer (medium without FCS) is added. The plate is placed on ice for 10 minutes. Non-radioactive PGE$_2$ (0-1 μM) is added together with tracer (40 μM of $^3$H-PGE$_2$) in 100 μl volume. Equilibrium receptor binding is performed for 90 minutes at 4° C. The medium is removed and the cells are washed four times with 200 μl cold medium. The cells are harvested by adding 20 μl 0.5 M NaOH. The lysate is transferred to a liquid scintillation plate. 100 μl Aquasafe 500 (Zinsser Analytic, Frankfurt, Germany) plus LSC cocktail (Lumac LSC, Groningen, The Netherlands) is added to each well and mixed. The cell-bound radioactivity is determined by liquid scintillation counting. For most agonist-receptor interactions, it is assumed that receptor binding inhibition by agonist (PGE$_2$) follows a one-site model. The EC$_{50}$, K$_i$ and K$_d$ values are calculated using the GraphPad Prism 5 (GraphPad Software, La Jolla, Calif.).

Inhibition of an anti-PGE$_2$ antibody on the binding of $^3$H-PGE$_2$ (ProstaglandinE2, [5,6,8,11,12,14,15-3H(N)], Perkin Elmer, Waltham, Mass. Cat# NET428250UC) to the EP3 receptor was performed using membrane preparations from cells that over-express the EP3 receptor (Millipore, Billerica, Mass.). Before the binding assay, 50 μl/well of 0.3% Polyethyleneimine (PEI) (Sigma, St. Louis, Mo.) was added to a Unifilter-96 GF/B filter plate (Perkin Elmer, Waltham, Mass.) and placed at 4° C. for one hour until ready for use. A 1:3 dilution of antibody was prepared at 2× concentration in binding buffer (50 mM HEPES pH 7.0, 10 mM MgCl$_2$, 1 mM EDTA, 0.2% BSA). H-PGE$_2$ was prepared at 2× concentration in binding buffer. 50 μl of a serial 3 fold dilution of antibody was then added to each well containing 50 μl of 200 pM $^3$H-PGE$_2$, mixed well and allowed to sit at room temperature for 10 minutes. Frozen membranes were thawed and resuspended in binding buffer. 5 μg of membrane was added to each well. Mixtures were incubated at room temperature for 60 minutes before filtering onto pretreated GF/B filtration plates using a Packard 96 well harvester. Plates were then dried for one hour before adding Microscint™ 20 (Perkin Elmer, Waltham, Mass.). Plates were then sealed and counted on the TopCount reader (Perkin Elmer, Waltham, Mass.). Non-specific binding was determined in the presence of 100 μM cold PGE$_2$. The measured radioactivity (cpm) was used to determine IC$_{50}$ values using Graphpad Prism (GraphPad Software, La Jolla, Calif.).

Example 1.1.C.3

Competitive Inhibition of PGE$_2$ Binding to PGE$_2$ Receptors by Anti Prostaglandin E$_2$ Antibodies Using a Cell Based FACS Assay Competitive inhibition of PGE$_2$ binding to PGE$_2$ receptors, for example EP4, by an anti-PGE$_2$ antibody can be determined using a cell-based FACS assay using PGE$_2$-biotinimide (Cayman Chemical, Ann Arbor, Mich. Cat# 10006987) and Streptavidin-R-Phycoerythrin (SA-RPE; Invitrogen, Carlsbad, Calif., Cat# 15-4301). Cells (1×10$^6$) endogenously expressing or stably overexpressing EP4 (i.e., HEK293-EP4 cells or HEK293-EP4-Gα16 cells used for EP4 bioassay) are cultivated in DMEM medium (Invitrogen, Carlsbad, Calif.)/10% FCS (Sigma #T8665, Sigma, St. Louis, Mo.). Cells are harvested and washed several times with 500 μl washing buffer (PBS/1% BSA). Cells are resuspended in 500 μl FACS binding buffer (medium without FCS). 20 μl PGE$_2$-biotinimide is added to the cell suspension and incubated at 4° C. for 1 hour. Cells are washed with washing buffer three times. The cells are resuspended in 500 μl FACS binding buffer and 20 μl SA-RPE is added to the cells and incubated at 4° C. for 30 minutes. Cells are then resuspended in 500 μl FACS binding buffer and the binding of PGE$_2$ on the cell surface is analyzed by flow cytometry. The inhibition of an anti-PGE$_2$ antibody can be determined by pre-incubating the cells with a titration of anti-PGE$_2$ antibody before incubation with PGE$_2$-biotinimide and SA-RPE.

Example 1.2

Generation of Anti-Prostaglandin E$_2$ Monoclonal Antibodies by Hybridoma Approach Anti-prostaglandin E$_2$ mouse monoclonal antibodies were obtained as follows:

Example 1.2.A

Immunization of Mice with a Prostaglandin E$_2$-Thyroglobulin Conjugate

Twenty micrograms of PGE$_2$/thyroglobulin conjugate mixed with complete Freund's adjuvant (Pierce, Rockford, Ill.) or Immunoassay adjuvant (Qiagen, Valencia, Calif.) was injected subcutaneously into five 6-8 week-old Balb/C mice, five C57B/6 mice, and five AJ mice on Day 1. On days 24, 38, and 49, 25 μg of PGE$_2$/thyroglobulin conjugate mixed with incomplete Freund's adjuvant or Immunoassay adjuvant was injected subcutaneously into the same mice. On days 84, 112, or 144, mice were injected intravenously with 1 μg PGE$_2$/thyroglobulin conjugate.

Example 1.2.B

Generation of Hybridomas

Splenocytes obtained from the immunized mice described in Example 1.2.A were fused with SP2/O—Ag-14 cells at a ratio of 5:1 according to the established method described in Kohler, G. and Milstein, Nature, 256:495 (1975) to generate hybridomas. Fusion products were plated in selection media containing azaserine (Pierce, Rockford, Ill.) and hypoxanthine (Pierce, Rockford, Ill.) in 96-well plates at a density of 2.5×10$^6$ spleen cells per well. Seven to ten days post fusion, macroscopic hybridoma colonies were observed. Supernatant from each well containing hybridoma colonies was tested by ELISA (as described in Example 1.1.A) for the presence of antibody to PGE$_2$.

PGE$_2$ was conjugated to several different carrier proteins, including bovine thyroglobulins, keyhole limpet hemocyanin, bovine serum albumin, and ovalbumin. (Amiram, et al. Eur. J. Biochem. 53:145-150 (1975)). Mice were immunized with one of these conjugated PGE$_2$-protein complexes as described in Example 1.2.A. Spleen cells from immunized mice were then fused to generate hybridomas as described in Example 1.2.B. The hybridomas producing antibodies specific for PGE$_2$ were isolated and the antibodies characterized using a biotinylated PGE$_2$ ELISA as described in Example 1.A.

Example 1.2.C

Identification and Characterization of Anti-Prostaglandin E$_2$ Monoclonal Antibodies Hybridomas producing antibodies that bind PGE$_2$, generated according to Examples 1.2.B, were scaled up and cloned by limiting dilution.

Figure 2:
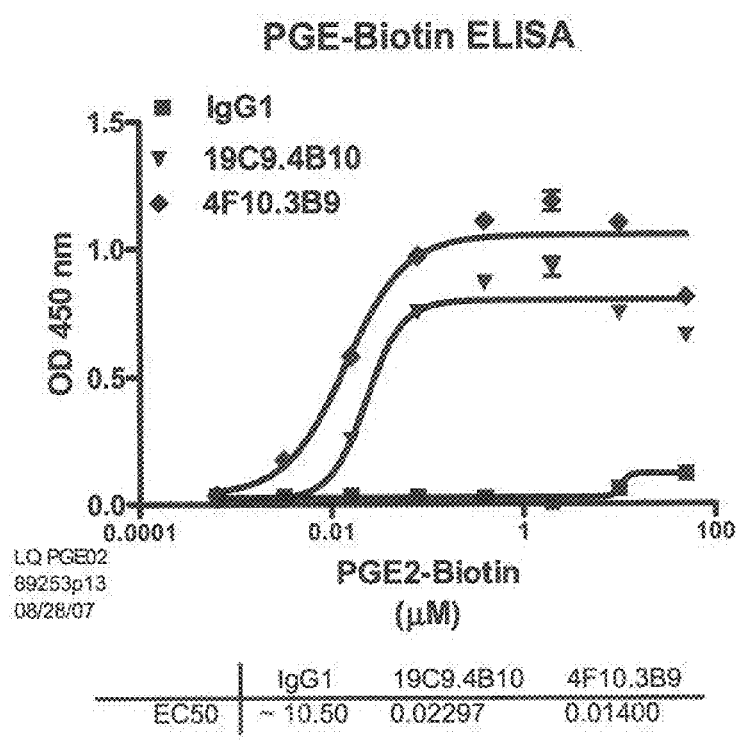
FIG. 2 provides measurement of the binding of two hybridoma derived mAbs 19C9.4B10 and 4F10.3B9 to Biotin-PGE$_2$ in an ELISA described in Example 1.1.A.
Figure 3:
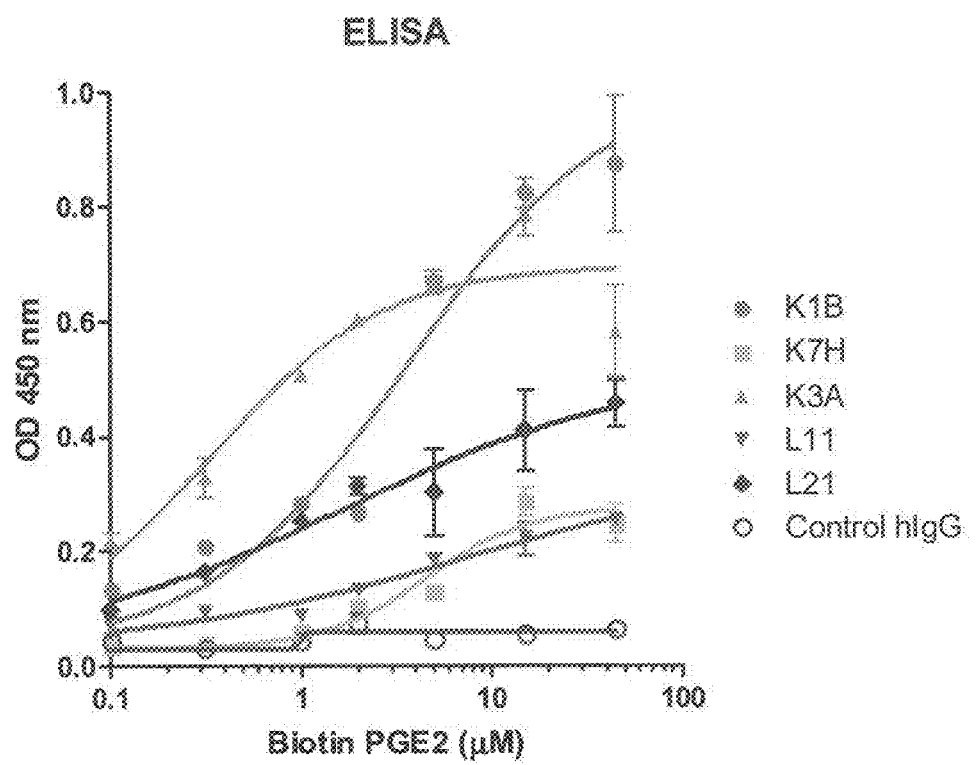
FIG. 3 provides measurement of the binding of PROfusion™ derived mAbs K1B, K7H, K3A, L11 and L21 to Biotin-PGE$_2$ in an ELISA described in Example 1.1.A.
Figure 4:
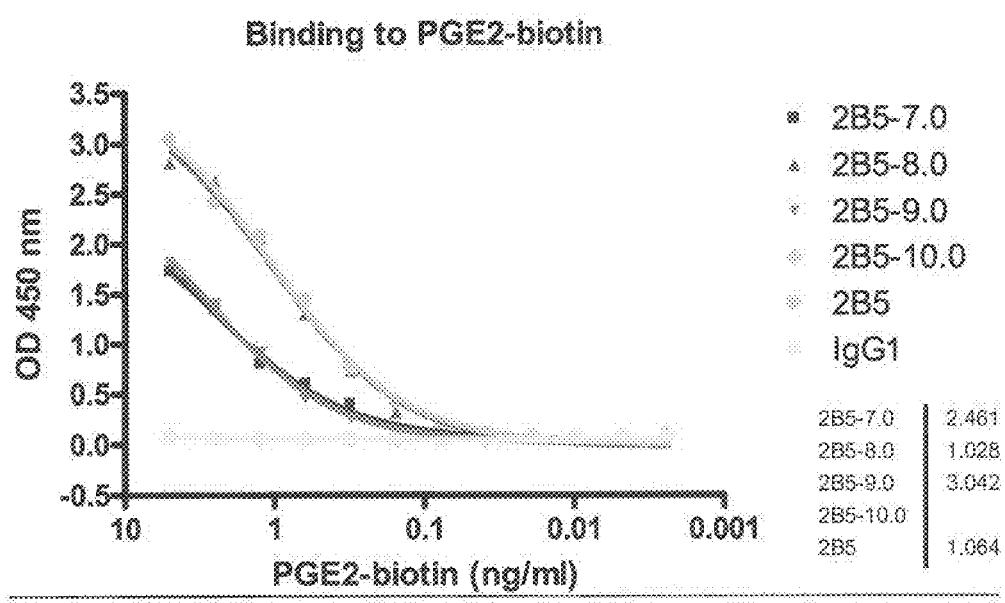
FIG. 4 provides the binding of recombinant anti-PGE$_2$ mAbs 2B5-7.0, 2B5-8.0 and 2B5-9.0 to Biotin-PGE$_2$ in an ELISA described in Example 1.1.A. The hybridoma derived antibody 2B5 is the positive control in this assay.
Figure 5:
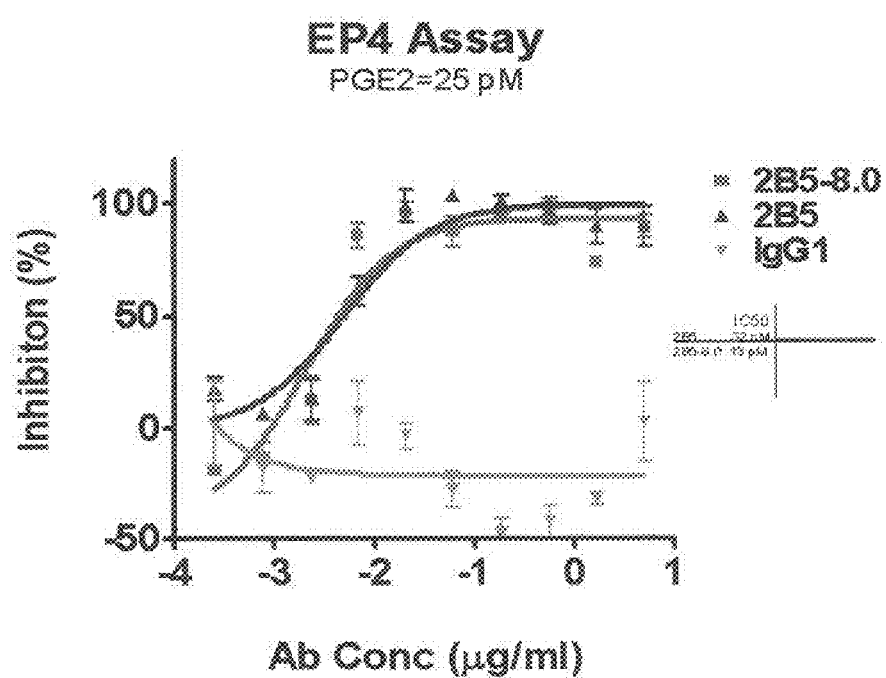
FIG. 5 provides anti-PGE$_2$ mAb 2B5-8.0 to neutralize PGE$_2$ induced Ca$^{++}$ influx in EP4 transfected HEK293 Gα16 stable cell line measured by FLIPR as described in Example 1.1.C 1. The hybridoma derived antibody 2B5 is the positive control in this assay.

Several antibodies, named 19C9, 4F10 and 15F10 specific for PGE$_2$ were isolated. The affinities of these antibodies were determined by ELISA using biotinylated PGE$_2$ as described in Example 1.1.A (FIGS. 1 and 2). The specificity of these antibodies for PGE$_2$ was further determined by a competition ELISA with various prostaglandins as described in Example 1.B (Table 2).

TABLE 2

Affinity and Cross Reactivity of 19C9, 4F10, 15F10, and 2B5 Antibodies

|  | 19C9 | 4F10 | 15F10 | 2B5 |
| --- | --- | --- | --- | --- |
| EC50 (nM) | 16 | 6 | 2 | 0.048 |
|  | 23 | 14 | 5 | 0.033 |
| Cross Reactivity Index | PGE1: <5.6% | PGE1: <3.2% | PGE1: <2.9% | PGE1: ~20% |
|  | PGA2: ~0.1% | PGA2: ~0.1% | PGA2: <0.1% | PGA2: ~0.6% |
|  | PGD2: <0.01% | PGD2: <0.01% | PGD2: <0.01% | PGD2: <0.01% |

Example 2

Human Anti Prostaglandin E$_2$ Antibodies by In Vitro Display Technology

Example 2.1

Human Anti Prostaglandin E$_2$ Antibodies Selected from Non-Immune Human Antibody Libraries by In Vitro Display Technology Using PROfusion™ mRNA display, human anti-PGE$_2$ antibodies were selected from non-immune human antibody libraries by in vitro display technology in the single chain Fv (scFv) format. Antibody amino acid sequences that encoded biotinylated PGE$_2$-binding scFv proteins were collected using streptavidin or neutravidin magnetic beads and further enriched from the libraries by multiple rounds of selection. Bulk output scFv nucleic acid sequences were subcloned into plasmid DNA suitable for bacterial propagation and individual bacterial colonies were picked for scFv sequence analysis and confirmation of their PGE$_2$ binding by the same antigen binding assay used in the library selection. VH and VL DNA of PGE$_2$-binding scFv clones was then separately subcloned into respective human IgG-expressing heavy chain and light chain vectors, and transfected into COS7 cells for IgG expression. The human IgG-containing COS7 media were then used to confirm PGE$_2$ binding by ELISA as described in Example 1.1.A (Table 3).

TABLE 3

Binding of PROfusion Library Derived PGE$_2$ Antibodies To PGE$_2$-Biotinamide (OD$_{450}$)

| Biotin- | Antibody | | | | | | | |
| --- | --- | --- | --- | --- | --- | --- | --- | --- |
| PGE$_2$ (μM) | K1B | K7H | K3A | L11 | L12A | L21 | L20 | Control |
| 45 | 0.88 | 0.24 | 0.58 | 0.07 | 0.26 | 0.46 | 0.12 | 0.07 |
| 15 | 0.82 | 0.29 | 0.78 | 0.07 | 0.22 | 0.41 | 0.09 | 0.05 |
| 5 | 0.67 | 0.13 | 0.67 | 0.07 | 0.18 | 0.31 | 0.07 | 0.05 |
| 2 | 0.27 | 0.10 | 0.61 | 0.07 | 0.13 | 0.32 | 0.06 | 0.08 |
| 1 | 0.29 | 0.06 | 0.51 | 0.05 | 0.09 | 0.25 | 0.06 | 0.05 |
| 0.3 | 0.21 | 0.04 | 0.34 | 0.04 | 0.09 | 0.16 | 0.05 | 0.03 |
| 0.1 | 0.13 | 0.03 | 0.22 | 0.04 | 0.07 | 0.10 | 0.06 | 0.04 |
| 0 | 0.07 | 0.04 | 0.11 | 0.04 | 0.08 | 0.08 | 0.07 | 0.03 |

Table 4 provides a list of amino acid sequences of VH and VL regions of human anti-PGE$_2$ antibodies derived from the PROfusion™ mRNA display library.

TABLE 4

List of Amino Acid Sequences of VH and VL regions

| SEQ ID No. | Protein region | Sequence 12345678901234567890123456789 0 |
|---|---|---|
| 5 | VH PGE2LNK1B | EVQLVQSGAEVKRPGASVKVSCKTSGYTFTNYDINWVRLAPGQGLEWMGCMNPTTGKTGYAQKFQGRVTMTRDTTIATAYMELSRLTSEDTAVYYCARGRGYSPGYGVAYADYWGQGTTNTVSS |
| 6 | VH PGE2:LN1B CDR-H1 | Residues 31-35 of SEQ ID NO.: 5 — NYDIN |
| 7 | VH PGE2LNK1B CDR-H2 | Residues 50-66 of SEQ ID NO.: 5 — CMNPTTGKTGYAQKFQG |
| 8 | VH PGE2LNK1B CDR-H3 | Residues 99-113 of SEQ ID NO.: 5 — GRGYSPGYGVAYADY |
| 9 | VL PGE2LNK1B | DIQLTQSPSSLPASVGDRVTITCRASQSISTYLNWYQQTPGKAPSLLIYAASSLQSGVPSRFSGSGSGTDFTLTISSLQPEDFATYYCQQSYSPPPTFGGGTKVEIKR |
| 10 | VL PGE2LNK1B CDR-L1 | Residues 24-34 of SEQ ID NO.: 9 — RASQSISTYLN |
| 11 | VL PGE2LNK1B CDR-L2 | Residues 50-56 of SEQ ID NO.: 9 — AASSLQS |
| 12 | VL PGE2LNK1B CDR-L3 | Residues 89-97 of SEQ ID NO.: 9 — QQSYSPPPT |
| 13 | VH PGE2LNK3A | EVQLVQSGAETKKPGASVEVSCKASGYSFTEYGISWVRQAPGQGPEWMGCISPYNGKLHYAQEFQGRVTMTTGTSTNTAYMELGSLRSDDTAVYYCARGGFSFYDSSGYYYVTDHWGQGTLVTVSS |
| 14 | VH PGE2LNK3A CDR-H1 | Residues 31-35 of SEQ ID NO.: 13 — EYGIS |
| 15 | VH PGE2LNK3A CDR-H2 | Residues 50-66 of SEQ ID NO.: 13 — CISPYNGKLHYAQEFQG |
| 16 | VH PGE2LNK3A CDR-H3 | Residues 99-115 of SEQ ID NO.: 13 — GGFSFYDSSGYYYVTDH |
| 17 | VL PGE2LNK3A | DIRLTQSPSSLSASVGDRVTITCRASQSIGSYLNWYQQKSGKAPKLLIYAASKLQSGVPSRFSGSGFGTDFTLTISSLQPEDSATYYCQQSDTTPFTFGQGIKLEIKR |
| 18 | VL PGE2LNK3A CDR-L1 | Residues 24-34 of SEQ ID NO.: 17 — RASQSIGSYLN |
| 19 | VL PGE2LNK3A CDR-L2 | Residues 50-56 of SEQ ID NO.: 17 — AASKLQS |
| 20 | VL PGE2LNK3A CDR-L3 | Residues 89-97 of SEQ ID NO.: 17 — QQSDTTPFT |
| 21 | VH PGE2LNK7H | EVQLVQSGSELKKPGASVKVSCKVSGYSFTEYGISWVRQAPGQGPEWNGCISPYNGKLHYAQKFLGRVTMTDTSTNTAYMELRSLKSDDTAVYYCARGGFSSYDSSGYYYVTDHWGQGTLVTVSS |
| 14 | VH PGE2LNK7H CDR-H1 | Residues 31-35 of SEQ ID NO.: 21 — EYGIS |
| 22 | VH PGE2LNK7H CDR-H2 | Residues 50-66 of SEQ ID No.: 21 — CISPYNGKLHYAQKFLG |
| 23 | VH PGE2LNK7H CDR-H3 | Residues 99-115 of SEQ ID NO.: 21 — GGFSSYDSSGYYYVTDH |

TABLE 4-continued

List of Amino Acid Seiuences of VH and VL regions

| SEQ ID No. | Protein region | Sequence Residues | 12345678901234567890123456789 0 |
|---|---|---|---|
| 24 | VL PGE2LNK7H | | DIRLTQSPSSLPASVGDRVTITCRASQSIS TYLNWYQQTPGKAPSLLIYAASSLQSGVPS RFSGSGSGTDFTLTISSLQPEDFATYYCQQ SYSPPPTFGGGTKVEIKR |
| 10 | VL PGF2LNK7H CDR-L1 | Residues 24-34 of SEQ ID NO.: 24 | RASQSISTYLN |
| 11 | VL PGE2LNK7H CDR-L2 | Residues 50-56 of SEQ ID NO.: 24 | AASSLQS |
| 12 | VL PGE2LNK7H CDR-L3 | Residues 89-97 of SEQ ID NO.: 24 | QQSYSPPPT |
| 25 | VH PGE2LNL11 | | EVQLVQSGPELKKPGTS-VKVSCKASGYTLT TYAMNWVRQAPGQGLEWMGWIDTSTGNPTY APGFLGRFVFSLDTSLSTTYLQISSLKPDD TAVYYCARSSHTRPGDFWGQGTLVTVSS |
| 26 | VH PGE2LNL11 CDR-H1 | Residues 31-35 of SEQ ID NO.: 25 | TYAMN |
| 27 | VH PGE2LNL11 CDR-H2 | Residues 50-66 of SEQ ID NO.: 25 | WIDTSTGNPTYAPGFLG |
| 28 | VH PGE2LNL11 CDR-H3 | Residues 99-113 of SEQ ID No.: 25 | SSHTRPGDF |
| 29 | VL PGE2LNL11 | | QSGLTQPPSVSGTPGQRVTISCSGSESNVG TNSVNWYQQLPGAAPRLLIRGNSDRPSGVP DRFSASKSGTSASLAISRLQSEDEADYFCG ACDGRLSGLYVFGTGTKVTVL |
| 30 | VL PGE2LNL11 CDR-L1 | Residues 23-35 of SEQ ID NO.: 29 | SGSESNVGTNSVN |
| 31 | VL PGE2LNL11 CDR-L2 | Residues 51-56 of SEQ ID NO.: 29 | GNSDRP |
| 32 | VL PGE2LNL11 CDR-H3 | Residues 90-107 of SEQ ID | GACDGRLSGLYV |
| 33 | VH PGE2LNL21 | | EVQLVQSGSELKKPGTSVKVSCKASGYTLT TYAMNWVRQAPGQGLEWNGWIGTSTGNPTY AQGFTGRFVFSLDTSVNTAHLQIYSLKAED TALYYCARSSLTRPADYWGQGTLVTVSS |
| 26 | VH PGE2LNL21 CDR-H1 | Residues 31-35 of SEQ ID NO.: 33 | TYAMN |
| 34 | VH PGE2LNL21 CDR-H2 | Residues 50-66 of SEQ ID NO.: 33 | WIGTSTGNPTYAQGFTG |
| 35 | VH PGE2LNL21 CDR-H3 | Residues 99-107 of SEQ ID NO.: 33 | SSLTRPADY |
| 36 | VL PGE2LNL21 | | QSGLTQPPSVSGAPGQRVTISCFGSSSNIG AGYDVHWYQQLPGAAPKLLIFGNNNRPSGV PDRFSGSKSGTSASLATTGLQAEDEADYYC QSCDSSLSGAVFGTGTKVTVL |
| 37 | VL PGE2LNL21 CDR-L1 | Residues 23-36 of SEQ ID NO.: 36 | FGSSSNIGAGYDVH |
| 38 | VL PGE2LNL21 CDR-L2 | Residues 52-57 of SEQ ID NO.: 36 | GNNNRP |
| 39 | VL PGF2LNL21 CDR-L3 | Residues 91-101 of SEQ ID NO.: 36 | QSCDSSLSGAV |

Example 3

Generation and Characterization of Recombinant Anti Prostaglandin E₂ Antibodies According to Solved Protein Sequence by a Combination of Edman Sequencing, Mass Spectrum Analysis and BLAST The protein sequence of hybridoma-derived mouse antibodies specific for $PGE_2$ was generated by analyzing amino acid sequences using a combination of Edman degradation, mass spectrum analysis and BLAST (Basic Local Alignment Search Tool, NCBI, NIH, Bethesda, Md.) as described previously (Pham, V. et al. Analyt. Biochem. 352:77-86 (2006)). 0.45 mg of anti-$PGE_2$ antibody was reduced with 100 mM DTT (Invitrogen, Carlsbad, Calif.) to light chain and heavy chain. The light chains and heavy chains of the anti-$PGE_2$ antibodies were separated by reverse phase HPLC on Shimadzu HPLC system (Shimadzu Scientific Instruments, Columbia, Md.) with a Vydac C-18 reverse phase column (H-P Separations Group, Hesperia, Calif.). The molecular weights of the light and heavy chains were measured on the Applied Biosystems API QSTAR Pulsar i mass spectrometer (Applied Biosystems, Foster City, Calif.) and Agilent Q-TOF mass spectrometer (Agilent, Palo Alto, Calif.). N terminal sequencing of the light chains was performed in solution on PE Applied Biosystems 494/785A/140C/610A Protein-Peptide Sequencer (Applied Biosystems, Foster City, Calif.). 45 uL of light chain of the anti-PGE2 2B5 antibody was loaded on the center of the filter and 42 cycles were performed. The N-terminal of heavy chain of the anti-$PGE_2$ antibody was blocked with pyroglutamic acid and it could not be sequenced directly by Edman degradation. Prior to N-terminal Edman sequencing the heavy chain, the heavy chain N terminal was de-blocked using pyroglutamate aminopeptidase (Sigma, St. Louis, Mo.). 80 µg of anti-$PGE_2$ antibody was reduced with 50 mM DTT at 37° C. for 30 minutes. 0.42 µl of 0.5 M EDTA, pH 7.5 (Invitrogen, Carlsbad, Calif.) was added to the reduced sample to a final EDTA concentration of 1 mM. 50 µl reconstituted recombinant *pyrococcus furiosus* pyroglutamate aminopeptidase (Sigma, St. Louis, Mo.) was added to the sample. After incubating the sample solution at 40° C. for 15 hours, the temperature was increased to 60° C. for an additional two hours. An additional 10 µl of the reconstituted *pyrococcus furiosus* pyroglutamate aminopeptidase was added and the sample was incubated at 60° C. for an additional hour. 4 µl of the sample was used for LC/MS analysis at 15 hour, 17 hour, and 18 hour time points to monitor the extent of the de-blocking process. When the de-blocking reaction was complete, the solution was concentrated by speed-vacuum (Eppendorf, Westbury, N.Y.) to about 100 µl. The de-blocked heavy chain was separated from light chain by SDS-PAGE and then transferred to PVDF membrane (Invitrogen, Carlsbad, Calif.) for Edman Sequencing (Niall, H D, Methods Enzymol. 27:942-1010 (1973)).

To obtain the internal peptide sequence of an anti-$PGE_2$ antibody, the antibody was digested with multiple proteases with or without alkylation treatment. The sample was first reduced with DTT. The reduced sample was either digested directly with a protease or alkylated with iodoacetamide (Sigma, St. Louis, Mo.) before digestion. Proteases used in this study include trypsin, glu-C, asp-N and chymotrypsin (Sigma, St. Louis, Mo.). Fractions of protease digested peptides were separated by HPLC and each fraction was collected in a separate eppendorf tube for either MS or Edman sequencing. For LC/MS/MS analysis, MALDI-MS (Applied Biosystems, Foster City, Calif.), nano-LC/ESI-MS/MS (Applied Biosystems, Foster City, Calif.) with either LCQ-deca, API QStar Pulsar (Applied Biosystems, Foster City, Calif.) and Agilent Q-TOF (Agilent, Palo Alto, Calif.) were used. HPLC conditions were mobile Phase A=0.1% Formic acid; mobile Phase B=80% ACN/20% 0.1% Formic acid. A 1-3 hour gradient (5-50% B) was applied. For Edman sequencing, the fractions containing peptides resulting from protease digestion were transferred to PVDF membrane by a ProSorb cartridge (Applied Biosystems, Foster City, Calif.). Each fraction was diluted to 100 µl of 0.1% TFA solution (Sigma, St. Louis, Mo.). After wetting the PVDF membrane (Invitrogen, Carlsbad, Calif.) in the reservoir with 10 µl methanol (Sigma, St. Louis, Mo.), the sample was added to the reservoir. The sample was removed from the reservoir and the PVDF membrane was air dried. The PVDF membrane was punched out, 5 µl of 10% diluted Biobrene solution (Sigma, St. Louis, Mo.) was added and the membrane dried completely. After washing the PVDF membrane with 15 µl 0.1% TFA for 15 seconds, the surface was wiped with filter paper. 4 µl of methanol was added to the PVDF membrane and allowed to dry thoroughly. The dried PVDF membrane was used for Edman Sequencing.

Germline sequences of the VH and VL of an anti-$PGE_2$ antibody were determined by alignment of the solved variable regions of heavy chain and light chain according to the above methods with the VH and VL database of mouse germline sequences (Ig-BLAST, NCBI, NIH, Bethesda, Md.). For the regions unsolved by MS and Edman sequencing, the closest germline sequence was assigned. The possible hot spot mutations were identified manually to match the experimental molecular weight of the heavy chain and light chain of an anti-$PGE_2$ antibody determined by MS respectively. The protein sequence of an anti-$PGE_2$ antibody was solved using the above method.

Several versions of the recombinant anti-$PGE_2$ antibodies (2B5-7.0, 2B5-8.0 and 2B5-9.0) were constructed based on this solved protein sequence, each having different residues in a few unsolved positions (Table 5). The testing of these recombinant antibodies is described in Example 4. Although the amino acid sequence of antibody CDRs are critical for binding specificity, potency and affinity of the antibody, substitutions, alterations, deletions or additions of a few residues in the frameworks and even CDRs may still largely maintain the binding specificity, potency, and affinity of an antibody. A version of an antibody with at least one or a few such substitution(s), alterations, deletions or additions is still within the scope of the invention. An alignment of VH and VL regions of anti-$PGE_2$ antibodies (2B5-7.0, 2B5-8.0 and 2B5-9.0) is shown in FIG. 8.

TABLE 5

Several Versions Of The Solved Protein Sequences For A Mouse Anti-PGE₂ Antibody

| SEQ ID No. | Protein region | Sequence<br>123456789012345678901234567890 |
|---|---|---|
| 40 | VH 2B5-7.0 | QVQLQQSGPELVRPGSSVKISCKASGYTFTK<br>YWLGWVKQRPGHGLEWIGDIYPGYDYTHYNE<br>KFKDKATLTVDTSSSTAYMQLSSLTSEDSAV<br>YFCARSDGSSTYWGQGTLVTVSA |
| 41 | VL 2B5-7.0 | DVLMTQTPLSLPVSLGDQASISCTSSQNIVH<br>SNGNTYLEWYLQRPGQSPKLLIYKVSNRFSG<br>VPDRFSGSGSGTVFTLKISRVEAEDLGVYYC<br>FQVSHVPYTFGGGTKLEIKR |

TABLE 5-continued

Several Versions Of The Solved Protein Sequences For A Mouse Anti-PGE$_2$ Antibody

| SEQ ID No. | Protein region | Sequence 1234567890123456789012345678 90 |
|---|---|---|
| 42 | VH 2B5-8.0 | QVQLQQSGPELVRPGSSVKISCKASGYTFTK YWLGWVKQRPGHGLEWTGDIYPGYDYTHYNE KFKDKATLTVDTSSSTAYMQLSSLTSEDSAI YYCARSDGSSTYWGQGTLVTVSA |
| 43 | VL 2B5-8.0 | DVLMTQTPLSLPVSLGDQASISCTSSQNIVH SNGNTYLEWYLQRPGQSPKLLIYKVSNRFSG VPDRFSGSGSGTVFTLKISRVEAEDLGVYYC FQVSHVPYTFGGGTKLEIKR |
| 44 | VH 2B5-9.0 | QVQLQQSGPELVRPGSSVKISCKASGYTFTK YWLGWVKQRPGHGLEWIGDIYPYGDYTHYNE KFKDKATLTVDTSSSTAYMQLSSLTSEDSAV YFCARSDGSSTYWGQGTLVTVSA |
| 45 | VL 2B5-9.0 | DVLMTQTPLSLPVSLGDQASISCTSSQNIVH SNGNTYLEWYLQRPGQSPKLLIYKVSNRFSG VPDRFSGSGSGTVFTLKISRVEAEDLGVYYC FQVSHVPYTFGGGTKLEIKR |

Example 4

Recombinant Anti-Prostaglandin E$_2$ Antibodies

Example 4.1

Construction and Expression of Recombinant Anti-Prostaglandin E$_2$ Antibodies

DNA encoding the heavy chain variable regions of mouse anti-PGE2 antibodies 2B5-7.0, 2B5-8.0 or 2B5-9.0 was fused to a cDNA fragment encoding either a human IgG1 constant region, a mouse IgG1 constant, or a mouse IgG2a constant region by homologous recombination in bacteria. (Zhang, Y et al. Nature Biotechnol. 18(12):1314-7 (2000)). DNA encoding the light chain variable regions of 2B5-7.0, 2B5-8.0 or 2B5-9.0 was fused to a human kappa constant region or mouse kappa constant region. Id. Full-length antibodies were transiently expressed in 293 cells by co-transfection of heavy and light chain cDNAs ligated into the pTT3 expression plasmids. (Durocher, Y et al. Nucleic Acids Res. 30(2):E9 (2002)). Cell supernatants containing recombinant chimeric antibody were purified by Protein A Sepharose chromatography and bound antibody was eluted by addition of acid buffer. Antibodies were neutralized and dialyzed into PBS. (Making and Using Antibodies: A Practical Handbook. Edited by Gary C. Howard and Matthew R. Kaser. Published by CRC (2006)).

The purified chimeric anti-PGE$_2$ monoclonal antibodies 2B5-7.0, 2B5-8.0 and 2B5-9.0 were then tested for their ability to bind to PGE$_2$ in an ELISA assay as described in Example 1.1.A (Table 6) and for their selectivity in a competition ELISA as described in Example 1.1.B (Table 6). All three recombinant anti-PGE$_2$ monoclonal antibodies 2B5-7.0, 2B5-8.0 and 2B5-9.0 potently bound to PGE$_2$ with a similar specificity for PGE$_2$. 2B5-8.0 demonstrated the highest binding ability to PGE$_2$ and was selected for further characterization in an EP4 bioassay to characterize its ability to neutralize PGE$_2$ bioactivity and in a $^3$H-PGE$_2$ competition ELISA to characterize its prostaglandin selectivity using a full panel of prostaglandins. 2B5-8.0 potently inhibited PGE$_2$ induced calcium influx in the EP4 bioassay as described in Examples 1.1. C (Table 6).

TABLE 6

Characterization Of PGE$_2$ Binding, Prostaglandin Binding Selectivity And PGE$_2$ Neutralization Potency Of Engineered Anti-PGE$_2$ Mabs

| Anti-PGE$_2$ mAb | | 2B5 | 2B5-7.0 | 2B5-8.0 | 2B5-9.0 |
|---|---|---|---|---|---|
| PGE$_2$ binding in Biotin-PGE$_2$ ELISA (EC50, nM) | | 2.99 | 2.46 | 1.03 | 3.04 |
| PG Selectivity in | PGE$_1$ | 41 | 27 | 28 | 23 |
| Biotin-PGE$_2$ | PGA$_2$ | 0.29 | 0.11 | 0.21 | 0.24 |
| Competition ELISA (CRI %) | PGD$_2$ | <0.01 | <0.01 | <0.01 | <0.01 |
| PGE$_2$ binding in $^3$H-PGE$_2$ ELISA (EC50, pM) | | 315 | | 253 | |
| PG Selectivity | PGE2 | 100 | | 100 | |
| in $^3$H-PGE$_2$ | PGE1 | 12 | | 3.6 | |
| competition | PGA2 | 0.17 | | 0.04 | |
| ELISA | PGD2 | 0.04 | | $<1 \times 10^{-4}$ | |
| (CRI %) | PGF2α | 0.25 | | 0.05 | |
| | PGI2 | NA | | 0.16 | |
| | Iloprost | NA | | 0.01 | |
| | Carbaprostacyclin | NA | | 0.18 | |
| | Pinane TXA2 | NA | | 0.00033 | |
| | 15R-Pinane TXA2 | NA | | 0.00043 | |
| | Carbocyclic TXA2 | NA | | 0.0005 | |
| | TXB2 | <0.01 | | <0.01 | |
| | 6-keto PGF1α | 0.4 | | 0.64 | |
| | PGB2 | 0.03 | | 0.00038 | |
| | 8-iso PGF2α | 0.02 | | 0.092 | |
| | 13,14-dihydroxyl-15-keto PGE2 | <0.01 | | 0.012 | |
| | 2,3-dinor-6-keto-PGF1α | NA | | 0.019 | |
| | 15-keto PGE2 | <0.01 | | 0.013 | |
| | 19R-hydroxy PGE2 | <0.01 | | 0.09 | |

TABLE 6-continued

Characterization Of PGE$_2$ Binding, Prostaglandin Binding Selectivity And PGE$_2$ Neutralization Potency Of Engineered Anti-PGE$_2$ Mabs

| Anti-PGE$_2$ mAb | 2B5 | 2B5-7.0 | 2B5-8.0 | 2B5-9.0 |
|---|---|---|---|---|
| LTE4 | <0.01 | | 0.012 | |
| 5(S)-HETE | <0.01 | | <0.01 | |
| Arachidonic acid | <0.01 | | <0.01 | |
| PGE$_2$ Neutralization Potency in Cellular EP4 assay (IC50, pM) | 38 | | 44 | |

Example 4.2

Construction and Expression of Humanized Anti-Prostaglandin E$_2$ Antibodies

Example 4.2.1

Selection of Human Antibody Frameworks

Humanization was based on amino acid sequence homology, CDR cluster analysis, frequency of use among expressed human antibodies, and available information on the crystal structures of human antibodies. Taking into account possible effects on antibody binding, VH-VL pairing, and other factors, murine residues were mutated to human residues where murine and human framework residues were different, with a few exceptions. Additional humanization strategies were designed based on an analysis of human germline antibody sequences, or a subgroup thereof, that possessed a high degree of homology, i.e., sequence similarity, to the actual amino acid sequence of the murine antibody variable regions.

Homology modeling was used to identify residues unique to the murine antibody sequences that are predicted to be critical to the structure of the antibody CDRs. A reference protein sharing sequence similarity to the target protein of interest and for which three dimensional coordinates are known was used to obtain initial coordinates and guidance for their further refinement. The primary sequences of the reference and target proteins are aligned such that coordinates of identical portions of the two proteins are aligned. Coordinates for mismatched portions of the two proteins, e.g., from residue mutations, insertions, or deletions, are constructed from generic structural templates and energy refined to insure consistency with the already aligned model coordinates. This computational protein structure may be further refined or employed directly in modeling studies.

The murine variable heavy and variable light chain gene sequence of 2B5-8.0 was separately aligned against 44 human immunoglobulin germline variable heavy chain or 46 germline variable light chain sequences (derived from NCBI Ig BlAST website at http://www.ncbi.nlm.nih.gov/igblast/retrieveig.html.) using Vector NTI software. A combination of BLAST searching and visual inspection was used to identify suitable reference structures. Sequence identity of 25% between the reference and target amino acid sequences is considered the minimum necessary to attempt a homology modeling exercise. Sequence alignments were constructed manually and model coordinates were generated with the program Jackal (Petrey, D., et al. Proteins 53 (Suppl. 6):430-435 (2003)). For 2B5-8.0 humanization, based on a homology search against human V and J segment sequences, the VH segment VH1-18 and the J segment JH4 were selected to provide the frameworks for the humanized heavy chain variable region for 2B5-8.0. For the 2B5-8.0 light chain variable region, the VL segment 01 and the J segment JK4 were used (see Tables 7 and 8). The identity of the framework amino acids between 2B5-8.0 VH and the acceptor human VH1-18 and JH4 segments was 80.2%, while the identity between 2B5-8.0 VL and the acceptor human 01 and JK4 segments was 90.3%. Although a specific pair of preferred human framework acceptors VH/JH and VL/JK was selected as acceptors for humanization of 2B5-8.0, it is known in the art that other human framework acceptors with sequence identity of minimum 25% to mouse framework can also be used for humanization of 2B5-8.0 and are therefor within the scope of this invention.

TABLE 7

Heavy Chain Acceptor Sequences For 2B5-8.0 Humanization

| SEQ ID No. | Protein | region | Sequence 123456789012345678901234567890012 |
|---|---|---|---|
| 46 | VH1-18&JH4 | FR1 | QVQLQQSGPELVRPGSSVKISCKAS |
| 47 | VH1-18&JH4 | FR2 | WVKQRPGHGLEWIG |
| 48 | VH1-18&JH4 | FR3 | KATLTVDTSSSTAYMQLSSLTSEDSAIYYCAR |
| 49 | VH1-18&JH4 | FR4 | WGQGTLVTVSA |

TABLE 8

Light Chain Acceptor Sequences For 2B5-8.0 Humanization

| SEQ ID No. | Protein | region | Sequence 123456789012345678901234567890012 |
|---|---|---|---|
| 50 | Q1&JK4 | FR1 | DVLMTQTPLSLPVSLGDQASISC |
| 51 | Q1&JK4 | FR2 | WYLQRPGQSPKLLIY |
| 52 | Q1&JK4 | FR3 | VPDRFSGSGSGTVFTLKISRVEAEDLGVYYC |
| 53 | Q1&JK4 | FR4 | FGGGTKLEIKR |

The primary sequences of the murine and human framework regions of the selected antibodies share significant identity. Residue positions that differed were candidates for inclusion of the murine residue in the humanized sequence in order to retain the observed binding potency of the murine antibody. Such framework region amino acid substitutions (human residues that are back mutated to mouse residues) at a key residue are called framework back mutations, wherein the key residue is selected from the group consisting of a residue adjacent to a CDR; a glycosylation site residue; a rare residue; a residue capable of interacting with PGE2; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. In an embodiment, the human acceptor framework comprises at least one Framework Region amino acid substitution, wherein the amino acid sequence of the framework is at least 65% identical to the sequence of the human acceptor framework and comprises at least 70 amino acid residues identical to the human acceptor framework. For humanization of 2B5-8.0, the framework region amino acid substitution at a key residue is selected from the group consisting of M (human) to I (mouse) at position 48, V (human) to A (mouse) at position 68, M (human) to L (mouse) at position 70, and T (human) to V (mouse) at position 72 in the heavy chain variable region; and I (human) to V (mouse) at position 2 and V (human) to L (mouse) at position 3 in the light chain variable region.

The likelihood that a given framework residue would impact the binding properties of the antibody depends on its proximity to the CDR residues. Therefore, using the model structures, the residues that differ between the murine and human sequences were ranked according to their distance from any atom in the CDRs that likely contact $PGE_2$. Those residues that fell within 4.5 Å of any CDR atom were identified as most important and were deemed candidates for retention of the murine residue in the humanized antibody (i.e., frame work back mutation).

For humanization of the 2B5-8.0 antibody variable regions, the general approach provided in the present invention was as follows. First, a molecular model of the 2B5-8.0 antibody variable regions was constructed with the aid of the computer programs ABMOD and ENCAD (Levitt, M., J. Mol. Biol. 168: 595-620 (1983)). Next, based on a homology search against human V and J segment sequences, the VH segment VH1-18 (The Immunoglobulin Facts Book. 2001, authored by Marie-Paule Lefranc and Gerald Lefranc, published by Academic Press) and the J segment JH4 (Id.) were selected to provide the frameworks for the humanized heavy chain variable region for 2B5-8.0. For the 2B5-8.0 light chain variable region, the VL segment 01 (Id.) and the J segment JK4 (Id.) were used. The identity of the framework amino acids between 2B5-8.0 VH and the acceptor human VH1-18 and JH4 segments was 80.2%, while the identity between 2B5-8.0 VL and the acceptor human 01 and JK4 segments was 90.3%. The computer model did not identify any significant contact residues with the CDRs that need to be back mutated. No further replacements were done.

Nine different versions of humanized 2B5-8.0, named as HU2B5.1, HU2B5.2, HU2B5.3, HU2B5.4, HU2B5.5, HU2B5.6, HU2B5.7, HU2B5.8 and HU2B5.9, were designed. The nine antibodies were different in the framework back mutations at positions 48, 68, 70, and 72 in the heavy chain variable region and positions 2 and 3 in the light chain variable region as described above.

TABLE 9

CDRs of Mouse Anti-$PGE_2$ Antibody 2B5-8.0

| SEQ ID No. | Protein region | Sequence 12345678901234567890123456789012 |
|---|---|---|
| 54 | CDR H1 | GYTFTKYWLG |
| 55 | CDR-H2 | DIYPGYDYTHYNEKFKD |
| 56 | CDR-H3 | SDGSSTY |

TABLE 9-continued

CDRs of Mouse Anti-$PGE_2$ Antibody 2B5-8.0

| SEQ ID No. | Protein region | Sequence 12345678901234567890123456789012 |
|---|---|---|
| 57 | CDR-L1 | TSSQNIVHSNGNTYLE |
| 58 | CDR-L2 | KVSNRFSG |
| 59 | CDR-L3 | FQVSHVPYT |

TABLE 10

Nine Humanized Anti-$PGE_2$ Antibodies With CDRs of 2B5-8.0

| SEQ ID No. | Protein region | Sequence 12345678901234567890123456789012 |
|---|---|---|
| 60 | VH Hu2B5.1 | EVQLVQSGAEVKKPGASVKVSCKASGYTFT KYWLGWVRQAPGQGLEWIGDIYPGYDYTHY NEKFKDRATLTVDTSTSTAYMELRSLRSDD TAVYYCARSDGSSTYWGQGTLNTVSS |
| 61 | VL HU2B5.1 | DVVMTQTPLSLPVTPGEPASISCTSSQNIV HSNGNTYLEWYLQKPGQSPQLLIYKVSNRF SGVPDRFSGSGSGTDFTLKISRVEAEDVGV YYCFQVSHVPYTFGGGTKVEIKR |
| 62 | VH HU2B5.2 | EVQLVQSGAEVKKPGASVKVSCKASGYTFT KYWLGWVRQAPGQGLEWIGDIYPGYDYTHY NEKFKDRATLTVDTSTSTAYMELSSLRSDD TAVYYCARSDGSSTYWGQGTLNTVSS |
| 63 | VL HU2B5.2 | DVVMTQTPLSLPVTPGEPASISCTSSQNIV HSNGNTYLEWYLQKPGQSPQLLIYKVSNRF SGVPDRFSGSGSGTDFTLKISRVEAEDVGV YYCFQVSHVPYTFGGGTKVEIKR |
| 64 | VH HU2B5.3 | EVQLVQSGAEVKKPGASVKVSCKASGYTFT KYWLGWVRQAPGQGLEWTGDIYPGYDYTHY NEKFKDRATLTVDTSTSTAYMELRSLRSDD TAVYYCARSDGSSTYWGQGTLVTVSS |
| 65 | VL HU2B5.3 | DVLMTQTPLSLPVTPGEPASISCTSSQNIV HSNGNTYLEWYLQKPGQSPQLLIYKVSNRF SGVPDRFSGSGSGTDFTLKISRVEAEDVGV YYCFQVSHVPYTFGGGTKVEIKR |
| 66 | VH HU2B5.4 | EVQLVQSGAEVKKPGASVKVSCKASGYTFT KYWLGWVRQAPGQGLEWIGDIYPGYDYTHY NEKFKDRATLTVDTSTSTAYMFLSSLRSDD TAVYYCARSDGSSTYWGQGTLVTVSS |
| 67 | VL HU2B5.4 | DVLMTQTPLSLPVTPGEPASISCTSSQNIV HSNGNTYLEWYLQKPGQSPQLLIYKVSNRF SGVPDRFSGSGSGTDFTLKISRVEAEDVGV YYCFQVSHVPYTFGGGTKVEIKR |
| 68 | VH HU2B5.5 | EVQLVQSGAEVKKPGASVKVSCKASGYTFT KYWLGWVRQAPGQGLEWMGDIYPGYDYTHY NEKFKDRVTLTTDTSTSTAYMELRSLRSDD TAVYYCARSDGSSTYWGQGTLVTVSS |
| 69 | VLHU2B5.5 | DVVMTQTPLSLPVTPGEPASISCTSSQNIV HSNGNTYLEWYLQKPGQSPQLLIYKVSNRF SGVPDRFSGSGSGTDFTLKISRVEAEDVGV YYCFQVSHVPYTFGGGTKVEIKR |
| 70 | VHHU2B5.6 | EVQLVQSGAEVKKPGASVKVSCKASGYTFT KYWLGWVRQAPGQGLEWNGDIYPGYPYTHY NEKFKDRVTLTTDTSTSTAYMELSSLRSDD TAVYYCARSDGSSTYWGQGTLVTVSS |

TABLE 10-continued

Nine Humanized Anti-PGE$_2$
Antibodies With CDRs of 2B5-8.0

| SEQ ID No. | Protein region | Sequence<br>123456789012345678901234567890 |
|---|---|---|
| 71 | VLHU2B5.6 | DVVMTQTPLSLPVTPGEPASISCTSSQNIV<br>HSNGNTYLEWYLQKPGQSPQLLIYKVSNRF<br>SGVPDRFSGSGSGTDFTLKISRVEAEDVGV<br>YYCFQVSHVPYTFGGGTKVEIKR |
| 72 | VHHU2B5.7 | EVQLVQSGAEVKKPGASVKVSCKASGYTFT<br>KYWLGWVRQAPGQGLEWMGDIYPGYDYTHY<br>NEKFKDRVTLTTDTSTSTAYMELRSLPSDD<br>TAVYYCARSDGSSTYWGQGTLVTVSS |
| 73 | VL HU2B5.7 | DVLMTQTPLSLPVTPGEPASISCTSSQNIV<br>HSNGNTYLEWYLQKPGQSPQLLIYKVSNRF<br>SGVPDRFSGSGSGTDFTLKISRVEAEDVGV<br>YYCFQVSHVPYTFGGGTKVEIKR |
| 74 | VH HU2B5.8 | EVQLNQSGAEVKKPGASVKVSCKASGYTFT<br>KYWLGWVRQAPGQGLEWMGDIYPGYDYTHY<br>NEKFKDRVTLTTDTSTSTAYMELSSLRSDD<br>TAVYYCARSDGSSTYWGQGTLVTVSS |
| 75 | VL HU2B5.8 | DVLMTQTPLSLPVTPGEPASISCTSSQNIV<br>HSNGNTYLEWYLQKPGQSPQLLIYKVSNRF<br>SGVPDRFSGSGSGTDFTLKISRVEAEDVGV<br>YYCFQVSHVPYTFGGGTKVEIKR |
| 76 | VH HU2B5.9 | EVQLNQSGAEVKKPGASVKVSCKASGYTFT<br>KYWLGWVRQAPGQGLEWMGDIYPGYDYTHY<br>NEKFKDRVTMTTDTSTSTAYMELRSLRSDD<br>TAVYYCARSDGSSTYWGQGTLVTVSS |
| 77 | VL HU2B5.9 | DIVMTQTPLSLPVTPGEPASISCTSSQNIV<br>HSNGNTYLEWYLQKPGQSPQLLIYKVSNRF<br>SGVPDRFSGSGSGTDFTLKISRVEAEDVGV<br>YYCFQVSHVPYTFGGGTKVEIKR |

Example 4.2.2

Construction of Humanized Antibodies

The in silico designed humanized antibodies described in Example 4.2.1 were constructed de novo using oligonucleotides. For each variable region cDNA, 6 oligonucleotides of 60-80 nucleotides each were designed to overlap each other by 20 nucleotides at the 5' and/or 3' end of each oligonucleotide. In an annealing reaction, all 6 oligos were combined, boiled, and annealed in the presence of dNTPs. DNA polymerase I, Large (Klenow) fragment (New England Biolabs #M0210, Beverley, Mass.) was added to fill-in the approximately 40 bp gaps between the overlapping oligonucleotides. PCR was then performed to amplify the entire variable region gene using two outermost primers containing overhanging sequences complementary to the multiple cloning site in a modified pTT3 vectors. The PCR products derived from each cDNA assembly were separated on an agarose gel and the band corresponding to the predicted variable region cDNA size was excised and purified. The variable heavy region was inserted in-frame into a cDNA fragment encoding a wild-type human IgG1 constant region, or a human IgG1 constant region containing 2 hinge-region amino acid mutations by homologous recombination in bacteria. (Zhang, Y et al. Nature Biotechnol. 18(12):1314-7 (2000)). The mutations were a leucine to alanine change at position 234 (EU numbering) and a leucine to alanine change at position 235 (Lund et al. J. Immunol., 147:2657 (1991)). The variable light chain region was inserted in-frame into a human kappa constant region by homologous recombination. Bacterial colonies were isolated, plasmid DNA extracted, and cDNA inserts were sequenced in their entirety. pTT3 vectors containing correct humanized heavy and light chains corresponding to each antibody were co-transfected into HEK293 cells to transiently produce full-length humanized anti-PGE$_2$ antibodies. Cell supernatants containing recombinant chimeric antibody were purified by Protein A Sepharose chromatography and bound antibody was eluted by the addition of 0.1N acetic acid/0.15M NaCl (pH3.0). Antibodies were neutralized and dialyzed in PBS.

Example 4.2.3

Alternative Construction of Humanized Anti-PGE2 Antibodies

This example describes the humanization of an anti-PGE$_2$ antibody. Humanization of the murine monoclonal antibody 2B5-8.0 was carried out essentially according to the procedure of Queen, C., et al., Proc. Natl. Acad. Sci. USA 86: 10029-10033 (1989). First, human V segments with high homology to the 2B5-8.0 VH or VL amino acid sequences were identified. Next, the complementarity-determining region (CDR) sequences together with framework amino acids important for maintaining the structures of the CDRs were grafted into the selected human framework sequences. In addition, human framework amino acids that were found to be rare in the corresponding V region subgroup were substituted with consensus amino acids to reduce potential immunogenicity.

For humanization of the 2B5-8.0 variable regions, the general approach provided in the present invention was followed. First, a molecular model of the 2B5-8.0 variable regions was constructed with the aid of the computer programs ABMOD and ENCAD (Levitt, M., J. Mol. Biol. 168: 595-620 (1983)). Next, based on a homology search against human V and J segment sequences, the VH segment MUC 1-1'CL (Griffiths, A. D., et al., EMBO J. 12: 725-734 (1993)) and the J segment JH4 (Ravetch, J. V., et al., Cell 27: 583-591 (1981)) were selected to provide the frameworks for the Hu2B5-8.0 heavy chain variable region. For the Hu2B5-8.0 light chain variable region, the VL segment TR1.37'CL (Portolano, S., et al., J. Immunol. 151: 2839-2851 (1993)) and the J segment JK2 (Hieter, P. A., et al., J. Biol. Chem. 257: 1516-1522 (1982)) were used. The identity of the framework amino acids between 2B5-8.0 VH and the acceptor human MUC1-1'CL and JH4 segments was 76%, while the identity between 2B5-8.0 VL and the acceptor human TR1.37'CL and JK2 segments was 84%.

At framework positions in which the computer model suggested significant contact with the CDRs, the amino acids from the mouse V regions were substituted for the original human framework amino acids. For humanization of 2B5-8.0, the framework region amino acid substitution at a key residue is selected from the group consisting of M (human) to I (mouse) at position 48, R (human) to K (mouse) at position 67, V (human) to A (mouse) at position 68, I (human) to L (mouse) at position 70 and R (human) to V (mouse) at position 72 in the heavy chain variable region; and D (human) to V (mouse) at position 75 in the light chain variable region. In addition, a few amino acids have been changed to the consensus amino acids in the same human variable domain subgroups to eliminate potential immunogenicity, which includes A to T substitution at position 76 in the heavy chain variable region, and E to D substitution at position 1 and L to I substitution at position 2 in the light chain variable region.

The protein sequences of the CDR grafted variable domains (VH and VL of Hu2B5.P1) and the variable domains which incorporated all the back mutations and consensus substitutions (VH and VL of Hu2B5.P2) based on this humanization analysis are provided below. It is understood in general that any humanized version with one or a few such back mutations and consensus substitutions fall within the scope of this invention. Antibody E comprised VH Hu2B5.P2 and VL Hu2B5.P2; Antibody F comprised VH Hu2B5.P2 and VL Hu2B5.P1; Antibody G comprised VH Hu2B5.P1 and VL Hu2B5.P2; and Antibody I comprised VH Hu2B5.P1 and VL Hu2B5.P1.

TABLE 11

Humanized Anti-PGE$_2$ Antibodies With CDRs of 2B5-8.0

| SEQ ID No. | Protein region | Sequence 12345678901234567890123456789012345678 90 |
|---|---|---|
| 78 | VH Hu2B5.P1 | QVQLVQSGAEVKKPGASVKVSCKASGYTFTKYWLGWVRQA PGQGLEWMGDIYPGYDYTHYNEKFKDKVTITRDTSASTAY MELSSLRSEDTAVYYCARSDGSSTYWGQGTLVTVSS |
| | VL HU2B5.P1 | ELVMTQSPLSLPVTPGEPASISCTSSQNIVHSNGNTYLEW YLQKPGQSPQLLIYKVSNRFSGVPDRFSGSGSGTDFTLKI SRVEAEDVGVYYCFQVSHVPYTFGQGTKLEIK |
| 80 | VH HU2B5.P2 | QVQLVQSGAEVKKPGASVKVSCKASGYTFTKYWLGWVRQA PGQGLEWIGDIYPGYDYTHYNEKFKDKATLTVDTSTSTAY MELSSLRSEDTAVYYCARSDGSSTYWGQGTLVTVSS |
| 81 | VL HU2B5.P2 | DTVMTQSPLSLPVTPGEPASISCTSSQNIVHSNGNTYLEW YLQKPGQSPQLLIYKVSNRFSGVPDRFSGSGSGTVFTLKI SRVEAEDVGVYYCFQVSHVPYTFGQGTKLEIK |

Example 4.2.4

Characterization of Humanized Anti PGE$_2$ Antibodies

The ability of the purified humanized anti-PGE$_2$ antibodies to bind PGE$_2$ was determined by biotin-PGE$_2$ ELISA or 3H-PGE$_2$ radioimmunoassay as described in Example 1.1.A, Cross reactivity of the humanized anti-PGE$_2$ antibodies was determined by competitive biotin-PGE$_2$ ELISA or 3H-PGE$_2$ radioimmunoassay as described in Example 1.1.B. Inhibition of PGE$_2$ activity by the humanized anti-PGE$_2$ antibodies was determined using a EP4 bioassay as described in Examples 1.1.C.

Figure 6:
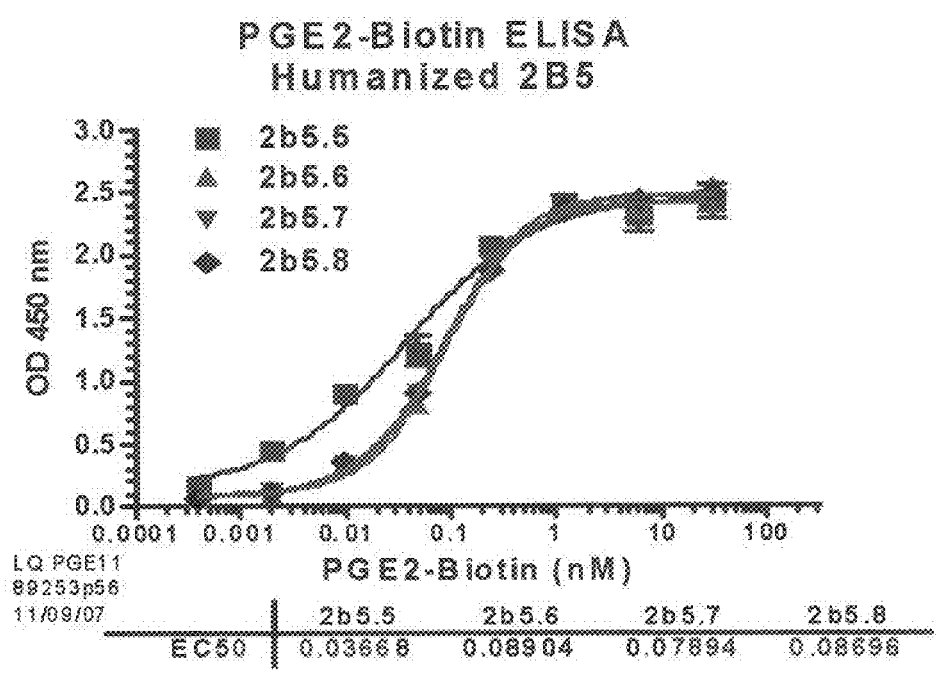
FIG. 6 provides humanized anti-PGE$_2$ mAb 2B5.5, 2B5.6, 2B5.7 and 2B5.8 to neutralize PGE$_2$ induced Ca$^{++}$ influx in EP4 transfected HEK293 Gα16 stable cell line measured by FLIPR as described in Example 1.1.C 1.
Figure 7:
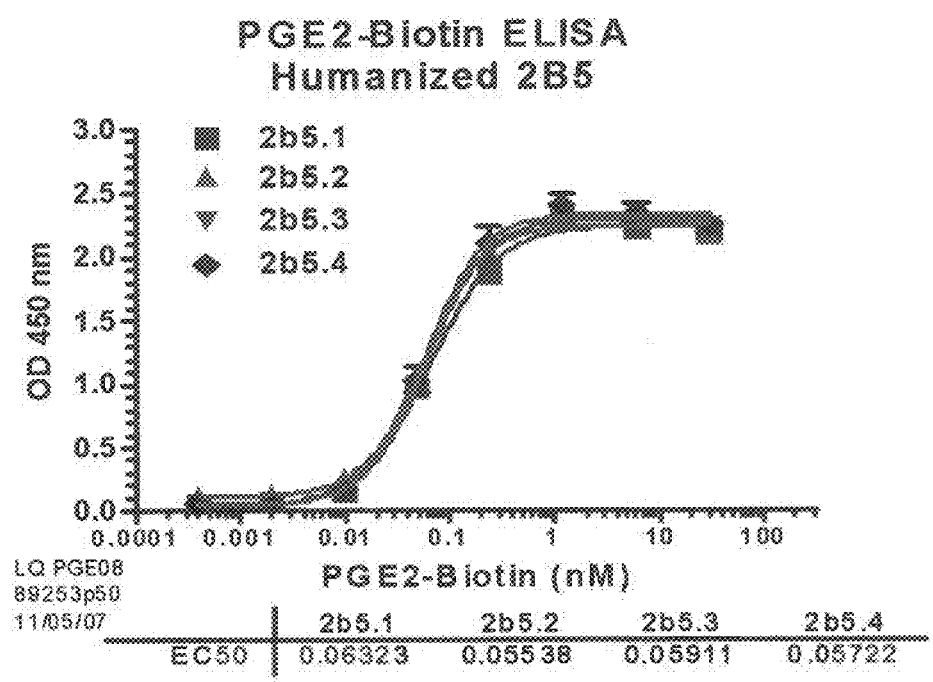
FIG. 7 provides humanized anti-PGE$_2$ mAb 2B5.1, 2B5.2, 2B5.3 and 2B5.4 to neutralize PGE$_2$ induced Ca$^{++}$ influx in EP4 transfected HEK293 Gα16 stable cell line measured by FLIPR as described in Example 1.1.C 1.
Figure 9:
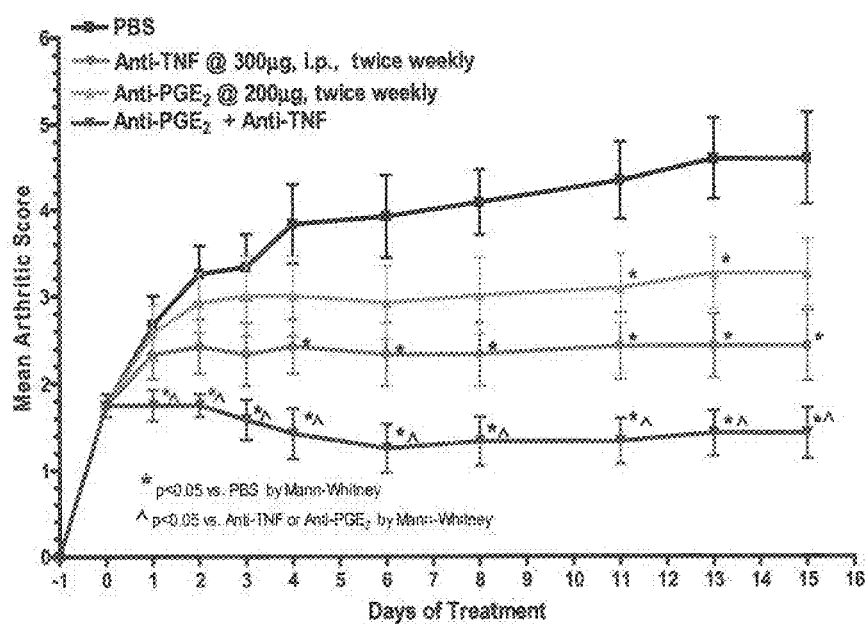
FIG. 9 provides efficacy of anti-PGE$_2$ antibody, anti-murine TNF antibody and their combination in a collagen-induced arthritis model measured by MAS (mean arthritis score).

All the humanized anti-PGE$_2$ antibodies were able to bind PGE$_2$ in a biotin-PGE$_2$ ELISA (FIGS. 6 and 7; Table 12). The humanized anti-PGE$_2$ antibodies were able to neutralize and block PGE$_2$ mediate calcium influx in an EP4 FLIPR assay. The alternative designed humanized anti-PGE$_2$ antibodies E, F, G and I were also able to bind to PGE$_2$ in a $^3$H-PGE$_2$ ELISA (Table 13). Hu2B5.7 was selected for further characterization of prostaglandin binding specificity in a $^3$H-PGE$_2$ competition ELISA and demonstrated specificity to PGE$_2$ (Table 13).

TABLE 12

Characterization of Humanized Antibodies

| Humanize Antibody | | Ch2B5.8.0 | Hu2B5.1 | Hu2B5.2 | Hu2B5.3 | Hu2B5.4 | Hu2B5.5 | Hu2B5.6 | Hu2B5.7 | Hu2B5.8 | Hu2B5.9 |
|---|---|---|---|---|---|---|---|---|---|---|---|
| EC50 (pM) ELISA | | 41-60 | 63 | 55 | 59 | 57 | 37 | 89 | 79 | 87 | NT |
| IC50 (pM) @ PGE$_2$ 25 pm Cellular Potency in EP4 assay | | 55 | 55 | 55 | 47 | 40 | 47 | 52 | 78 | 78 | 125 |
| Cross | PGE1 | 12 | 16 | 14 | 14 | 14 | 11 | 11 | 9.3 | 8.5 | NT |
| Reactivity | PGA2 | 0.17 | 0.21 | 0.18 | 0.18 | 0.22 | 0.18 | 0.15 | 0.15 | 0.20 | NT |
| Index (%) | PGD2 | <0.01 | <0.01 | <0.01 | <0.01 | <0.01 | <0.01 | <0.01 | <0.01 | <0.01 | NT |

TABLE 13

Characterization of Humanized Anti-PGE$_2$ Antibodies (continued)

| | Humanized Antibody ID | | | | |
|---|---|---|---|---|---|
| | A | E | F | G | I |
| VH/VL | Hu2B5.9 | VH Hu2B5.P2/ VL Hu2B5.P2 | VH Hu2B5.P2/ VL Hu2B5.P1 | VH Hu2B5.P1/ VL Hu2B5.P2 | VH Hu2B5.P2/ VL Hu2B5.P2 |
| PGE$_2$ binding in $^3$H-PGE$_2$ ELISA (IC$_{50}$, nM) | 0.704 | 0.416 | 0.955 | 0.574 | 1.299 |

TABLE 14

Characterization of Prostaglandin Selectivity for Humanized Anti-PGE$_2$ Antibodies Hu2B5.7

| | Anti-PGE$_2$ mAb | 2B5 | Hu2B5-7.0 |
|---|---|---|---|
| PG Selectivity in $^3$H-PGE$_2$ competition ELISA (CRI %) | PGE2 | 100 | 100 |
| | PGE1 | 12 | 5.6 |
| | PGA2 | 0.17 | 0.02 |
| | PGD2 | 0.04 | <1 × 10$^{-4}$ |
| | PGF2α | 0.25 | 0.06 |
| | PGI2 | NA | 0.12 |
| | Iloprost | NA | 0.006 |
| | Carbaprostacyclin | NA | 0.16 |
| | Pinane TXA2 | NA | 0.00016 |
| | 15R-Pinane TXA2 | NA | 0.0029 |
| | Carbocyclic TXA2 | NA | 0.00011 |
| | TXB2 | <0.01 | <0.01 |
| | 6-keto PGF1α | 0.4 | 0.47 |
| | PGB2 | 0.03 | 0.0004 |
| | 8-iso PGF2α | 0.02 | 0.06 |
| | 13,14-dihydroxyl-15-Keto PGE2 | <0.01 | 0.0092 |
| | 2,3-dinor-6-keto-PGF1α | NA | 0.19 |
| | 15-keto PGE2 | <0.01 | 0.011 |
| | 19R-hydroxy PGE2 | <0.01 | 0.07 |
| | LTE4 | <0.01 | 0.01 |
| | 5(S)-HETE | <0.01 | <0.01 |
| | Arachidonic acid | <0.01 | <0.01 |

Example 4.2.4.A

Humanized Anti PGE$_2$ Antibodies Block Binding of PGE$_2$ to PGE$_2$ Receptor

Competitive inhibition of PGE$_2$ binding to PGE$_2$ receptors, for example EP4, by an anti-PGE$_2$ antibody can be determined by a cell-based or membrane based receptor binding assay using $^3$H-PGE$_2$ as described in Example 1.1.D and a cell based FACS assay as described in Example 1.E.

For a therapeutic mAb with serum half-life between 10 and 20 days in man, the serum concentration is normally between 5-15 µg/ml, with a weekly or bi-weekly IV or SC 3 mpk or less dosing regiment. Based on this calculation, hu2B5.1-Hu2B5.9 are likely to completely (100%) block PGE$_2$ binding to EP4 in vivo as a therapeutic mAb, at a serum concentration of 100 nM (or 15 ug/ml), under a conventional dosing regimen of a monoclonal antibody.

Example 4.2.5

Biophysico-Chemical Characterization of Humanized Anti-PGE$_2$ Antibodies

Criteria tested ranged from general drug-like property parameters such as, parameters indicating intrinsic stability (differential scanning calorimetry or DSC), and general physical and chemical stability (e.g., purity including fragmentation and aggregation monitoring by SEC).

Analytical methods used for biophysico-chemical characterization:

Example 4.2.5.1

Size Exclusion Chromatography (SEC)

Size exclusion chromatography was used to separate proteins based on size. Proteins are carried in an aqueous mobile phase and through a porous stationary phase resin packed in a column. The retention time in the column is a function of the hydrodynamic size of the protein and the size of the pores in the packed resin bed. Smaller molecules can penetrate into smaller pores in the resin and are retained longer than larger molecules. Upon elution from the column the proteins are detected by UV absorbance. The SEC method used a TSK gel guard (TOSOH Biosciences, Montgomeryville, Pa., cat. no. 08543) and a TSK gel G3000SWxL (TOSOH Biosciences, Montgomeryville, Pa., cat. no. 08541). The mobile phase was 100 mM Na2HPO4, 200 mM Na2SO4, pH 7.0. The flow rate was 0.3 mL/minute. Injection volume was 20 µL of 1 mg/mL sample. The column temperature was room temperature. The autosampler temperature was 2-8° C. The total run time was 50 minutes. The detection was based on UV absorbance at 214 nm wavelength, with band width set at 8 nm, using reference wavelength at 360 nm with band width 100 nm.

Example 4.2.5.1

Differential Scanning Calorimetry (DSC)

The thermal stability of the anti-PGE$_2$ antibodies was assessed using a DSC instrument. The DSC instrument used was an automated VP-DSC equipment with Capillary Cell (Microcal, GE Healthcare Ltd./Microcal, Buckinghamshire, UK). Unfolding of molecules was studied applying a 1° C./minute scan rate over a 25° C.-95° C. temperature range for samples at 1 mg/mL. Additional measurement parameters applied were a fitting period of 16 seconds, a pre-scan wait time of 10 minutes, and measurements were performed in none-feedback mode. Per individual measurement, 420 µL of sample/blank were filled into the DSC measurement sample holder, with a plate fill scheme as provided below. The thermograms obtained were fitted to a non two state model to obtain the midpoint temperatures and enthalpies of the different transitions.

An additional requirement for successful biologics development candidate is that the protein remains its native state and conformation. A protein in aqueous solution is in equilibrium between the native (folded) conformation and its denatured (unfolded) conformation. The stability of the native state is based on the magnitude of the Gibbs free energy (DG) of the system and the thermodynamic relationship between enthalpy (DH) and entropy (DS) changes. A positive DG indicates the native state is more stable than the denatured state—the more positive the DG, the greater the stability. For a protein to unfold, stabilizing forces need to be broken. Conformational entropy overcomes stabilizing forces allowing the protein to unfold at temperatures where entropy becomes dominant. DSC measures DH of protein unfolding due to heat denaturation. As a general rule it can be stated that the higher the transition midpoint (the Tm), the more stable the protein at lower temperatures. During the same experiment DSC also measures the change in heat capacity (DCp) for protein denaturation. Heat capacity changes associated with protein unfolding are primarily due to changes in hydration of side chains that were buries in the native state, but become solvent exposed in the denatured state. DSC has been shown to be a valuable predictor of liquid formulation stability for proteins and other biological macromolecules (Remmele, R. L. Jr., Gombotz, W. R., BioPharm 13, 36-46, 2000, and; Remmele, R. L. Jr., Nightlinger, N. Srinivasen, S., Gombotz, W. R., Pharm. Res. 15, 200-208, 1998).

Example 4.2.6

Stability of Humanized Anti-PGE$_2$ Antibody Hu2B5.7 During Clone Selection Process Example 4.2.6.A Stability of Humanized Anti-PGE$_2$ Antibody Hu2B5.7 Using DSC and SEC The stability of a series of clones (i.e., anti-PGE$_2$ antibodies) of the parent anti-PGE$_2$ antibody was assessed by using intrinsic thermodynamic clone stability determination using DSC (0.79 mg/mL clone concentration, formulated at pH 6 in a 10 mM citrate, 10 mM phosphate buffer) and by accelerated stability screening (0.79 mg/mL clone concentration, formulated at pH 6 in a 10 mM citrate, 10 mM phosphate buffer, for 7 days at 50° C.) where clone stability was monitored with SEC (Table 15).

TABLE 15

Formation Of Aggregates And Fragments In Hu2B5 humanized antibody variants Hu2B5.1-Hu2B5.9 Clone Samples As Determined By SEC (Start Of Stability Study)

| Clone | Aggregate (%) | Monomer (%) | Fragment (%) |
|---|---|---|---|
| Hu2B5.1 | 1.8071 | 93.7885 | 4.4044 |
| Hu2B5.2 | 1.846 | 94.8516 | 3.3025 |
| Hu2B5.3 | 2.116 | 94.1987 | 3.6853 |
| Hu2B5.4 | 2.234 | 94.5513 | 3.2146 |
| Hu2B5.5 | 1.5906 | 95.1406 | 3.2688 |
| Hu2B5.6 | 1.8265 | 95.446 | 2.7275 |
| Hu2B5.7 | 1.9668 | 95.5818 | 2.4514 |
| Hu2B5.8 | 2.1126 | 94.5969 | 3.2904 |
| Hu2B5.9 | 1.8559 | 95.6031 | 2.541 |

TABLE 16

Formation Of Aggregates And Fragments In Hu2B5 humanized antibody variants Hu2B5.1-Hu2B5.9 Clone Samples As Determined By SEC (7 Days Storage At 50° C.)

| Clone | Aggregate (%) | Monomer (%) | Fragment (%) |
|---|---|---|---|
| Hu2B5.1 | 2.5611 | 91.0715 | 6.3675 |
| Hu2B5.2 | 2.1753 | 93.1491 | 4.6755 |
| Hu2B5.3 | 2.6042 | 92.3518 | 5.044 |
| Hu2B5.4 | 2.1689 | 91.2889 | 6.5423 |
| Hu2B5.5 | 1.901 | 93.7376 | 4.3614 |
| Hu2B5.6 | 2.1577 | 93.817 | 4.0253 |
| Hu2B5.7 | 2.205 | 93.905 | 3.89 |

TABLE 16-continued

Formation Of Aggregates And Fragments In Hu2B5 humanized antibody variants Hu2B5.1-Hu2B5.9 Clone Samples As Determined By SEC (7 Days Storage At 50° C.)

| Clone | Aggregate (%) | Monomer (%) | Fragment (%) |
|---|---|---|---|
| Hu2B5.8 | 2.5144 | 93.3016 | 4.184 |
| Hu2B5.9 | 1.9559 | 94.6313 | 3.4127 |

Tables 15 and 16 provide the results of SEC testing for up to 7 days storage of the humanized anti-PGE$_2$ antibodies, showing the levels of monomer at the start and at the end of the accelerated stability screening. Hu2B5.7 and Hu2B5.9 revealed the highest monomer levels after 7 days accelerated stability screening. The results shown in Table 17 demonstrated that hu2B5.7 also had a very favorable intrinsic stability profile (DSC data) compared to other clones of the panel (e.g., Hu2B5.4).

An IgG antibody typically shows three unfolding transitions (Tm): unfolding of the intact antibody is associated with the melting of the CH2 domain in the Fc fragment, melting of the CH3 domain in the Fc fragment, and melting of the Fab fragment. In order to select anti-PGE$_2$ antibodies with desirable drug-like properties, clones with high Tm values and high intrinsic stability such as Hu2B5.7 were selected (Table 17)

TABLE 17

Intrinsic Thermodynamic Clone Stability Determination Of Humanized Anti-PGE$_2$ Antibody Clones Via DSC (0.79 mg/mL Clone Antibody Concentration, Formulated At pH 6 in a 10 mM Citrate, 10 mM Phosphate Buffer)

| Clone | Tm1 (° C.) | Tm2 (° C.) | Tm3 (° C.) |
|---|---|---|---|
| Hu2B5.1 | 72.835 | 75.02 | 82.785 |
| Hu2B5.2 | 72.845 | 75.08 | 82.67 |
| Hu2B5.3 | 72.67 | 72.96 | 82.67 |
| Hu2B5.4 | 71.095 | 72.41 | 82.58 |
| Hu2B5.5 | 73.31 | 75.755 | 82.97 |
| Hu2B5.6 | 73.035 | 75.585 | 82.95 |
| Hu2B5.7 | 72.67 | 75.445 | 82.795 |
| Hu2B5.8 | 72.96 | 75.33 | 82.83 |
| Hu2B5.9 | 73.235 | 75.965 | 83.04 |

Example 4.2.6.B

Capillary Zone Electrophoresis of Hu2B5.1-Hu2B5.9

Capillary zone electrophoresis is a capillary electrophoresis method in which the capillary is filled with buffer and the separation mechanism is based on differences in electrophoretic mobility of the analyte through the buffer. The electrophoretic mobility of a molecule is related to the charge-to-size ratio. A Beckman-Coulter ProteomeLab PA 800 (Beckman Coulter, Fullerton, Calif.) was used for the CZE analysis. A neutral capillary (eCAP neutral, 56 cm total length, 50 µm I. D. Beckman-Coulter, P/N 477441, Fullerton, Calif.) was used. The method used a 30.2 cm capillary with a detection window 20.2 cm from the sample introduction inlet. The running buffer was 100 mM EACA (6-Aminocaproic acid, Sigma A7824-100 G, St. Louis, Mo.) with 0.1% MC (from 1% Methylcellulose solution, Convergent Bioscience, cat# 101876, Toronto, ON, Canada), pH 5.5.

The results showed that Hu2B5.1, Hu2B5.3, Hu2B5.5, Hu2B5.7, Hu2B5.9 migrated more basic (e.g., they had a shorter migration time) than Hu2B5.2, Hu2B5.4, Hu2B5.6, Hu2B5.8. This may be due to the fact that Hu2B5.1, Hu2B5.3, Hu2B5.5, Hu2B5.7, Hu2B5.9 all have R at heavy chain #84 amino acid, while the other four samples have S at the same position. All nine samples showed a main peak and minor acidic and basic species, but there was not much difference among the distribution of the different species.

Example 4.3

Crystallization of Hu2B5.7 Complexed to PGE2

The Fab portion of Hu2B5.7 is complexed with $PGE_2$ and crystals of the complex are generated as follows.

Example 4.3.1

Preparation and Purification of Hu2B5.7 Fab Fragment

To prepare Hu2B5.7 Fab fragment, Hu2B5.7 IgG in 0.15 M PBS buffer is first concentrated to 2 mg/ml using an Ultrafree-15 Biomax 10 kDa molecular weight cut-off (MWCO) centrifugal filter device (Millipore). A papain gel slurry (Pierce) is pre-washed and charged in 2-3× with Buffer A (20 mM $Na_2HPO_4$, 10 mM EDTA, 20 mM cysteine) at a 1:1 volume ratio. The concentrated antibody is then mixed with 50% papain gel slurry and incubated at 37° C. for 24 hours with vigorous shaking. The antibody/slurry mixture is centrifuged (Beckman 6KR) and the supernatant is loaded onto a PBS pre-equilibrated Superdex 75. A major peak is eluted and protein is pooled. A 25 mL Protein A Sepharose 4 Fast Flow affinity column (Amersham Pharmacia) is prepared by washing with 100 mL of PBS. The pooled antibody fragments are applied to the affinity column (2 mL/min flow rate). Fractions containing Hu2B5.7 Fab fragments (monitored by UV absorbance at 280 nm) are collected in the flow-thru. Fractions containing a Hu2B5.7 Fab fragment concentration greater than 0.3 mg/mL (determined by UV absorbance at 280 nm) are pooled and frozen at −80° C. Sample purity is assessed with SDS-PAGE.

Example 4.3.2

PGE2/Hu2B5.7 Fab Complex Preparation

PGE2 and Hu2b5.7 Fab protein are mixed at a 1:1 molar ratio and incubated for 1 hour at 4° C. The complex sample is loaded onto a pre-equilibrated (20 mM Tris pH 7.5, 150 mM NaCl) Superdex 200 column at 0.5 ml/minute. The complex is pooled and concentrated to 24 mg/mL using an Ultrafree-15 Biomax 10 kDa molecular weight cut-off (MWCO) centrifugal filter device (Millipore) and frozen at −80° C. Sample purity is assessed with SDS-PAGE.

Example 4.3.3

Crystallization of PGE2/Hu2B5.7 Fab Complex

Frozen PGE2/Hu2B5.7 complex stock (~24 mg/mL) is thawed on ice. The complex (1.0 µL) is mixed with 1.0 µL of reservoir solution (1.75 M Ammonium Sulfate, 100 mM MES pH 6.5, 10 mM CaCl2). The resulting drop is mixed in a sitting drop well (CrysChem sitting-drop plate) over the reservoir at about 18° C. Diamond-like crystals generally appeared within one week.

Example 4.3.4

Cryoprotection and Flash Cooling of PGE2/Hu2B5.7 Fab Complex Crystals

Crystals of PGE2/Hu2B5.7 Fab complex are harvested using a fiber loop in mother liquor+20% glycerol. The crystals are subsequently flash-cooled by plunging into liquid nitrogen.

Example 4.3.5

X-ray Diffraction Data Collection of PGE2/Hu2B5.7 Fab Complex

X-ray diffraction data from PGE2/Hu2B5.7 Fab crystals are collected at the IMCA beamline at the Advanced Photon Source in Argonne, Ill. The crystals are maintained at a temperature of 100 K with an Oxford Cryosystems Cryostream cooler during data collection. A total of 180 frames are collected at an oscillation range of 1.0°. The data are processed with the HKL2000 suite of programs (Otwinowski and Minor, 1997). After determining the crystal orientation, the data are integrated with DENZO and scaled and merged with SCALEPACK, and placed on an absolute scale and reduced to structure factor amplitudes with TRUNCATE (French and Wilson, 1978). Five percent of the unique reflections are assigned, in a random fashion, to the "free" set, for calculation of the free R-factor (Rfree) (Brünger, 1992); the remaining 95% of the reflections constitute the "working" set, for calculation of the R-factor (R).

Example 4.3.6

Molecular Replacement Solution and Refinement of PGE2/Hu2B5.7 Fab Complex Crystal Structure A maximum likelihood molecular replacement solution is determined using the program PHASER (Read, 2001). A total of six PGE2/Hu2B5.7 monomers are solved at 3.0 Å resolution an appropriate space group. The search model is the crystal structure of Fab reported previously (Protein Data Bank entry 1BJ1; Muller et al. 1998). Coordinates are generated based on the molecular replacement solution.

The refinement of the PGE2/Hu2B5.7 Fab complex crystal structure begins with the molecular replacement solution coordinates, described above, in an appropriate space group. Refinement begins using rigid-body refinement by the program REFMAC available in the CCP4 suite of programs (Murshudov et al., 1997, Collaborative Computational Project, 1994). De novo PGE2 electron density is observed. Manual building of six PGE2 monomers is guided by the public PGE2 NMR structure 1IJZ (Moy et al., 2001) using the molecular graphics program O (Jones et al., 1991) and examination of 2Fo-Fc and Fo-Fc electron-density maps. The refinement program REFMAC (Murshudov et al., 1997) is used for iterative rounds of restrained refinement resulting in the following statistics: R of 25.8% (Rfree 30.5%).

Example 5.0

Pharmacokinetic Analyses

Example 5.1

Pharmacokinetic Analysis of Recombinant Mouse Anti-$PGE_2$ Antibodies

Pharmacokinetic studies with mouse mAb 2B5.8.0 were carried out in Sprague Dawley rats and Balb/C mice. Male and female rats and mice were dosed intravenously or intraperitoneally (mice only) with a single dose of 4 mg/kg 2B5.8.0 and serum samples were analyzed using antigen capture based chemiluminescent MSD (Meso Scale Discovery) method (Meso Scale Discovery, Gaithersburg, Md.). Pharmacokinetic parameters were calculated by non-compartmental analysis using WinNonlin.

Example 5.1.1

Assay Used to Quantitate 2B5.8.0 in PK Serum Samples

The following MSD assay was used to measure antibody concentration in rat and mouse serum. MSD streptavidin plates (Meso Scale Discovery, Gaithersburg, Md.) were washed with phosphate buffered saline containing 0.05% Tween-20 (Sigma, St. Louis, Mo.). Plates were blocked with 250 μL/well blocking solution (MSD Block, Meso Scale Discovery, diluted to 3% final concentration in PBS) for 1 hour, covered, with shaking (600 rpm) at room temperature. After washing, 70 μL of biotinylated PGE2 (Prostoglandin E2-biotinamide, Cayman Chemical, Ann Arbor, Mich., cat# 10006987, lot# 190831-191028, 0.01 ug/mL in assay buffer) was added to each well. The plates were covered and incubated with shaking (600 rpm) for 1 hour at room temperature Prior to analysis, rat and mouse serum samples were thawed on ice, mixed gently, and centrifuged at 14,000 rpm for 3 minutes at 4° C. in an eppendorf centrifuge. Standard curve and control samples were prepared in rat and mouse serum. A Tecan Evo automated liquid handling station was used to dilute standard curve, high, medium, and low controls, and serum samples in assay buffer, keeping 1% final serum concentration constant. MSD plates were washed again and study samples, standard curve samples and blanks, as well as high, medium, and low controls were added (70 μL/well). The plates were covered, and incubated for 1 hour with shaking (600 rpm) at room temperature.

After incubation, the MSD plates were washed, and 70 μL of sulfo-tagged goat anti-mouse IgG (Meso Scale Discovery; diluted to 1 ug/mL in assay buffer) was added to each well. The MSD plates were covered, and incubated with shaking (600 rpm) for 1 hour at room temperature, then the plates were washed and developed with 2× Read Buffer (Meso Scale Discovery). Chemilumeniscence was measured within ten minutes on the MSD Sector Imager 6000.

Standard curves were analyzed using four-parameter logistic fit and sample concentrations were calculated by XLfit4 software version 2.2.1 Build 16, (Microsoft Corporation, Redmond, Wash.). Pharmacokinetic parameters were calculated for each animal using Winonlin software version 5.0.1 (Pharsight Corporation, Mountain View, Calif.) by noncompartmental analysis.

Example 5.1.2

Pharmacokinetic Studies of 2B5.8.0 Carried Out in SD Rats and Balb/C Mice

Surgically altered jugular vein cannulated, JVC) and regular male and female Sprague-Dawley Rats (approximately seven weeks old, weighing 240-390 grams) were purchased from Charles River Laboratories (Wilmington, Mass.). The animals were housed in rooms maintained at constant temperature and humidity under 12 hours light/dark cycle, fed with normal rodent chow and were allowed food and water ad libitum. Hydration and clinical conditions of the animals were monitored daily.

Male and female Balb/c mice (weighing approximately 0.025 kg) were purchased from Charles River Laboratories (Wilmington, Mass.). The animals were allowed food and water ad libitum. Blood samples were collected (0.2 mL from the rats via the tail vein and by cardiac puncture from the mice) at various timepoints (5 mice at each timepoint) allowed to clot for 30 minutes at room temperature, centrifuged for 3 minutes at 13,200 rpm, the serum transferred to eppendorf tubes and stored frozen at −80° C.

Following intravenous administration in rat, 2B5.8.0 exhibited bi-exponential decay, typical of antibodies. 2B5.8.0 clearance and volumes of distributions were low (Table 18), and half-life was long, T1/2: 9.1 and 8.9 days (male and female respectively). Large inter-animal variability was seen among female rats, however not in males.

Following IV administration in Balb/C mice, 2B5.8.0 showed very long half-lives (26.3 and 16.2 days, male and female respectively) with low clearance and volumes of distributions (Table 18). Following intraperitoneal administration in mice, at the early timepoints large inter animal variability was observed in the females. Absorption was slow, with high Cmax of 37-49 ug/ml reached by 1-2 days. The half-life was long (13.8-16.1 days) and the bioavailability was good (65.8-72.0%).

TABLE 18

Main Pharmacokinetic Parameters Of 2B5.8.0 In Sprague-Dawley Rats And Balb/C Mice

| Species/dose | | T½ (day) | CL (mL/hr/kg) | Vz (mL/kg) | Vss (mL/kg) | $AUC_{0-\infty}$ (mg · hr/mL) | MRT (day) |
|---|---|---|---|---|---|---|---|
| IV | | | | | | | |
| Rat (4 mg/kg) | M (N = 5) | 9.1 ± 1.3 | 0.41 ± 0.03 | 127 ± 18.9 | 122 ± 18.5 | 9.9 ± 0.7 | 12.6 ± 1.6 |
| | F (N = 3) | 8.5 ± 2.2 | 0.37 ± 0.13 | 101 ± 13.1 | 88 ± 6.2 | 12.0 ± 4.6 | 10.8 ± 3.5 |
| Mouse (4 mg/kg) | M | 26.3 | 0.15 | 135 | 134 | 26.9 | 37.5 |
| | F | 16.2 | 0.16 | 92 | 89 | 24.5 | 22.8 |

| Species/dose | | $C_{max}$ (μg/mL) | Tmax (day) | T½ (day) | MRT (day) | $AUC_{0-\infty}$ (mg · hr/mL) | F (%) |
|---|---|---|---|---|---|---|---|
| IP | | | | | | | |
| Mouse (4 mg/kg) | M | 37.3 | 2 | 16.1 | 23.4 | 19.4 | 72 |
| | F | 49.4 | 1 | 13.8 | 19.3 | 16.1 | 65.8 |

Example 5.1.3

Pharmacokinetic Analysis of Recombinant Humanized Anti-PGE$_2$ hu2B5.7 and hu2B5.4

Pharmacokinetic studies with hu2B5.7 and hu2B5.4 were carried out in Sprague Dawley rats. Male rats were dosed intravenously with a single dose of 4 mg/kg of hu2B5.7 and hu2B5.4 and serum samples were analyzed using antigen capture based chemiluminescent MSD (Meso Scale Discovery) method. Pharmacokinetic parameters were calculated by non-compartmental analysis using WinNonlin.

Example 5.1.3.1

Assay Used to Quantitate Hu2b5.7 in PK Serum Samples

The following MSD assay was used to measure hu2B5.7 and hu2B5.4 concentrations in rat serum.

MSD streptavidin plates (Meso Scale Discovery) were washed with phosphate buffered saline containing 0.05% Tween-20 (diluted from 10×PBS, Abbott Bioresearch Center, Media Room, Worcester, Mass. and Tween-20, Sigma, St. Louis, Mo.). Plates were blocked with 250 µL/well blocking solution (MSD Block, Meso Scale Discovery, diluted to 3% final concentration in PBS) for 1 hour, covered, with shaking (600 rpm) at room temperature. After washing, 70 µL of biotinylated PGE2 (Prostoglandin E2-biotinamide, Cayman Chemical, Ann Arbor, Mich., cat# 10006987, lot# 190831-191028; 0.01 ug/mL in assay buffer) was added to each well. The plates were covered and incubated with shaking (600 rpm) for 1 hour at room temperature.

Prior to analysis, rat serum samples were thawed on ice, mixed gently, and centrifuged at 14,000 rpm for 3 minutes at 4° C. in an eppendorf centrifuge. Standard curve and control samples were prepared in rat serum. Tecan Evo automated liquid handling station was used to dilute standard curve, high, medium, and low controls, and serum samples in assay buffer, keeping 1% final serum concentration constant. MSD plates were washed again and study samples, standard curve samples and blanks, as well as high, medium, and low controls were added (70 µL/well). The plates were covered, and incubated for 1 hour with shaking (600 rpm) at room temperature.

After incubation, the MSD plates were washed, and 70 µL sulfo-tagged goat anti-human IgG (Meso Scale Discovery; diluted to 1 ug/mL in assay buffer) was added to each well. The MSD plates were covered, and incubated with shaking (600 rpm) for 1 hour at room temperature, then the plates were washed and developed with 2× Read Buffer (Meso Scale Discovery). Chemilumeniscence was measured within ten minutes on the MSD Sector Imager 6000.

Standard curves were analyzed using four-parameter logistic fit and sample concentrations were calculated by XLfit4 software version 2.2.1 Build 16, (Microsoft Corporation, Redmond, Wash.). Pharmacokinetic parameters were calculated for each animal using Winonlin software version 5.0.1 (Pharsight Corporation, Mountain View, Calif.) by noncompartmental analysis.

Example 5.1.3.2

Pharmacokinetic Studies Carried Out in Sprague-Dawley Rats

Surgically altered jugular vein cannulated, JVC) male Sprague-Dawley Rats (approximately seven weeks old, weighing 240-390 grams) were purchased from Charles River Laboratories (Wilmington, Mass.). The animals were housed in rooms maintained at constant temperature and humidity under a 12 hour light/dark cycle, fed with normal rodent chow and were allowed food and water ad libitum. Hydration and clinical conditions of the animals were monitored daily.

0.2 mL blood samples were collected from the rats at various timepoints, allowed to clot for 30 minutes at room temperature, centrifuged for 3 minutes at 13,200 rpm, the serum transferred to eppendorf tubes and stored frozen at −80° C.

Following intravenous administration, hu2B5.7 and hu2B5.4 serum concentrations declined bi-exponentially, typical of antibodies. Hu2B5.7 and hu2B5.4 clearances and volumes of distributions were low and half-lives were long; T1/2: 12.4 days for both antibodies (Table 19). After about 10-14 days, several animals exhibited unexpected drops in serum hu2B5.7 concentrations. These sudden drops may have been due to the development of anti-drug antibodies (ADA); however, this was not confirmed. Animals with possible ADA responses were omitted from the final pharmacokinetic calculations.

TABLE 19

Main Pharmacokinetic Parameters of hu2B5.7 and hu2B5.4 in Male Sprague-Dawley Rats After an Intravenous Dose of 4 mg/kg IV

| Ab/dose | | T½ (day) | CL (mL/hr/kg) | Vz (mL/kg) | Vss (mL/kg) | AUC$_{0-\infty}$ (mg·hr/mL) | MRT (day) |
|---|---|---|---|---|---|---|---|
| hu2B5.7/ 4 mg/kg | (N = 3) | 12.4 ± 0.6 | 0.41 ± 0.07 | 176 ± 30.8 | 165 ± 19.8 | 9.9 ± 1.8 | 16.8 ± 1.0 |
| hu2B5.4/ 4 mg/kg | (N = 4) | 12.4 ± 5.1 | 0.35 ± 0.07 | 143 ± 40.2 | 145 ± 31.8 | 11.8 ± 2.0 | 18.0 ± 6.0 |

Example 4.4

In Vivo Efficacy of Recombinant Mouse and Humanized PGE2 Antibodies

The in vivo efficacy of anti-PGE2 antibodies is assessed as follows.

Example 4.4.1

In Vivo Efficacy of Mouse and Humanized Anti-PGE2 Antibodies in a Carrageenan-Induced Footpad Edema Model Carrageenan-Induced Footpad Edema is an acute rodent model of innate immune function. The in vivo efficacy of mouse anti-PGE2 antibody 2B5-8.0 is assessed in a carragenan-induced paw edema model. The induction of paw inflammation with carrageenan is performed similarly as previously described (Joseph P. Portanova, et al. J. Exp. Med. 184: 883-891 (1996)). Intradermal (ID) injection of an inflammatory agent causes a rapid influx of neutrophils and fluid edema which peaks at approximately 4 hours, followed by an influx of macrophages and monocytes which peaks at approximately 48 hours. C57.BL/6 mice (8-10-week-old, Jackson Laboratories, Bar Harbor, Me.) were injected ID in the rear footpad with 30 μL of either PBS (left) or λ-carrageenen (Sigma Aldrich, St. Louis, Mo.) in PBS (right) at a concentration of 5.0 mg/mL (150 μg/mouse). Rear footpad thickness was measured by Dyer spring caliper model #310-119 at baseline (time=0), and 4 hours post carrageenan challenge. Significant difference for paw thickness was determined by comparing mean paw swelling for each treatment group to vehicle in a Student's two-tailed t-test. Mice were given a dose titration of an anti-PGE$_2$ antibody (2B5-8.0) intraperitonially (IP) 18 hours prior to carrageenan challenge, or Indomethacin, PO 2 hours prior to challenge. The endpoint measured was the difference in paw swelling (edema) between right and left paws 4 hours after treatment. The anti-PGE$_2$ antibody inhibited paw edema dose-dependently, and provided a maximal 40-50% inhibition of paw swelling at 10 mg/kg, comparable to the maximal inhibition achieved by indomethacin (Table 20).

TABLE 20

Paw Swelling In Mouse Carrageenan-Indcued Footpad Edema After Ab Treatment

|  | Vehicle (PBS) | Anti-PGE2 (10 mg/kg, i.p.) | Indomethacin (3 mg/kg, p.o.) |
| --- | --- | --- | --- |
| Δ Paw Swelling (mm) | 0.857 ± 0.06 | 0.529 ± 0.04 | 0.486 ± 0.03 |
| % Inhibition | NA | 38 ± 4.6 | 57 ± 3.5 |

Example 4.4.2

In Vivo Efficacy of Mouse and Humanized Anti-PGE$_2$ Antibodies in a Carrageenan-Induced Hyperalgesia Model The in vivo efficacy of mouse anti-PGE2 antibody 2B5-8.0 and humanized anti-PGE2 antibody Hu2B5.7 is assessed by determining carragenan-induced hyperalgesia. The induction of paw inflammation with carrageenan is performed as previously described (Joseph P. Portanova, et al. J. Exp. Med. 184: 883-891 (1996)). Hyperalgesia is induced by the injection of 0.1 ml of a 0.1% carrageenan solution in sterile saline (FMC Corp., Rockland, Me.) into the hind footpad of a 200-g male Sprague Dawley rat (Charles River Laboratories, Portage, Me.). A hyperalgesic response to thermal stimulation is determined in the same animals by the method of Hargreaves et al. Pain. 32:77-88 (1988)). Hind paws are exposed to radiant heat emitted from a high intensity projection bulb at selected times after injection. The amount of time in which each hind paw remains in contact with the heat source is measured to the nearest 0.1 s. The hyperalgesic response is expressed as the difference in the latency withdrawal period between carrageenan- and saline-injected paws of each animal. In certain experiments, rats are administered indomethacin by oral gavage in 0.5% Methocel/0.025% Tween 80 (Sigma Chemical Co., St. Louis, Mo.) 1 hour before carrageenan administration. Other rats are injected intraperitoneally with mouse anti-PGE2 mAb, 2B5-8.0, or humanized anti-PGE2 antibody, Hu2B5.7, or isotype-matched antibody 18 hours before carrageenan injection.

Example 4.4.2

In Vivo Efficacy of Mouse Anti-PGE$_2$ Antibodies in Collagen-Induced Arthritis

Type II bovine collagen (lyophilized) was obtained from the University of Utah (Salt Lake City, Utah). Male DBA/J mice (8-10-week-old, Jackson Laboratories, Bar Harbor, Me.) were immunized intradermally at the base of the tail with 100 μL of emulsion containing 100 μg of type II bovine collagen dissolved in 0.1 N of acetic acid and 100 μg of heat-inactivated *Mycobacterium tuberculosis* H37Ra (Complete Freund's Adjuvant, Difco, Laurence, Kans.). Twenty-one days after immunization with collagen, mice were boosted IP with 1 mg of Zymosan A (Sigma, St. Louis, Mo.). Following the boost, mice were monitored daily for arthritis. Each paw was scored by the following criteria: 0=normal; 1=swelling in one site, foot, or ankle; 2=swelling in foot and ankle; and 3=ankylosis. Scores were summed for each animal, and total average of all animals in each group was expressed as MAS. In addition to clinical scores, mice were also evaluated for paw-edema using Dyer spring calipers model #310-119. Mice were enrolled for the study between days 24 and 28 at the first clinical signs of disease. At the termination of the experiment, six paws from each group were harvested and stored in 10% neutral buffered formalin for micro CT and histology.

Micro-computed tomography was performed on a Scanco μCT-40 unit (Scanco Medical AG) at 60 kVp at 160 μA. The hind paws (stored in 70% ethanol) were secured in imaging tubes and the tarsal bone volume was measured for a 1.8-mm section of the mouse ankle from the base of the tibia to the tarsal/metatarsal joint at a resolution of 18 μm. The raw micro-computed tomography image was then analyzed using the Scanco AG μCT Evaluation program.

For histopathology analysis, formalin-fixed paws were sectioned and stained with Gills 3 hematoxylin (Richard-Allan Scientific, Kalamazoo, Mich.) and eosin with phloxine (Newcomer Supply, Middleton, Mich.). Severity of disease was evaluated histologically using the following criteria: 0=normal; 1=minimal change; 2=mild change; 3=moderate change; and 4=severe change. Scores were summed for each animal, and the total was expressed as an average of all animals in each group.

The therapeutic effects of anti-PGE2 alone was evaluated in mouse (male DBA/1J) collagen-induced arthritis, a standard preclinical model for human rheumatoid arthritis. Drug treatment was initiated after the mice developed signs of arthritic disease after immunization with bovine type II collagen. Mice were scored visually for clinical signs of arthritis and the results were recorded as the mean arthritic score (MAS). Paw swelling and MAS monitored over time, were also represented as area under the curve (AUC) (Table 21). After disease onset, treatment with anti-PGE2 mAb 2B5 reduced the AUC for MAS by 22%.

TABLE 21

Disease Score, Swelling And Bone Volume In Mouse CIA After Anti-PGE$_2$ 2B5-8.0 Treatment

| | Vehicle (PBS) | Anti-PGE2 (8 mg/kg, 2x/week, i.p.) |
|---|---|---|
| MAS (AUC) (Score # days) | 74 ± 7.3 | 57.4 ± 6.7 |
| Paw Swelling (AUC) (mm # days) | 14.3 ± 1.6 | 8.4 ± 1.3 |
| Bone Volume (mm$^3$) | 1.2 ± 0.2 | 1.6 ± 0.1 |

Example 4.4.2

In Vivo Efficacy of Mouse Anti-PGE2 Antibodies in Adjuvant-Induced Arthritis The in vivo efficacy of mouse anti-PGE2 antibody 2B5-8.0 is assessed in an adjuvant-induced arthritis model. Arthritis is induced in male Lewis rats (Harlan, Indianapolis, Ind.) by footpad injection of *Mycobacterium butyricum* in mineral oil (Difco Laboratories, Detroit, Mich.) as described previously. Dexamethasone and indomethacin (Sigma Chemical Co.) are suspended in Methocel/Tween and administered twice daily by gavage at dosages of 0.1 and 2 mg/kg, respectively. 2B5-8.0 and isotype control are administered daily at a dose of 10 mg/kg by intraperitoneal injection. Treatments are initiated on day 15 post adjuvant injection and continued until final assessment of paw volume of uninjected contralateral paws on day 21. Mice are carefully examined twice weekly for the visual appearance of arthritis in peripheral joints, and scores for disease activity are determined.

INCORPORATION BY REFERENCE

The contents of all cited references (including literature references, patents, patent applications, and websites) that maybe cited throughout this application are hereby expressly incorporated by reference in their entirety, as are the references cited therein. The practice of the present invention will employ, unless otherwise indicated, conventional techniques of immunology, molecular biology and cell biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

We claim:

1. A humanized antibody or antigen binding fragment thereof wherein the antibody or antigen binding fragment is capable of binding prostaglandin E$_2$, and the antibody or antigen binding fragment comprises a variable heavy (VH) and a variable light (VL) domain sequence selected from the group consisting of:
   a) SEQ ID NOs: 60 and 61;
   b) SEQ ID NOs: 62 and 63;
   c) SEQ ID NOs: 64 and 65;
   d) SEQ ID NOs: 66 and 67;
   e) SEQ ID NOs: 68 and 69;
   f) SEQ ID NOs: 70 and 71;
   g) SEQ ID NOs: 72 and 73;
   h) SEQ ID NOs: 74 and 75;
   i) SEQ ID NOs: 76 and 77;
   j) SEQ ID NOs: 78 and 79;
   k) SEQ ID NOs: 78 and 81;
   l) SEQ ID NOs: 80 and 79; and
   m) SEQ ID NOs: 80 and 81.

2. A humanized antibody or antigen binding fragment thereof, wherein the antibody or antigen binding fragment is capable of binding prostaglandin E$_2$, and the antibody or antigen binding fragment comprises complementarity determining region (CDR) sequences: GYTFTKYWLG (SEQ ID NO: 54), DIYPGYDYTHYNEKFKD (SEQ ID NO: 55), SDGSSTY (SEQ ID NO: 56), TSSQNIVHSNGNTYLE (SEQ ID NO: 57), KVSNRFSG (SEQ ID NO: 58), and FQVSHVPYT (SEQ ID NO: 59) and human framework sequences SEQ ID NOs: 72 and 73 modified by at least one framework region amino acid substitution in the heavy chain variable region selected from a substitution:
   a) at position 48, from the human residue methionine to murine residue isoleucine;
   b) at position 68, from the human residue valine to murine residue alanine; and
   c) at position 72, from the human residue threonine to murine residue valine.

3. A humanized antibody or antigen binding fragment thereof, wherein the antibody or antigen binding fragment is capable of binding prostaglandin E$_2$, and the antibody or antigen binding fragment comprises complementarity determining region (CDR) sequences: GYTFTKYWLG (SEQ ID NO: 54), DIYPGYDYTHYNEKFKD (SEQ ID NO: 55), SDGSSTY (SEQ ID NO: 56), TSSQNIVHSNGNTYLE (SEQ ID NO: 57), KVSNRFSG (SEQ ID NO: 58), and FQVSHVPYT (SEQ ID NO: 59) and human framework sequences SEQ ID NOs: 72 and 73 modified by one framework amino acid substitution at a residue adjacent to a CDR, a glycosylation site residue, a residue capable of interacting with prostaglandin E$_2$, a residue capable of interacting with a CDR, a residue within a Vernier zone, or a residue in a region that overlaps between a Chothia-defined variable heavy chain CDR1 and a Kabat-defined first heavy chain framework.

4. The antibody or antigen binding fragment of any one of claims 1, 2, and 3, further comprising a linker polypeptide or an immunoglobulin constant domain.

5. The antibody or antigen binding fragment of any one of claims 1, 2, and 3, wherein the antibody or antigen binding fragment is an immunoglobulin molecule, a disulfide linked Fv, a monoclonal antibody, a scFv, a single domain antibody, a diabody, a multispecific antibody, a Fab, a dual specific antibody, a Fab', a bispecific antibody, a F(ab')2, and/or a Fv.

6. The antibody or antigen binding fragment of claim 4, wherein the antibody or antigen binding fragment is an immunoglobulin molecule, a disulfide linked Fv, a monoclonal antibody, a scFv, a single domain antibody, a diabody, a humanized antibody, a multispecific antibody, a Fab, a dual specific antibody, a Fab', a bispecific antibody, a F(ab')2, and/or a Fv.

7. The antibody or antigen binding fragment of claim 4, wherein the antibody or antigen binding fragment comprises a human IgM heavy chain constant domain, a human IgG4 heavy chain constant domain, a human IgG1 heavy chain constant domain, a human IgE heavy chain constant domain, a human IgG2 heavy chain constant domain, a human IgG3 heavy chain constant domain, and/or a human IgA heavy chain constant domain.

8. The antibody or antigen binding fragment of claim 4, wherein the antibody or antigen binding fragment comprises an immunoglobulin constant domain comprising SEQ ID No: 1, SEQ ID No: 2, SEQ ID No: 3, or SEQ ID No: 4.

9. The antibody or antigen binding fragment of claim 4, wherein said antibody or antigen binding fragment is a crystallized antibody or antigen binding fragment.

10. The antibody or antigen binding fragment of claim 9, wherein said crystallized antibody or antigen binding fragment is a carrier-free pharmaceutical controlled release crystallized antibody or antigen binding fragment, 11. The antibody or antigen binding fragment of claim 9, wherein said antibody or antigen binding fragment has a greater half-life in vivo than the soluble counterpart of said antibody or antigen binding fragment.

12. An antibody conjugate comprising the antibody or antigen binding fragment of claim 4, the antibody conjugate further comprising an immunoadhesion molecule, an imaging agent, a therapeutic agent, or a cytotoxic agent.

13. The antibody conjugate of claim 12, wherein the imaging agent is a radiolabel, an enzyme, a fluorescent label, a luminescent label, a bioluminescent label, a magnetic label, or biotin.

14. The antibody conjugate of claim 13, wherein the radiolabel is $^{3}$H, $^{14}$C, $^{35}$S, $^{90}$Y, $^{99}$Tc, $^{111}$In, $^{125}$I, $^{177}$Lu, $^{166}$Ho, or $^{153}$Sm.

15. The antibody conjugate of claim 12, wherein the therapeutic or cytotoxic agent is an anti-metabolite, an alkylating agent, an antibiotic, a growth factor, a cytokine, an anti-angiogenic agent, an anti-mitotic agent, an anthracycline, a toxin, or an apoptotic agent.

16. A composition for the release of an antibody or antigen binding fragment, the composition comprising:
(a) a formulation, wherein the formulation comprises a crystallized antibody or antigen binding fragment, according to claim 9;
(b) an ingredient; and
(c) at least one polymeric carrier.

17. The composition of claim 16, wherein the polymeric carrier is a poly (acrylic acid), a poly (cyanoacrylate), a poly (amino acid), a poly (anhydride), a poly (depsipeptide), a poly (ester), a poly (lactic acid), a poly (lactic-co-glycolic acid) or PLGA, a poly (b-hydroxybutryate), poly (caprolactone), a poly (dioxanone); a poly (ethylene glycol), a poly ((hydroxypropyl) methacrylamide), a poly (organo) phosphazene), a poly (ortho ester), a poly (vinyl alcohol), a poly (vinylpyrrolidone), a maleic anhydride-alkyl vinyl ether copolymer, a pluronic polyol, albumin, alginate, cellulose, a cellulose derivative, collagen, fibrin, gelatin, hyaluronic acid, an oligosaccharide, a glycaminoglycan, a sulfated polysaccharide, or a blend and/or a copolymer thereof.

18. The composition of claim 16, wherein the ingredient is albumin, sucrose, trehalose, lactitol, gelatin, hydroxypropyl-β-cyclodextrin, methoxypolyethylene glycol, or polyethylene glycol.

19. A pharmaceutical composition comprising the antibody or antigen binding fragment any one of claims 1, 2, and 3, and a pharmaceutically acceptable carrier.

20. The pharmaceutical composition of claim 19, wherein the pharmaceutically acceptable carrier is hyaluronidase.

21. The pharmaceutical composition of claim 19, further comprising an imaging agent, a cytotoxic agent, an angiogenesis inhibitor, a kinase inhibitor, a co-stimulation molecule blocker, an adhesion molecule blocker, an anti-cytokine antibody or functional fragment thereof, methotrexate, cyclosporine, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antpsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog thereof, a cytokine, or a cytokine antagonist.

22. A pharmaceutical composition comprising the antibody or antigen binding fragment of claim 4 and a pharmaceutically acceptable carrier.

23. The pharmaceutical composition of claim 22, further comprising at least one additional therapeutic agent for treating a disorder in which prostaglandin $E_2$ activity is detrimental.

* * * * *

```
SEQUENCE LISTING

<160> NUMBER OF SEQ ID NOS: 83

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 106
<212> TYPE: PRT
<213> ORGANISM: Homo sapiens

<400> SEQUENCE: 3

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 4
<211> LENGTH: 105
<212> TYPE: PRT
<213> ORGANISM: Homo sapiens

<400> SEQUENCE: 4

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

```
<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Gln Ser Gly Ala Glu Val Lys Arg Pro Gly Ala
1               5                   10                  15

Ser Val Lys Val Ser Cys Lys Thr Ser Gly Tyr Thr Phe Thr Asn Tyr
            20                  25                  30

Asp Ile Asn Trp Val Arg Leu Ala Pro Gly Gln Gly Leu Glu Trp Met
        35                  40                  45

Gly Cys Met Asn Pro Thr Thr Gly Lys Thr Gly Tyr Ala Gln Lys Phe
    50                  55                  60

Gln Gly Arg Val Thr Met Thr Arg Asp Thr Thr Ile Ala Thr Ala Tyr
65                  70                  75                  80

Met Glu Leu Ser Arg Leu Thr Ser Glu Asp Thr Ala Val Tyr Tyr Cys
                85                  90                  95

Ala Arg Gly Arg Gly Tyr Ser Pro Gly Tyr Gly Val Ala Tyr Ala Asp
            100                 105                 110

Tyr Trp Gly Gln Gly Thr Leu Val Thr Val Ser Ser
        115                 120

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Tyr Asp Ile Asn
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Met Asn Pro Thr Thr Gly Lys Thr Gly Tyr Ala Gln Lys Phe Gln
1               5                   10                  15

Gly

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Arg Gly Tyr Ser Pro Gly Tyr Gly Val Ala Tyr Ala Asp Tyr
1               5                   10                  15
```

```
<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Leu Thr Gln Ser Pro Ser Ser Leu Pro Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Thr Pro Gly Lys Ala Pro Ser Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Pro Pro
                85                  90                  95

Thr Phe Gly Gly Gly Thr Lys Val Glu Ile Lys Arg
            100                 105

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Ser Ile Ser Thr Tyr Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Ser Ser Leu Gln Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Ser Tyr Ser Pro Pro Pro Thr
1               5

<210> SEQ ID NO 13
<211> LENGTH: 126
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 13

Glu Val Gln Leu Val Gln Ser Gly Ala Glu Thr Lys Lys Pro Gly Ala
1               5                   10                  15

Ser Val Glu Val Ser Cys Lys Ala Ser Gly Tyr Ser Phe Thr Glu Tyr
                20                  25                  30

Gly Ile Ser Trp Val Arg Gln Ala Pro Gly Gln Gly Pro Glu Trp Met
            35                  40                  45

Gly Cys Ile Ser Pro Tyr Asn Gly Lys Leu His Tyr Ala Gln Glu Phe
    50                  55                  60

Gln Gly Arg Val Thr Met Thr Thr Gly Thr Ser Thr Asn Thr Ala Tyr
65                  70                  75                  80

Met Glu Leu Gly Ser Leu Arg Ser Asp Asp Thr Ala Val Tyr Tyr Cys
                85                  90                  95

Ala Arg Gly Gly Phe Ser Phe Tyr Asp Ser Ser Gly Tyr Tyr Tyr Val
            100                 105                 110

Thr Asp His Trp Gly Gln Gly Thr Leu Val Thr Val Ser Ser
        115                 120                 125

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Tyr Gly Ile Ser
1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Ile Ser Pro Tyr Asn Gly Lys Leu His Tyr Ala Gln Glu Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Phe Ser Phe Tyr Asp Ser Ser Gly Tyr Tyr Tyr Val Thr Asp
1               5                   10                  15

His
```

```
<210> SEQ ID NO 17
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Ser Gly Lys Ala Pro Lys Leu Leu Ile
        35                  40                  45

Tyr Ala Ala Ser Lys Leu Gln Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Ser Ala Thr Tyr Tyr Cys Gln Gln Ser Asp Thr Thr Pro Phe
                85                  90                  95

Thr Phe Gly Gln Gly Thr Lys Leu Glu Ile Lys Arg
            100                 105

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gln Ser Ile Gly Ser Tyr Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Ser Lys Leu Gln Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Ser Asp Thr Thr Pro Phe Thr
1               5

<210> SEQ ID NO 21
<211> LENGTH: 126
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 21

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Glu Tyr
            20                  25                  30

Gly Ile Ser Trp Val Arg Gln Ala Pro Gly Gln Gly Pro Glu Trp Met
        35                  40                  45

Gly Cys Ile Ser Pro Tyr Asn Gly Lys Leu His Tyr Ala Gln Lys Phe
    50                  55                  60

Leu Gly Arg Val Thr Met Thr Thr Asp Thr Ser Thr Asn Thr Ala Tyr
65                  70                  75                  80

Met Glu Leu Arg Ser Leu Lys Ser Asp Asp Thr Ala Val Tyr Tyr Cys
                85                  90                  95

Ala Arg Gly Gly Phe Ser Ser Tyr Asp Ser Ser Gly Tyr Tyr Tyr Val
            100                 105                 110

Thr Asp His Trp Gly Gln Gly Thr Leu Val Thr Val Ser Ser
        115                 120                 125

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Ile Ser Pro Tyr Asn Gly Lys Leu His Tyr Ala Gln Lys Phe Leu
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Phe Ser Ser Tyr Asp Ser Ser Gly Tyr Tyr Tyr Val Thr Asp
1               5                   10                  15

His

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Arg Leu Thr Gln Ser Pro Ser Ser Leu Pro Ala Ser Val Gly
1               5                   10                  15

Asp Arg Val Thr Ile Thr Cys Arg Ala Ser Gln Ser Ile Ser Thr Tyr
            20                  25                  30
```

```
Leu Asn Trp Tyr Gln Gln Thr Pro Gly Lys Ala Pro Ser Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Pro
                 85                  90                  95

Thr Phe Gly Gly Gly Thr Lys Val Glu Ile Lys Arg
             100                 105
```

```
<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25
```

```
Glu Val Gln Leu Val Gln Ser Gly Pro Glu Leu Lys Lys Pro Gly Thr
 1               5                  10                  15

Ser Val Lys Val Ser Cys Lys Ala Ser Gly Tyr Thr Leu Thr Thr Tyr
             20                  25                  30

Ala Met Asn Trp Val Arg Gln Ala Pro Gly Gln Gly Leu Glu Trp Met
         35                  40                  45

Gly Trp Ile Asp Thr Ser Thr Gly Asn Pro Thr Tyr Ala Pro Gly Phe
 50                  55                  60

Leu Gly Arg Phe Val Phe Ser Leu Asp Thr Ser Leu Ser Thr Thr Tyr
 65                  70                  75                  80

Leu Gln Ile Ser Ser Leu Lys Pro Asp Asp Thr Ala Val Tyr Tyr Cys
                 85                  90                  95

Ala Arg Ser Ser His Thr Arg Pro Gly Asp Phe Trp Gly Gln Gly Thr
             100                 105                 110

Leu Val Thr Val Ser Ser
        115
```

```
<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Thr Tyr Ala Met Asn
 1               5
```

```
<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Trp Ile Asp Thr Ser Thr Gly Asn Pro Thr Tyr Ala Pro Gly Phe Leu
 1               5                  10                  15

Gly
```

```
<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ser His Thr Arg Pro Gly Asp Phe
1               5

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ser Gly Leu Thr Gln Pro Pro Ser Val Ser Gly Thr Pro Gly Gln
1               5                   10                  15

Arg Val Thr Ile Ser Cys Ser Gly Ser Glu Ser Asn Val Gly Thr Asn
            20                  25                  30

Ser Val Asn Trp Tyr Gln Gln Leu Pro Gly Ala Ala Pro Arg Leu Leu
        35                  40                  45

Ile Arg Gly Asn Ser Asp Arg Pro Ser Gly Val Pro Asp Arg Phe Ser
    50                  55                  60

Ala Ser Lys Ser Gly Thr Ser Ala Ser Leu Ala Ile Ser Arg Leu Gln
65                  70                  75                  80

Ser Glu Asp Glu Ala Asp Tyr Phe Cys Gly Ala Cys Asp Gly Arg Leu
                85                  90                  95

Ser Gly Leu Tyr Val Phe Gly Thr Gly Thr Lys Val Thr Val Leu
            100                 105                 110

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Gly Ser Glu Ser Asn Val Gly Thr Asn Ser Val Asn
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Asn Ser Asp Arg Pro
1               5

<210> SEQ ID NO 32
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 32

Gly Ala Cys Asp Gly Arg Leu Ser Gly Leu Tyr Val
1               5                   10

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Gln Ser Gly Ser Glu Leu Lys Lys Pro Gly Thr
1               5                   10                  15

Ser Val Lys Val Ser Cys Lys Ala Ser Gly Tyr Thr Leu Thr Thr Tyr
            20                  25                  30

Ala Met Asn Trp Val Arg Gln Ala Pro Gly Gln Gly Leu Glu Trp Met
        35                  40                  45

Gly Trp Ile Gly Thr Ser Thr Gly Asn Pro Thr Tyr Ala Gln Gly Phe
    50                  55                  60

Thr Gly Arg Phe Val Phe Ser Leu Asp Thr Ser Val Asn Thr Ala His
65                  70                  75                  80

Leu Gln Ile Tyr Ser Leu Lys Ala Glu Asp Thr Ala Leu Tyr Tyr Cys
                85                  90                  95

Ala Arg Ser Ser Leu Thr Arg Pro Ala Asp Tyr Trp Gly Gln Gly Thr
            100                 105                 110

Leu Val Thr Val Ser Ser
        115

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Ile Gly Thr Ser Thr Gly Asn Pro Thr Tyr Ala Gln Gly Phe Thr
1               5                   10                  15

Gly

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ser Leu Thr Arg Pro Ala Asp Tyr
1               5

<210> SEQ ID NO 36
<211> LENGTH: 111
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 36

Gln Ser Gly Leu Thr Gln Pro Pro Ser Val Ser Gly Ala Pro Gly Gln
1               5                   10                  15

Arg Val Thr Ile Ser Cys Phe Gly Ser Ser Asn Ile Gly Ala Gly
            20                  25                  30

Tyr Asp Val His Trp Tyr Gln Gln Leu Pro Gly Ala Ala Pro Lys Leu
        35                  40                  45

Leu Ile Phe Gly Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Cys Asp Ser Ser
                85                  90                  95

Leu Ser Gly Ala Val Phe Gly Thr Gly Thr Lys Val Thr Val Leu
            100                 105                 110

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Gly Ser Ser Ser Asn Ile Gly Ala Gly Tyr Asp Val His
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asn Asn Asn Arg Pro
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Cys Asp Ser Ser Leu Ser Gly Ala Val
1               5                   10

<210> SEQ ID NO 40
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 40

Gln Val Gln Leu Gln Gln Ser Gly Pro Glu Leu Val Arg Pro Gly Ser
1               5                   10                  15

Ser Val Lys Ile Ser Cys Lys Ala Ser Gly Tyr Thr Phe Thr Lys Tyr
            20                  25                  30

Trp Leu Gly Trp Val Lys Gln Arg Pro Gly His Gly Leu Glu Trp Ile
        35                  40                  45

Gly Asp Ile Tyr Pro Gly Tyr Asp Tyr Thr His Tyr Asn Glu Lys Phe
    50                  55                  60

Lys Asp Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Asp Gly Ser Ser Thr Tyr Trp Gly Gln Gly Thr Leu Val
            100                 105                 110

Thr Val Ser Ala
        115

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Val Leu Met Thr Gln Thr Pro Leu Ser Leu Pro Val Ser Leu Gly
1               5                   10                  15

Asp Gln Ala Ser Ile Ser Cys Thr Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Val Phe Thr Leu Lys Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Arg

<210> SEQ ID NO 42
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Ser Gly Pro Glu Leu Val Arg Pro Gly Ser
1               5                   10                  15

Ser Val Lys Ile Ser Cys Lys Ala Ser Gly Tyr Thr Phe Thr Lys Tyr
            20                  25                  30

Trp Leu Gly Trp Val Lys Gln Arg Pro Gly His Gly Leu Glu Trp Ile
        35                  40                  45
```

```
Gly Asp Ile Tyr Pro Gly Tyr Asp Tyr Thr His Tyr Asn Glu Lys Phe
 50                  55                  60

Lys Asp Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Ile Tyr Tyr Cys
             85                  90                  95

Ala Arg Ser Asp Gly Ser Ser Thr Tyr Trp Gly Gln Gly Thr Leu Val
            100                 105                 110

Thr Val Ser Ala
        115

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Val Leu Met Thr Gln Thr Pro Leu Ser Leu Pro Val Ser Leu Gly
 1               5                  10                  15

Asp Gln Ala Ser Ile Ser Cys Thr Ser Ser Gln Asn Ile Val His Ser
             20                  25                  30

Asn Gly Asn Thr Tyr Leu Glu Trp Tyr Leu Gln Arg Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Val Phe Thr Leu Lys Ile
 65                  70                  75                  80

Ser Arg Val Glu Ala Glu Asp Leu Gly Val Tyr Tyr Cys Phe Gln Val
             85                  90                  95

Ser His Val Pro Tyr Thr Phe Gly Gly Gly Thr Lys Leu Glu Ile Lys
            100                 105                 110

Arg

<210> SEQ ID NO 44
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Gln Gln Ser Gly Pro Glu Leu Val Arg Pro Gly Ser
 1               5                  10                  15

Ser Val Lys Ile Ser Cys Lys Ala Ser Gly Tyr Thr Phe Thr Lys Tyr
             20                  25                  30

Trp Leu Gly Trp Val Lys Gln Arg Pro Gly His Gly Leu Glu Trp Ile
         35                  40                  45

Gly Asp Ile Tyr Pro Tyr Gly Asp Tyr Thr His Tyr Asn Glu Lys Phe
 50                  55                  60

Lys Asp Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Phe Cys
             85                  90                  95
```

Ala Arg Ser Asp Gly Ser Ser Thr Tyr Trp Gly Gln Gly Thr Leu Val
            100                 105                 110

Thr Val Ser Ala
        115

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Val Leu Met Thr Gln Thr Pro Leu Ser Leu Pro Val Ser Leu Gly
1               5                   10                  15

Asp Gln Ala Ser Ile Ser Cys Thr Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Val Phe Thr Leu Lys Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Arg

<210> SEQ ID NO 46
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Val Gln Leu Gln Gln Ser Gly Pro Glu Leu Val Arg Pro Gly Ser
1               5                   10                  15

Ser Val Lys Ile Ser Cys Lys Ala Ser
            20                  25

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Val Lys Gln Arg Pro Gly His Gly Leu Glu Trp Ile Gly
1               5                   10

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 48

Lys Ala Thr Leu Thr Val Asp Thr Ser Ser Thr Ala Tyr Met Gln
1               5                   10                  15

Leu Ser Ser Leu Thr Ser Glu Asp Ser Ala Ile Tyr Tyr Cys Ala Arg
            20                  25                  30

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Gly Gln Gly Thr Leu Val Thr Val Ser Ala
1               5                   10

<210> SEQ ID NO 50
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Tyr Leu Gln Arg Pro Gly Gln Ser Pro Lys Leu Leu Ile Tyr
1               5                   10                  15

<210> SEQ ID NO 52
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Val Pro Asp Arg Phe Ser Gly Ser Gly Ser Gly Thr Val Phe Thr Leu
1               5                   10                  15

Lys Ile Ser Arg Val Glu Ala Glu Asp Leu Gly Val Tyr Tyr Cys
            20                  25                  30

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 53

Phe Gly Gly Gly Thr Lys Leu Glu Ile Lys Arg
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Tyr Thr Phe Thr Lys Tyr Trp Leu Gly
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ile Tyr Pro Gly Tyr Asp Tyr Thr His Tyr Asn Glu Lys Phe Lys
1               5                   10                  15

Asp

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Asp Gly Ser Ser Thr Tyr
1               5

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ser Ser Gln Asn Ile Val His Ser Asn Gly Asn Thr Tyr Leu Glu
1               5                   10                  15

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Val Ser Asn Arg Phe Ser Gly
1               5
```

```
<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Gln Val Ser His Val Pro Tyr Thr
1               5

<210> SEQ ID NO 60
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Tyr Asp Tyr Thr His Tyr Asn Glu Lys Phe
    50                  55                  60

Lys Asp Arg Ala Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Val Val Met Thr Gln Thr Pro Leu Ser Leu Pro Val Thr Pro Gly
1               5                   10                  15

Glu Pro Ala Ser Ile Ser Cys Thr Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95
```

```
Ser His Val Pro Tyr Thr Phe Gly Gly Gly Thr Lys Val Glu Ile Lys
                100                 105                 110

Arg

<210> SEQ ID NO 62
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
                20                  25                  30

Trp Leu Gly Trp Val Arg Gln Ala Pro Gly Gln Gly Leu Glu Trp Ile
            35                  40                  45

Gly Asp Ile Tyr Pro Gly Tyr Asp Tyr Thr His Tyr Asn Glu Lys Phe
        50                  55                  60

Lys Asp Arg Ala Thr Leu Thr Val Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ser Asp Gly Ser Ser Thr Tyr Trp Gly Gln Gly Thr Leu Val
                100                 105                 110

Thr Val Ser Ser
            115

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Val Val Met Thr Gln Thr Pro Leu Ser Leu Pro Val Thr Pro Gly
1               5                   10                  15

Glu Pro Ala Ser Ile Ser Cys Thr Ser Ser Gln Asn Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Val Glu Ile Lys
                100                 105                 110

Arg

<210> SEQ ID NO 64
<211> LENGTH: 116
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Tyr Asp Tyr Thr His Tyr Asn Glu Lys Phe
    50                  55                  60

Lys Asp Arg Ala Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 65
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Val Leu Met Thr Gln Thr Pro Leu Ser Leu Pro Val Thr Pro Gly
1               5                   10                  15

Glu Pro Ala Ser Ile Ser Cys Thr Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Val Glu Ile Lys
            100                 105                 110

Arg

<210> SEQ ID NO 66
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30
```

```
Trp Leu Gly Trp Val Arg Gln Ala Pro Gly Gln Gly Leu Glu Trp Ile
            35                  40                  45

Gly Asp Ile Tyr Pro Gly Tyr Asp Tyr Thr His Tyr Asn Glu Lys Phe
 50                  55                  60

Lys Asp Arg Ala Thr Leu Thr Val Asp Thr Ser Thr Ser Thr Ala Tyr
 65                  70                  75                  80

Met Glu Leu Ser Ser Leu Arg Ser Asp Asp Thr Ala Val Tyr Tyr Cys
                85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 67
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Val Leu Met Thr Gln Thr Pro Leu Ser Leu Pro Val Thr Pro Gly
 1               5                  10                  15

Glu Pro Ala Ser Ile Ser Cys Thr Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Val Glu Ile Lys
            100                 105                 110

Arg

<210> SEQ ID NO 68
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Lys Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Tyr Asp Tyr Thr His Tyr Asn Glu Lys Phe
 50                  55                  60

Lys Asp Arg Val Thr Leu Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95
```

```
Ala Arg Ser Asp Gly Ser Ser Thr Tyr Trp Gly Gln Gly Thr Leu Val
            100                 105                 110

Thr Val Ser Ser
        115

<210> SEQ ID NO 69
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Val Val Met Thr Gln Thr Pro Leu Ser Leu Pro Val Thr Pro Gly
1               5                   10                  15

Glu Pro Ala Ser Ile Ser Cys Thr Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Val Glu Ile Lys
            100                 105                 110

Arg

<210> SEQ ID NO 70
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Tyr Asp Tyr Thr His Tyr Asn Glu Lys Phe
50                  55                  60

Lys Asp Arg Val Thr Leu Thr Thr Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 71
<211> LENGTH: 113
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 71

Asp Val Val Met Thr Gln Thr Pro Leu Ser Leu Pro Val Thr Pro Gly
1               5                   10                  15

Glu Pro Ala Ser Ile Ser Cys Thr Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Val Glu Ile Lys
            100                 105                 110

Arg

<210> SEQ ID NO 72
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Tyr Asp Tyr Thr His Tyr Asn Glu Lys Phe
    50                  55                  60

Lys Asp Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 73
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Val Leu Met Thr Gln Thr Pro Leu Ser Leu Pro Val Thr Pro Gly
1               5                   10                  15

Glu Pro Ala Ser Ile Ser Cys Thr Ser Ser Gln Asn Ile Val His Ser
            20                  25                  30
```

```
Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Val
                 85                  90                  95

Ser His Val Pro Tyr Thr Phe Gly Gly Gly Thr Lys Val Glu Ile Lys
            100                 105                 110

Arg

<210> SEQ ID NO 74
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Lys Tyr
             20                  25                  30

Trp Leu Gly Trp Val Arg Gln Ala Pro Gly Gln Gly Leu Glu Trp Met
            35                  40                  45

Gly Asp Ile Tyr Pro Gly Tyr Asp Tyr Thr His Tyr Asn Glu Lys Phe
 50                  55                  60

Lys Asp Arg Val Thr Leu Thr Thr Asp Thr Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 75
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Val Leu Met Thr Gln Thr Pro Leu Ser Leu Pro Val Thr Pro Gly
 1               5                  10                  15

Glu Pro Ala Ser Ile Ser Cys Thr Ser Ser Gln Asn Ile Val His Ser
             20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Val
                 85                  90                  95
```

-continued

Ser His Val Pro Tyr Thr Phe Gly Gly Gly Thr Lys Val Glu Ile Lys
              100                 105                 110

Arg

<210> SEQ ID NO 76
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Tyr Asp Tyr Thr His Tyr Asn Glu Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Asp Gly Ser Ser Thr Tyr Trp Gly Gln Gly Thr Leu Val
                100                 105                 110

Thr Val Ser Ser
            115

<210> SEQ ID NO 77
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Val Met Thr Gln Thr Pro Leu Ser Leu Pro Val Thr Pro Gly
1               5                   10                  15

Glu Pro Ala Ser Ile Ser Cys Thr Ser Ser Gln Asn Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Val Glu Ile Lys
                100                 105                 110

Arg

<210> SEQ ID NO 78
<211> LENGTH: 116
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Tyr Asp Tyr Thr His Tyr Asn Glu Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 79
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 79

Glu Leu Val Met Thr Gln Ser Pro Leu Ser Leu Pro Val Thr Pro Gly
1               5                   10                  15

Glu Pro Ala Ser Ile Ser Cys Thr Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gln Gly Thr Lys Leu Glu Ile Lys
            100                 105                 110

<210> SEQ ID NO 80
<211> LENGTH: 116
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

```
Trp Leu Gly Trp Val Arg Gln Ala Pro Gly Gln Gly Leu Glu Trp Ile
            35                  40                  45

Gly Asp Ile Tyr Pro Gly Tyr Asp Tyr Thr His Tyr Asn Glu Lys Phe
        50                  55                  60

Lys Asp Lys Ala Thr Leu Thr Val Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Asp Gly Ser Ser Thr Tyr Trp Gly Gln Gly Thr Leu Val
            100                 105                 110

Thr Val Ser Ser
        115

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Val Met Thr Gln Ser Pro Leu Ser Leu Pro Val Thr Pro Gly
 1               5                  10                  15

Glu Pro Ala Ser Ile Ser Cys Thr Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Val Phe Thr Leu Lys Ile
 65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gln Gly Thr Lys Leu Glu Ile Lys
            100                 105                 110

<210> SEQ ID NO 82
<211> LENGTH: 116
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 82

Gln Val Gln Leu Gln Gln Ser Gly Pro Glu Leu Val Arg Pro Gly Ser
 1               5                  10                  15

Ser Val Lys Ile Ser Cys Lys Ala Ser Gly Tyr Thr Phe Thr Lys Tyr
            20                  25                  30

Trp Leu Gly Trp Val Lys Gln Arg Pro Gly His Gly Leu Glu Trp Ile
            35                  40                  45

Gly Asp Ile Tyr Pro Gly Tyr Asp Tyr Thr His Tyr Asn Glu Lys Phe
        50                  55                  60

Lys Asp Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Phe Cys
                85                  90                  95
```

-continued

```
Ala Arg Ser Asp Gly Ser Ser Thr Tyr Trp Gly Gln Gly Thr Leu Val
            100                 105                 110

Thr Val Ser Ala
        115

<210> SEQ ID NO 83
<211> LENGTH: 113
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 83

Asp Val Leu Met Thr Gln Thr Pro Leu Ser Leu Pro Val Ser Leu Gly
1               5                   10                  15

Asp Gln Ala Ser Ile Ser Cys Thr Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Val Phe Thr Leu Lys Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Arg
```